(12) United States Patent
Chakravarti et al.

(10) Patent No.: US 10,480,033 B2
(45) Date of Patent: Nov. 19, 2019

(54) MIRNA-BASED PREDICTIVE MODELS FOR DIAGNOSIS AND PROGNOSIS OF PROSTATE CANCER

(71) Applicants: OHIO STATE INNOVATION FOUNDATION, Columbus, OH (US); UNIVERSITY OF FREIBURG, Freiburg (DE)

(72) Inventors: Arnab Chakravarti, Dublin, OH (US); Erica McKenzie Bell, Columbus, OH (US); Simon Kirste, Freiburg (DE); Anca-Ligia Grosu, Freiburg (DE)

(73) Assignees: Ohio State Innovation Foundation, Columbus, OH (US); University of Freiburg, Freiburg (DE)

( * ) Notice: Subject to any disclaimer, the term of this patent is extended or adjusted under 35 U.S.C. 154(b) by 0 days.

(21) Appl. No.: 15/543,721

(22) PCT Filed: Jan. 14, 2016

(86) PCT No.: PCT/US2016/013353
§ 371 (c)(1),
(2) Date: Jul. 14, 2017

(87) PCT Pub. No.: WO2016/115312
PCT Pub. Date: Jul. 21, 2016

(65) Prior Publication Data
US 2018/0002762 A1 Jan. 4, 2018

Related U.S. Application Data

(60) Provisional application No. 62/103,288, filed on Jan. 14, 2015.

(51) Int. Cl.
*A61K 48/00* (2006.01)
*C12N 15/11* (2006.01)
(Continued)

(52) U.S. Cl.
CPC .......... *C12Q 1/6886* (2013.01); *G16B 25/00* (2019.02); *G16B 40/00* (2019.02);
(Continued)

(58) Field of Classification Search
CPC .............. A61K 31/7125; C12N 15/113; C12N 2310/315; C12N 2310/321;
(Continued)

(56) References Cited

U.S. PATENT DOCUMENTS

| | | |
|---|---|---|
| 2010/0179213 A1 | 7/2010 | Patrawala et al. |
| 2013/0005837 A1 | 1/2013 | Moreno et al. |

(Continued)

FOREIGN PATENT DOCUMENTS

| | | |
|---|---|---|
| WO | 2011/082198 A2 | 7/2011 |
| WO | 2011/127219 A1 | 10/2011 |

(Continued)

OTHER PUBLICATIONS

Mongan et al. (Abstract #432) (European Journal of Cancer Nov. 2012 vol. 48, Supplement 6, p. 134).*

(Continued)

*Primary Examiner* — Terra C Gibbs
(74) *Attorney, Agent, or Firm* — Meunier Carlin & Curfman LLC

(57) ABSTRACT

The lack of clear predictors of prostate cancer progression leads to subjective decision-making regarding courses of treatment. The identification of new biomarkers that are predictive of recurrence after radical prostatectomy would advance the field of prostate cancer treatment. Disclosed are miRNAs that can be used as molecular biomarkers to detect or predict the progression of prostate cancer and to adjust a treatment plan accordingly. Furthermore, kits are included for the detection of these miRNAs.

7 Claims, 7 Drawing Sheets

(51) Int. Cl.
  C07H 21/02    (2006.01)
  C07H 21/04    (2006.01)
  C12Q 1/6886   (2018.01)
  G16B 25/00    (2019.01)
  G16B 40/00    (2019.01)
(52) U.S. Cl.
  CPC .. C12Q 2600/106 (2013.01); C12Q 2600/118 (2013.01); C12Q 2600/158 (2013.01); C12Q 2600/178 (2013.01)
(58) Field of Classification Search
  CPC ...... C12N 2310/341; C12N 2310/3341; C12Q 1/6886; C12Q 2600/118; C12Q 2600/158; C12Q 2600/178
  See application file for complete search history.

(56) References Cited

U.S. PATENT DOCUMENTS

2013/0053264 A1   2/2013   Keller et al.
2014/0309130 A1  10/2014   Haj-Ahmad

FOREIGN PATENT DOCUMENTS

WO   2012/015765 A2   2/2012
WO      2014085906    6/2014

OTHER PUBLICATIONS

Bell et al. (PLOS One, Mar. 11, 2015 vol. 10(3):pp. 1-19).*
Zhao et al. (International Journal of Molecular Sciences, 2017 vol. 18:pp. 1-32).*
Mark H. Ebell (Am Fam Physician, Dec. 15, 2005:72(12):2511-2512).*
International Search Report and Written Opinoin issued in International Application No. PCTUS2016013353, dated Mar. 17, 2016.
International Preliminary Report on Patentability issued in International Application No. PCTUS2016013353, dated Jul. 27, 2017.
Bell et al., (2015) A Novel MiRNA-Based Predictive Model for Biochemical Failure Following Post-Prostatectomy Salvage Radiation Therapy. PLoS One 10(3), 1-19.
Ambs S, Prueitt RL, Yi M, Hudson RS, Howe TM, et al. (2008) Genomic profiling of microRNA and messenger RNA reveals deregulated microRNA expression in prostate cancer. Cancer Res 68: 6162-6170.
Amling CL (2006) Biochemical recurrence after localized treatment. Urol Clin North Am 33: 147-159, v.
Amling CL, Blute ML, Bergstralh EJ, Seay TM, Slezak J, et al. (2000) Long-term hazard of progression after radical prostatectomy for clinically localized prostate cancer: continued risk of biochemical failure after 5 years. J Urol 164: 101-105.
Balaguer F, Link A, Lozano JJ, Cuatrecasas M, Nagasaka T, et al. (2010) Epigenetic silencing of miR-137 is an early event in colorectal carcinogenesis. Cancer Res 70: 6609-6618.
Bao L, Hazari S, Mehra S, Kaushal D, Moroz K, et al. (2012) Increased expression of P-glycoprotein and doxorubicin chemoresistance of metastatic breast cancer is regulated by miR-298. Am J Pathol 180: 2490-2503.
Bennett PE, Bemis L, Norris DA, Shellman YG (2013) miR in melanoma development: miRNAs and acquired hallmarks of cancer in melanoma. Physiol Genomics 45: 1049-1059.
Blenkiron C, Hurley DG, Fitzgerald S, Print CG, Lasham A (2013) Links between the oncoprotein YB-1 and small non-coding RNAs in breast cancer. PLoS One 8: e80171.
Botticella A, Guarneri A, Levra NG, Munoz F, Filippi AR, et al. (2014) Biochemical and clinical outcomes after high-dose salvage radiotherapy as monotherapy for prostate cancer. J Cancer Res Clin Oncol 140: 1111-1116.
Bronisz A, Godlewski J, Wallace JA, Merchant AS, Nowicki MO, et al. (2012) Reprogramming of the tumour microenvironment by stromal PTEN-regulated miR-320. Nat Cell Biol 14: 159-167.
Bryant RJ, Pawlowski T, Catto JW, Marsden G, Vessella RL, et al. (2012) Changes in circulating microRNA levels associated with prostate cancer. Br J Cancer 106: 768-774.
Cao YX, Dai CW, Zhang GS (2010) [Screening for drug resistance related microRNAs in K562 and K562/A02 cell lines.]. Zhonghua Xue Ye Xue Za Zhi 31: 361-365. Abstract.
Chen L, Yan HX, Yang W, Hu L, Yu LX, et al. (2009) The role of microRNA expression pattern in human intrahepatic cholangiocarcinoma. J Hepatol 50: 358-369.
Chen Q, Chen X, Zhang M, Fan Q, Luo S, et al. (2011) miR-137 is frequently down-regulated in gastric cancer and is a negative regulator of Cdc42. Dig Dis Sci 56: 2009-2016.
Cheng C, Chen ZQ, Shi XT (2014) MicroRNA-320 inhibits osteosarcoma cells proliferation by directly targeting fatty acid synthase. Tumour Biol 35: 4177-4183.
Cheng HH, Mitchell PS, Kroh EM, Dowell AE, Chery L, et al. (2013) Circulating microRNA profiling identifies a subset of metastatic prostate cancer patients with evidence of cancer-associated hypoxia. PLoS One 8: e69239.
Chiavacci E, Rizzo M, Pitto L, Patella F, Evangelista M, et al. (2014) The zebrafish/tumor xenograft angiogenesis assay as a tool for screening anti-angiogenic miRNAs. Cytotechnology.
Chowdhari S, Saini N (2014) hsa-miR-4516 Mediated Downregulation of STAT3/CDK6/UBE2N Plays a Role in PUVA Induced Apoptosis in Keratinocytes. J Cell Physiol.
Cookson MS, Aus G, Burnett AL, Canby-Hagino ED, D'Amico AV, et al. (2007) Variation in the definition of biochemical recurrence in patients treated for localized prostate cancer: the American Urological Association Prostate Guidelines for Localized Prostate Cancer Update Panel report and recommendations for a standard in the reporting of surgical outcomes. J Urol 177: 540-545.
Cooperberg MR, Freedland SJ, Pasta DJ, Elkin EP, Presti JC, Jr., et al. (2006) Multiinstitutional validation of the UCSF cancer of the prostate risk assessment for prediction of recurrence after radical prostatectomy. Cancer 107: 2384-2391.
Cooperberg MR, Pasta DJ, Elkin EP, Litwin MS, Latini DM, et al. (2005) The University of California, San Francisco Cancer of the Prostate Risk Assessment score: a straightforward and reliable preoperative predictor of disease recurrence after radical prostatectomy. J Urol 173: 1938-1942.
D'Amico AV, Whittington R, Malkowicz SB, Wu YH, Chen M, et al. (2000) Combination of the preoperative PSA level, biopsy gleason score, percentage of positive biopsies, and MRI T-stage to predict early PSA failure in men with clinically localized prostate cancer. Urology 55: 572-577.
Dang J, Bian YQ, Sun JY, Chen F, Dong GY, et al. (2013) MicroRNA-137 promoter methylation in oral lichen planus and oral squamous cell carcinoma. J Oral Pathol Med 42: 315-321.
Den RB, Feng FY, Showalter TN, Mishra MV, Trabulsi EJ, et al. (2014) Genomic prostate cancer classifier predicts biochemical failure and metastases in patients after postoperative radiation therapy. Int J Radiat Oncol Biol Phys 89: 1038-1046.
Dong L, Li Y, Han C, Wang X, She L, et al. (2014) miRNA microarray reveals specific expression in the peripheral blood of glioblastoma patients. Int J Oncol 45: 746-756.
Epstein JI, Allsbrook WC, Jr., Amin MB, Egevad LL (2005) The 2005 International Society of Urological Pathology (ISUP) Consensus Conference on Gleason Grading of Prostatic Carcinoma. Am J Surg Pathol 29: 1228-1242.
Erho N, Crisan A, Vergara IA, Mitra AP, Ghadessi M, et al. (2013) Discovery and validation of a prostate cancer genomic classifier that predicts early metastasis following radical prostatectomy. PLoS One 8: e66855.
Fan Y, Mao R, Yang J (2013) NF-kappaB and STAT3 signaling pathways collaboratively link inflammation to cancer. Protein Cell 4: 176-185.
Fendler A, Jung M, Stephan C, Honey RJ, Stewart RJ, et al. (2011) miRNAs can predict prostate cancer biochemical relapse and are involved in tumor progression. Int J Oncol 39: 1183-1192.

(56) References Cited

OTHER PUBLICATIONS

Fuse M, Kojima S, Enokida H, Chiyomaru T, Yoshino H, et al. (2012) Tumor suppressive microRNAs (miR-222 and miR-31) regulate molecular pathways based on microRNA expression signature in prostate cancer. J Hum Genet 57: 691-699.

Galardi S, Mercatelli N, Giorda E, Massalini S, Frajese GV, et al. (2007) miR-221 and miR-222 expression affects the proliferation potential of human prostate carcinoma cell lines by targeting p27Kip1. J Biol Chem 282: 23716-23724.

Gao W, Shen H, Liu L, Xu J, Shu Y (2011) MiR-21 overexpression in human primary squamous cell lung carcinoma is associated with poor patient prognosis. J Cancer Res Clin Oncol 137: 557-566.

Garofalo M, Quintavalle C, Romano G, Croce CM, Condorelli G (2012) miR221/222 in cancer: their role in tumor progression and response to therapy. Curr Mol Med 12: 27-33.

Geiss GK, Bumgarner RE, Birditt B, Dahl T, Dowidar N, et al. (2008) Direct multiplexed measurement of gene expression with color-coded probe pairs. Nat Biotechnol 26: 317-325.

Girardi C, De Pitta C, Casara S, Sales G, Lanfranchi G, et al. (2012) Analysis of miRNA and mRNA expression profiles highlights alterations in ionizing radiation response of human lymphocytes under modeled microgravity. PLoS One 7: e31293.

Gordanpour A, Nam RK, Sugar L, Seth A (2012) MicroRNAs in prostate cancer: from biomarkers to molecularly-based therapeutics. Prostate Cancer Prostatic Dis 15: 314-319.

Guo B, Li J, Liu L, Hou N, Chang D, et al. (2013) Dysregulation of miRNAs and their potential as biomarkers for the diagnosis of gastric cancer. Biomed Rep 1: 907-912.

Guo J, Xia B, Meng F, Lou G (2013) miR-137 suppresses cell growth in ovarian cancer by targeting AEG-1. Biochem Biophys Res Commun 441: 357-363.

Haj-Ahmad TA, Abdalla MA, Haj-Ahmad Y (2014) Potential Urinary miRNA Biomarker Candidates for the Accurate Detection of Prostate Cancer among Benign Prostatic Hyperplasia Patients. J Cancer 5: 182-191.

Hart M, Nolte E, Wach S, Szczyrba J, Taubert H, et al. (2014) Comparative microRNA profiling of prostate carcinomas with increasing tumor stage by deep sequencing. Mol Cancer Res 12: 250-263.

Heagerty PJ, Lumley T, Pepe MS (2000) Time-dependent ROC curves for censored survival data and a diagnostic marker. Biometrics 56: 337-344.

Hessvik NP, Phuyal S, Brech A, Sandvig K, Llorente A (2012) Profiling of microRNAs in exosomes released from PC-3 prostate cancer cells. Biochim Biophys Acta 1819: 1154-1163.

Hsieh IS, Chang KC, Tsai YT, Ke JY, Lu PJ, et al. (2013) MicroRNA-320 suppresses the stem cell-like characteristics of prostate cancer cells by downregulating the Wnt/beta-catenin signaling pathway. Carcinogenesis 34: 530-538.

Hudson RS, Yi M, Esposito D, Watkins SK, Hurwitz AA, et al. (2012) MicroRNA-1 is a candidate tumor suppressor and prognostic marker in human prostate cancer. Nucleic Acids Res 40: 3689-3703.

Kim WT, Kim WJ (2013) MicroRNAs in prostate cancer. Prostate Int 1: 3-9.

Kneitz B, Krebs M, Kalogirou C, Schubert M, Joniau S, et al. (2014) Survival in patients with high-risk prostate cancer is predicted by miR-221, which regulates proliferation, apoptosis, and invasion of prostate cancer cells by inhibiting IRF2 and SOCS3. Cancer Res 74: 2591-2603.

Knezevic D, Goddard AD, Natraj N, Cherbavaz DB, Clark-Langone KM, et al. (2013) Analytical validation of the Oncotype DX prostate cancer assay—a clinical RT-PCR assay optimized for prostate needle biopsies. BMC Genomics 14: 690.

Kojima S, Chiyomaru T, Kawakami K, Yoshino H, Enokida H, et al. (2012) Tumour suppressors miR-1 and miR-133a target the oncogenic function of purine nucleoside phosphorylase (PNP) in prostate cancer. Br J Cancer 106: 405-413.

Kunz M (2013) MicroRNAs in melanoma biology. Adv Exp Med Biol 774: 103-120.

Langevin SM, Stone RA, Bunker CH, Lyons-Weiler MA, LaFramboise WA, et al. (2011) MicroRNA-137 promoter methylation is associated with poorer overall survival in patients with squamous cell carcinoma of the head and neck. Cancer 117: 1454-1462.

Larne O, Martens-Uzunova E, Hagman Z, Edsjo A, Lippolis G, et al. (2013) miQ—a novel microRNA based diagnostic and prognostic tool for prostate cancer. Int J Cancer 132: 2867-2875.

Lee KH, Lotterman C, Karikari C, Omura N, Feldmann G, et al. (2009) Epigenetic silencing of MicroRNA miR-107 regulates cyclin-dependent kinase 6 expression in pancreatic cancer. Pancreatology 9: 293-301.

Li A, Yu J, Kim H, Wolfgang CL, Canto MI, et al. (2013) MicroRNA array analysis finds elevated serum miR-1290 accurately distinguishes patients with low-stage pancreatic cancer from healthy and disease controls. Clin Cancer Res 19: 3600-3610.

Liang S, Chen L, Huang H, Zhi D (2013) The experimental study of miRNA in pituitary adenomas. Turk Neurosurg 23: 721-727.

Lichner Z, Fendler A, Saleh C, Nasser AN, Boles D, et al. (2013) MicroRNA signature helps distinguish early from late biochemical failure in prostate cancer. Clin Chem 59: 1595-1603.

Liu A, Xu X (2011) MicroRNA isolation from formalin-fixed, paraffin-embedded tissues. Methods Mol Biol 724: 259-267.

Liu X, Chen Z, Yu J, Xia J, Zhou X (2009) MicroRNA profiling and head and neck cancer. Comp Funct Genomics: 837514.

Liu YN, Yin JJ, Abou-Kheir W, Hynes PG, Casey OM, et al. (2013) MiR-1 and miR-200 inhibit EMT via Slug-dependent and tumorigenesis via Slug-independent mechanisms. Oncogene 32: 296-306.

Lo U-G, Yang D, Hsieh J-T (2013) The role of microRNAs in prostate cancer progression. Translational Andrology and Urology 2: 228-241.

Long Q, Johnson BA, Osunkoya AO, Lai YH, Zhou W, et al. (2011) Protein-coding and microRNA biomarkers of recurrence of prostate cancer following radical prostatectomy. Am J Pathol 179: 46-54.

Magne N, Toillon RA, Bottero V, Didelot C, Houtte PV, et al. (2006) NF-kappaB modulation and ionizing radiation: mechanisms and future directions for cancer treatment. Cancer Lett 231: 158-168.

Makarov DV, Trock BJ, Humphreys EB, Mangold LA, Walsh PC, et al. (2007) Updated nomogram to predict pathologic stage of prostate cancer given prostate-specific antigen level, clinical stage, and biopsy Gleason score (Partin tables) based on cases from 2000 to 2005. Urology 69: 1095-1101.

Martens-Uzunova ES, Jalava SE, Dits NF, van Leenders GJ, Moller S, et al. (2012) Diagnostic and prognostic signatures from the small non-coding RNA transcriptome in prostate cancer. Oncogene 31: 978-991.

May M, Knoll N, Siegsmund M, Fahlenkamp D, Vogler H, et al. (2007) Validity of the CAPRA score to predict biochemical recurrence-free survival after radical prostatectomy. Results from a european multicenter survey of 1,296 patients. J Urol 178: 1957-1962; discussion 1962.

Mazeh H, Mizrahi I, Ilyayev N, Halle D, Brucher B, et al. (2013) The Diagnostic and Prognostic Role of microRNA in Colorectal Cancer—a Comprehensive review. J Cancer 4: 281-295.

Mercatelli N, Coppola V, Bonci D, Miele F, Costantini A, et al. (2008) The inhibition of the highly expressed miR-221 and miR-222 impairs the growth of prostate carcinoma xenografts in mice. PLoS One 3: e4029.

Mitchell PS, Parkin RK, Kroh EM, Fritz BR, Wyman SK, et al. (2008) Circulating microRNAs as stable blood-based markers for cancer detection. Proc Natl Acad Sci USA 105: 10513-10518.

Mosakhani N, Guled M, Leen G, Calabuig-Farinas S, Niini T, et al. (2012) An integrated analysis of miRNA and gene copy numbers in xenografts of Ewing's sarcoma. J Exp Clin Cancer Res 31: 24.

Nielsen T, Wallden B, Schaper C, Ferree S, Liu S, et al. (2014) Analytical validation of the PAM50-based Prosigna Breast Cancer Prognostic Gene Signature Assay and nCounter Analysis System using formalin-fixed paraffin-embedded breast tumor specimens. BMC Cancer 14: 177.

Nohata N, Hanazawa T, Enokida H, Seki N (2012) microRNA-1/133a and microRNA-206/133b clusters: dysregulation and functional roles in human cancers. Oncotarget 3: 9-21.

Noto JM, Piazuelo MB, Chaturvedi R, Bartel CA, Thatcher EJ, et al. (2013) Strain-specific suppression of microRNA-320 by carci-

(56) References Cited

OTHER PUBLICATIONS nogenic Helicobacter pylori promotes expression of the antiapoptotic protein Mcl-1. Am J Physiol Gastrointest Liver Physiol 305: G786-796.
Nygren MK, Tekle C, Ingebrigtsen VA, Makela R, Krohn M, et al. (2014) Identifying microRNAs regulating B7-H3 in breast cancer: the clinical impact of microRNA-29c. Br J Cancer 110: 2072-2080.
Ohdaira H, Nakagawa H, Yoshida K (2009) Profiling of molecular pathways regulated by microRNA 601. Comput Biol Chem 33: 429-433.
Partin AW, Mangold LA, Lamm DM, Walsh PC, Epstein JI, et al. (2001) Contemporary update of prostate cancer staging nomograms (Partin Tables) for the new millennium. Urology 58: 843-848.
Peng X, Guo W, Liu T, Wang X, Tu X, et al. (2011) Identification of miRs-143 and -145 that is associated with bone metastasis of prostate cancer and involved in the regulation of EMT. PLoS One 6: e20341.
Qin AY, Zhang XW, Liu L, Yu JP, Li H, et al. (2013) MiR-205 in cancer: an angel or a devil? Eur J Cell Biol 92: 54-60.
Quek SI, Ho ME, Loprieno MA, Ellis WJ, Elliott N, et al. (2012) A multiplex assay to measure RNA transcripts of prostate cancer in urine. PLoS One 7: e45656.
Reis PP, Waldron L, Goswami RS, Xu W, Xuan Y, et al. (2011) mRNA transcript quantification in archival samples using multiplexed, color-coded probes. BMC Biotechnol 11:46.
Riaz M, van Jaarsveld MT, Hollestelle A, Prager-van der Smissen WJ, Heine AA, et al. (2013) miRNA expression profiling of 51 human breast cancer cell lines reveals subtype and driver mutation-specific miRNAs. Breast Cancer Res 15: R33.
Schaar DG, Medina DJ, Moore DF, Strair RK, Ting Y (2009) miR-320 targets transferrin receptor 1 (CD71) and inhibits cell proliferation. Exp Hematol 37: 245-255.
Schaefer A, Jung M, Miller K, Lein M, Kristiansen G, et al. (2010) Suitable reference genes for relative quantification of miRNA expression in prostate cancer. Exp Mol Med 42: 749-758.
Schepeler T, Reinert JT, Ostenfeld MS, Christensen LL, Silahtaroglu AN, et al. (2008) Diagnostic and prognostic microRNAs in stage II colon cancer. Cancer Res 68: 6416-6424.
Schubert M, Spahn M, Kneitz S, Scholz CJ, Joniau S, et al. (2013) Distinct microRNA expression profile in prostate cancer patients with early clinical failure and the impact of let-7 as prognostic marker in high-risk prostate cancer. PLoS One 8: e65064.
Shang Y, Zhang Z, Liu Z, Feng B, Ren G, et al. (2014) miR-508-5p regulates multidrug resistance of gastric cancer by targeting ABCB1 and ZNRD1. Oncogene 33: 3267-3276.
Shimizu T, Suzuki H, Nojima M, Kitamura H, Yamamoto E, et al. (2013). Eur Urol 63: 1091-1100.
Singh PK, Preus L, Hu Q, Yan L, Long MD, et al. (2014) Serum microRNA expression patterns that predict early treatment failure in prostate cancer patients. Oncotarget 5: 824-840.
Skalsky RL, Cullen BR (2011) Reduced expression of brain-enriched microRNAs in glioblastomas permits targeted regulation of a cell death gene. PLoS One 6: e24248.
Srivastava A, Goldberger H, Dimtchev A, Marian C, Soldin O, et al. (2014) Circulatory miR-628-5p is downregulated in prostate cancer patients. Tumour Biol 35: 4867-4873.
Srivastava A, Goldberger H, Dimtchev A, Ramalinga M, Chijioke J, et al. (2013) MicroRNA profiling in prostate cancer—the diagnostic potential of urinary miR-205 and miR-214. PLoS One 8: e76994.
Stephenson AJ, Scardino PT, Eastham JA, Bianco FJ, Jr., Dotan ZA, et al. (2005) Postoperative nomogram predicting the 10-year probability of prostate cancer recurrence after radical prostatectomy. J Clin Oncol 23: 7005-7012.
Stephenson AJ, Scardino PT, Eastham JA, Bianco FJ, Jr., Dotan ZA, et al. (2006) Preoperative nomogram predicting the 10-year probability of prostate cancer recurrence after radical prostatectomy. J Natl Cancer Inst 98: 715-717.
Stephenson AJ, Scardino PT, Kattan MW, Pisansky TM, Slawin KM, et al. (2007) Predicting the outcome of salvage radiation therapy for recurrent prostate cancer after radical prostatectomy. J Clin Oncol 25: 2035-2041.
Sun T, Wang Q, Balk S, Brown M, Lee GS, et al. (2009) The role of microRNA-221 and microRNA-222 in androgen-independent prostate cancer cell lines. Cancer Res 69: 3356-3363.
Szczyrba J, Loprich E, Wach S, Jung V, Unteregger G, et al. (2010) The microRNA profile of prostate carcinoma obtained by deep sequencing. Mol Cancer Res 8: 529-538.
Tamim S, Vo DT, Uren PJ, Qiao M, Bindewald E, et al. (2014) Genomic analyses reveal broad impact of miR-137 on genes associated with malignant transformation and neuronal differentiation in glioblastoma cells. PLoS One 9: e85591.
Tao J, Wu D, Xu B, Qian W, Li P, et al. (2012) microRNA-133 inhibits cell proliferation, migration and invasion in prostate cancer cells by targeting the epidermal growth factor receptor. Oncol Rep 27: 1967-1975.
Thompson I, Thrasher JB, Aus G, Burnett AL, Canby-Hagino ED, et al. (2007) Guideline for the management of clinically localized prostate cancer: 2007 update. J Urol 177: 2106-2131.
Tiryakioglu D, Bilgin E, Holdenrieder S, Dalay N, Gezer U (2013) miR-141 and miR-375 induction and release are different from PSA mRNA and PCA3 upon androgen stimulation of LNCaP cells. Biomed Rep 1: 802-806.
Verdoodt B, Neid M, Vogt M, Kuhn V, Liffers ST, et al. (2013) MicroRNA-205, a novel regulator of the anti-apoptotic protein Bcl2, is downregulated in prostate cancer. Int J Oncol 43: 307-314.
Veuger SJ, Hunter JE, Durkacz BW (2009) Ionizing radiation-induced NF-kappaB activation requires PARP-1 function to confer radioresistance. Oncogene 28: 832-842.
Volinia S, Galasso M, Costinean S, Tagliavini L, Gamberoni G, et al. (2010) Reprogramming of miRNA networks in cancer and leukemia. Genome Res 20: 589-599.
Walter BA, Valera VA, Pinto PA, Merino MJ (2013) Comprehensive microRNA Profiling of Prostate Cancer. J Cancer 4: 350-357.
Wang D, Song W, Na Q (2012) The emerging roles of placenta-specific microRNAs in regulating trophoblast proliferation during the first trimester. Aust N Z J Obstet Gynaecol 52: 565-570.
Wang N, Li Q, Feng NH, Cheng G, Guan ZL, et al. (2013) miR-205 is frequently downregulated in prostate cancer and acts as a tumor suppressor by inhibiting tumor growth. Asian J Androl 15: 735-741.
Wang Y, Lee CG (2009) MicroRNA and cancer—focus on apoptosis. J Cell Mol Med 13: 12-23.
Wang Z, Wang J, Yang Y, Hao B, Wang R, et al. (2013) Loss of has-miR-337-3p expression is associated with lymph node metastasis of human gastric cancer. J Exp Clin Cancer Res 32: 76.
Watahiki A, Wang Y, Morris J, Dennis K, O'Dwyer HM, et al. (2011) MicroRNAs associated with metastatic prostate cancer. PLoS One 6: e24950.
Wu XL, Cheng B, Li PY, Huang HJ, Zhao Q, et al. (2013) MicroRNA-143 suppresses gastric cancer cell growth and induces apoptosis by targeting COX-2. World J Gastroenterol 19: 7758-7765.
Wu YY, Chen YL, Jao YC, Hsieh IS, Chang KC, et al. (2014) miR-320 regulates tumor angiogenesis driven by vascular endothelial cells in oral cancer by silencing neuropilin 1. Angiogenesis 17. 247-260.
Yan H, Wang S, Yu H, Zhu J, Chen C (2013) Molecular pathways and functional analysis of miRNA expression associated with paclitaxel-induced apoptosis in hepatocellular carcinoma cells. Pharmacology 92: 167-174.
Yan JW, Lin JS, He XX (2014) The emerging role of miR-375 in cancer. Int J Cancer 135: 1011-1018.
Yan LX, Huang XF, Shao Q, Huang MY, Deng L, et al. (2008) MicroRNA miR-21 overexpression in human breast cancer is associated with advanced clinical stage, lymph node metastasis and patient poor prognosis. RNA 14: 2348-2360.
Yang M, Liu R, Sheng J, Liao J, Wang Y, et al. (2013) Differential expression profiles of microRNAs as potential biomarkers for the early diagnosis of esophageal squamous cell carcinoma. Oncol Rep 29: 169-176.

(56) References Cited

OTHER PUBLICATIONS

Yang Y, Gu X, Zhou M, Xiang J, Chen Z (2013) Serum microRNAs: A new diagnostic method for colorectal cancer. Biomed Rep 1: 495-498.

Yao Y, Suo AL, Li ZF, Liu LY, Tian T, et al. (2009) MicroRNA profiling of human gastric cancer. Mol Med Rep 2: 963-970.

Yoshino H, Seki N, Itesako T, Chiyomaru T, Nakagawa M, et al. (2013) Aberrant expression of microRNAs in bladder cancer. Nat Rev Urol 10: 396-404.

Yu X, Zhang X, Bi T, Ding Y, Zhao J, et al. (2013) MiRNA expression signature for potentially predicting the prognosis of ovarian serous carcinoma. Tumour Biol 34: 3501-3508.

Zhai Q, Zhou L, Zhao C, Wan J, Yu Z, et al. (2012) Identification of miR-508-3p and miR-509-3p that are associated with cell invasion and migration and involved in the apoptosis of renal cell carcinoma. Biochem Biophys Res Commun 419: 621-626.

Zhao BS, Liu SG, Wang TY, Ji YH, Qi B, et al. (2013) Screening of microRNA in patients with esophageal cancer at same tumor node metastasis stage with different prognoses. Asian Pac J Cancer Prev 14: 139-143.

Zhao JJ, Yang J, Lin J, Yao N, Zhu Y, et al. (2009) Identification of miRNAs associated with tumorigenesis of retinoblastoma by miRNA microarray analysis. Childs Nerv Syst 25: 13-20.

Zhao Y, Li Y, Lou G, Zhao L, Xu Z, et al. (2012) MiR-137 targets estrogen-related receptor alpha and impairs the proliferative and migratory capacity of breast cancer cells. PLoS One 7: e39102.

Ziliak D, Gamazon ER, Lacroix B, Kyung Im H, Wen Y, et al. (2012) Genetic variation that predicts platinum sensitivity reveals the role of miR-193b* in chemotherapeutic susceptibility. Mol Cancer Ther 11: 2054-2061.

European Patent Office. Communication Pursuant to Rule 164(1) EPC. European Application No. 16737859.5. dated Jun. 27, 2018. 17 pages.

Li, Tao, et al. "miR-21 as an independent biochemical recurrence predictor and potential therapeutic target for prostate cancer." The Journal of urology 187.4 (2012): 1466-1472. (Abstract Only).

Schaefer, A., Jung, M., Mollenkopf, H. J., Wagner, I., Stephan, C., Jentzmik, F., . . . & Jung, K. (2009). Diagnostic and prognostic implications of microRNA profiling in prostate carcinoma. International journal of cancer, 126(5), 1166-1176.

Extended European Search Report issued for European Application No. 16737859, dated Sep. 28, 2018, 13 pages.

* cited by examiner

MIRNA-BASED PREDICTIVE MODELS FOR DIAGNOSIS AND PROGNOSIS OF PROSTATE CANCER

CROSS-REFERENCE TO RELATED APPLICATIONS

This application is a national stage application filed under 35 U.S.C. § 371 of PCT/US2016/013353 filed Jan. 14, 2016, which claims benefit of U.S. Provisional Application No. 62/103,288, filed Jan. 14, 2015, which is hereby incorporated herein by reference in its entirety.

STATEMENT REGARDING FEDERALLY SPONSORED RESEARCH OR DEVELOPMENT

This invention was made with government support under U10 CA180850 and R01 CA188500 awarded by the National Institutes of Health. The government has certain rights in the invention.

BACKGROUND

Prostate cancer (PCa) is one of the most common cancers worldwide and the most common cancer in men. However, treatment strategies remain highly controversial. Radical prostatectomy (RP), or complete removal of the prostate gland, is a common treatment option for men with early-stage PCa. Long-term data indicate that 30-40% of these patients experience rising prostate-specific antigen (PSA) levels after RP, indicating continued survival of prostate cells. A significant rise in PSA level after RP may be termed a "biochemical failure" (BF), "biochemical recurrence", or "biochemical relapse". At this point, a patient may opt for salvage radiation therapy (RT), adjuvant therapy, or both, depending on the prognosis from the clinician. For some patients, BF may occur again after the second round of therapy.

Currently, data used to develop prognoses after RP and RT include PSA levels, age, pathologic tumor (pT) and lymph node (pN) classification, and Gleason score. PSA is manufactured by cells of the prostate gland. A rising PSA level is considered a potential indicator of prostate cancer. Tumor stage (pT) indicates the size and invasiveness of the tumor (on a scale of 1-4, 1 being smallest and least invasive). The lymph node score (pN) indicates whether or not the cancer has spread to the lymph nodes near the prostate gland. This value is either a 0 if the cancer is not present in the lymph nodes, or a 1 if the cancer is found in the lymph nodes.

The Gleason score takes into account the ability of the tumor to form glands (an indication of healthier tissue). A pathologist assigns a primary grade based on the most prominent tissue seen in the tumor, and a secondary grade based on the second most prominent or the most aggressive types of tissue seen in the tumor. The range of grades is 1-5: 1, 2 and 3 are considered to be low to moderate in grade (many smaller, more uniform glands); 4 and 5 are considered to be high grade (few glands). The prognosis for a given patient generally falls somewhere between that predicted by the primary grade and a secondary grade given to the second most prominent glandular pattern. When the two grades are added the resulting number is referred to as the Gleason score. The Gleason Score is a more accurate predictor of outcome than either of the individual grades. Thus, the traditionally reported Gleason score will be the sum of two numbers between 1-5 with a total score from 2-10.

Multiple risk assessment nomograms and classification models have been derived utilizing parameters such as the pT, pN, Gleason score, or resection status. These models include the CAPRA score, Partin table, D'Amico classification, and the three Stephenson Nomograms. However, it is still difficult to distinguish between aggressive and indolent prostate cancers. The lack of clear predictors of prostate cancer progression leads to subjective decision-making regarding courses of treatment. Some prostate tumors grow so slowly that they never cause life threatening problems, making early-stage treatment controversial. Therefore, biomarkers that predict the progression of PCa are needed to guide therapy.

SUMMARY

Disclosed are methods of using miRNAs as molecular biomarkers to predict the progression of a patient's cancer and adjust their therapeutic regimen accordingly. Methods include predicting biochemical recurrence in a subject following radical prostatectomy. This may include determining a miRNA expression profile from a sample (e.g., tumor biopsy or bodily fluid) from the subject of at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 61, 62, 64, 65, 66, 67, 68, 69, 70, 71, 72, 73, 74, 75, 76, 77, 78, 79, 80, 81, 82, 83, 84, 85, 86, 87, or 88 of the miRNA listed in Table 2 and calculating a recurrence risk score from the miRNA expression profile. A high recurrence risk score can be an indication of biochemical recurrence within 1-5 years.

Methods also include predicting biochemical recurrence in a subject following post-prostatectomy salvage radiation therapy, including external beam radiation therapy or internal radiation therapy. This may include determining a miRNA expression profile from a sample from the subject of at least 1, 2, 3, 4, 5, 6, 7, 8, or 9 of the miRNA listed in Table 3 and calculating a recurrence risk score from the miRNA expression profile. In some embodiments, the miRNAs include miR-4516, miR-601, or a combination thereof, alone or in combination with any of the miRNAs listed in Table 3. A high recurrence risk score can be an indication of biochemical recurrence within 1-5 years.

Methods may also include grading the tumor biopsy according to a Gleason score, and using the Gleason score as a covariate in calculating the recurrence risk score. Methods may also include determining the lymph node classification, the pathologic tumor classification, and/or the resection status, and using these properties as covariates in calculating the recurrence risk score.

If the recurrence risk score is high, methods may include treating the subject with radical prostatectomy, radiation therapy, or adjuvant treatment. The adjuvant therapy may be chemotherapy, hormone therapy, biologic therapy, radiation therapy or a combination thereof. The radiation therapy may be salvage radiation therapy, including external beam radiation therapy or internal radiation therapy. Methods may also include treating a patient with palliative care if the recurrence risk score is high. If the recurrence risk score is low, treatment methods may include continued clinical monitoring.

Also disclosed are methods of using miRNA biomarkers to detect prostate cancer in a subject. In some embodiments, the method involves determining a miRNA expression profile from a sample from the subject that includes at least miRNA-1283, miRNA-137, or a combination thereof. This method may further include comparing the miRNA expression intensities to pre-specified levels and using these levels to reach a diagnosis. The step of reaching a diagnosis may also include determining a PSA level and/or taking a prostate biopsy. If the method detects prostate cancer, the method may further include administering a treatment such as surgical treatment, radiation treatment, adjuvant treatment, or a combination thereof.

For all methods, the sample used to detect or prognose prostate cancer may be a bodily fluid or a tumor.

In some embodiments, a kit may be used to determine an miRNA expression profile of a subject, the kit comprising oligonucleotide primers or probes configured to selectively bind to 2 or more miRNA listed in Table 1, Table 2, Table 3, or a combination thereof.

The details of one or more embodiments of the invention are set forth in the accompanying drawings and the description below. Other features, objects, and advantages of the invention will be apparent from the description and drawings, and from the claims.

DETAILED DESCRIPTION

Figure 1:
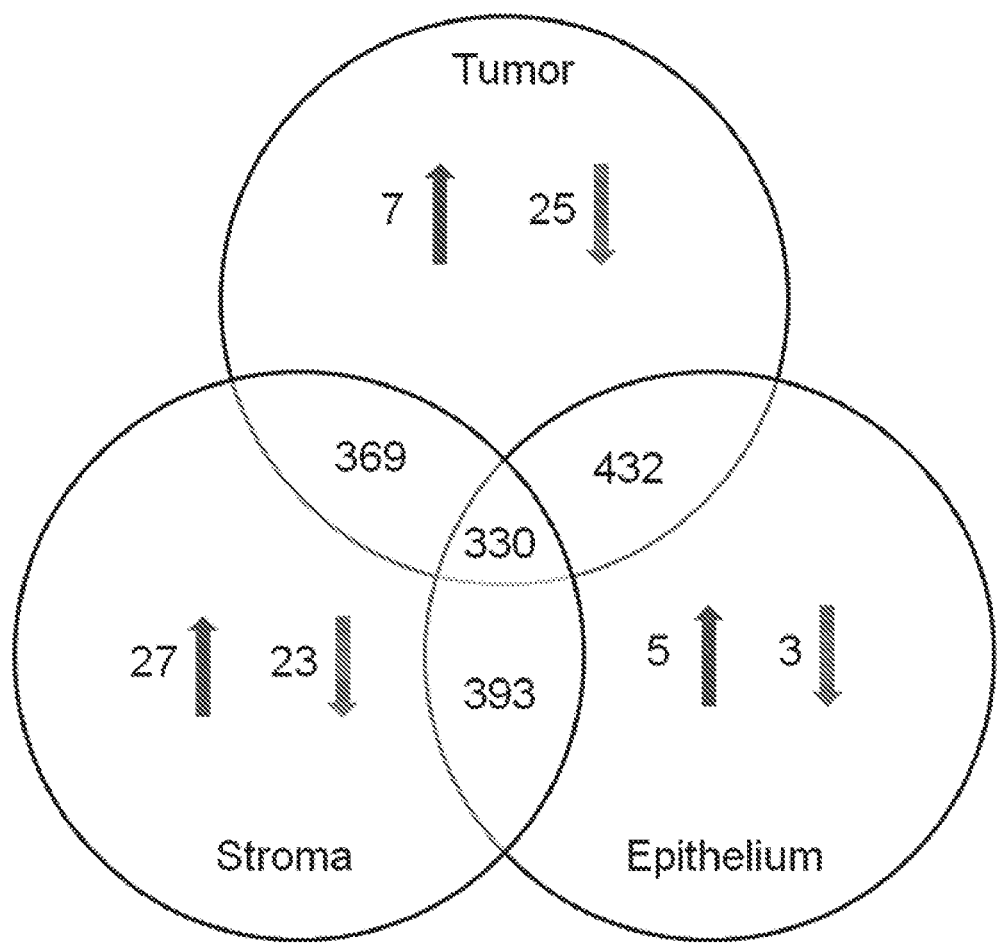
FIG. 1 shows a Venn diagram of the numbers of commonly and differentially expressed miRNAs in prostate tumor, stroma, and epithelium.

The lack of clear predictors of prostate cancer progression leads to subjective decision-making regarding courses of treatment. The identification of new biomarkers that can detect prostate cancer and predict recurrence post-RP would advance the field of PCa treatment. Disclosed herein are methods of using miRNAs as molecular biomarkers to detect and predict the progression of a patient's cancer and adjust their therapeutic regimen accordingly.

Disclosed are miRNA biomarkers which may be used to detect prostate cancer in a subject and/or predict its recurrence following therapy. The term "subject" refers to any individual who is the target of administration or treatment. The subject can be a vertebrate, for example, a mammal. Thus, the subject can be a human or veterinary patient. The term "patient" refers to a subject under the treatment of a clinician, e.g., physician.

In some embodiments, the biological sample used for determining the level of one or more miRNA biomarkers is a tumor sample containing miRNAs. The tumor sample may be freshly isolated or may have been preserved by methods known in the art, including but not limited to formalin fixation with paraffin embedding. In some embodiments, the biological sample used for determining the level of one or more miRNA biomarker is a tissue biopsy. In other embodiments, the biological sample contains circulating miRNAs, e.g., extracellular miRNAs. Circulating miRNAs include miRNAs in cells (cellular miRNA), extracellular miRNAs in microvesicles (microvesicle-associated miRNA), and extracellular miRNAs that are not associated with cells or microvesicles (extracellular, non-vesicular miRNA).

Extracellular miRNAs freely circulate in a wide range of bodily fluids. Accordingly, in some embodiments, the biological sample used for determining the level of one or more miRNA biomarkers is a bodily fluid, such as blood, fractions thereof, serum, plasma, urine, saliva, tears, sweat, semen, lymph, bronchial secretions, or CSF. In some embodiments, the sample is a sample that is obtained non-invasively. In some embodiments, the biological sample used for determining the level of one or more miRNA biomarkers may contain cells. In other embodiments, the biological sample may be free or substantially free of cells (e.g., a serum or plasma sample). The sample may likewise be free or substantially free of microvesicles. For example, a sample that is free or substantially free of microvesicles is one in which the microvesicle content of the sample is sufficiently low to avoid interfering with the ability to accurately determine the level of non-vesicular miRNAs in the sample.

The level of one or more miRNA biomarkers in a biological sample may be determined by any suitable method. Any reliable method for measuring the level or amount of miRNA in a sample may be used. Generally, miRNA can be detected and quantified from a sample (including fractions thereof), such as samples of isolated RNA by various methods known for mRNA detection, including, for example, amplification-based methods (e.g., Polymerase Chain Reaction (PCR), Real-Time Polymerase Chain Reaction (RT-PCR), Quantitative Polymerase Chain Reaction (qPCR), rolling circle amplification, etc.), hybridization-based methods (e.g., hybridization arrays (e.g., microarrays), NanoStringm analysis, Northern Blot analysis, branched DNA (bDNA) signal amplification, and in situ hybridization), and sequencing-based methods (e.g. next-generation sequencing methods, for example, using the Illumina or IonTorrent platforms). Other exemplary techniques include ribonuclease protection assay (RPA) and mass spectroscopy.

In some embodiments, RNA is converted to DNA (cDNA) prior to analysis. cDNA can be generated by reverse transcription of isolated miRNA using conventional techniques. miRNA reverse transcription kits are known and commercially available. Examples of suitable kits include, but are not limited to the mirVana TaqMan® miRNA transcription kit (Ambion, Austin, Tex.), and the TaqMan® miRNA transcription kit (Applied Biosystems, Foster City, Calif.). Universal primers, or specific primers, including miRNA-specific stem-loop primers, are known and commercially available, for example, from Applied Biosystems. In some embodiments, miRNA is amplified prior to measurement. In other embodiments, the level of miRNA is measured during the amplification process. In still other embodiments, the level of miRNA is not amplified prior to measurement. Some exemplary methods suitable for determining the level of miRNA in a sample are described in greater detail below. These methods are provided by way of illustration only, and it will be apparent to a skilled person that other suitable methods may likewise be used.

Many amplification-based methods exist for detecting the level of miRNA nucleic acid sequences, including, but not limited to, PCR, RT-PCR, qPCR, and rolling circle amplification. Other amplification-based techniques include, for example, ligase chain reaction, multiplex ligatable probe amplification, in vitro transcription (IVT), strand displacement amplification, transcription-mediated amplification, RNA (Eberwine) amplification, and other methods that are known to persons skilled in the art.

A typical PCR reaction includes multiple steps, or cycles, that selectively amplify target nucleic acid species: a denaturing step, in which a target nucleic acid is denatured; an annealing step, in which a set of PCR primers (i.e., forward and reverse primers) anneal to complementary DNA strands, and an elongation step, in which a thermostable DNA polymerase elongates the primers. By repeating these steps multiple times, a DNA fragment is amplified to produce an amplicon, corresponding to the target sequence. Typical PCR reactions include 20 or more cycles of denaturation, annealing, and elongation. In many cases, the annealing and elongation steps can be performed concurrently, in which case the cycle contains only two steps. A reverse transcription reaction (which produces a cDNA sequence having complementarity to a miRNA) may be performed prior to PCR amplification. Reverse transcription reactions include the use of, e.g., a RNA-based DNA polymerase (reverse transcriptase) and a primer. Kits for quantitative real time PCR of miRNA are known, and are commercially available. Examples of suitable kits include, but are not limited to, the TaqMan® miRNA Assay (Applied Biosystems) and the mirVana™ qRT-PCR miRNA detection kit (Ambion). The miRNA can be ligated to a single stranded oligonucleotide containing universal primer sequences, a polyadenylated sequence, or adaptor sequence prior to reverse transcriptase and amplified using a primer complementary to the universal primer sequence, poly(T) primer, or primer comprising a sequence that is complementary to the adaptor sequence.

In some instances, custom qRT-PCR assays can be developed for determination of miRNA levels. Custom qRT-PCR assays to measure miRNAs in a biological sample, e.g., a tumor or a bodily fluid, can be developed using, for example, methods that involve an extended reverse transcription primer and locked nucleic acid modified PCR. Custom miRNA assays can be tested by running the assay on a dilution series of chemically synthesized miRNA corresponding to the target sequence. This permits determination of the limit of detection and linear range of quantitation of each assay. Furthermore, when used as a standard curve, these data permit an estimate of the absolute abundance of miRNAs measured in biological samples.

Amplification curves may optionally be checked to verify that Ct values are assessed in the linear range of each amplification plot. Typically, the linear range spans several orders of magnitude. For each candidate miRNA assayed, a chemically synthesized version of the miRNA can be obtained and analyzed in a dilution series to determine the limit of sensitivity of the assay, and the linear range of quantitation. Relative expression levels may be determined, for example, according to the $2(-\Delta\Delta\ C(T))$ method.

In some embodiments, two or more miRNAs are amplified in a single reaction volume. For example, multiplex q-PCR, such as qRT-PCR, enables simultaneous amplification and quantification of at least two miRNAs of interest in one reaction volume by using more than one pair of primers and/or more than one probe. The primer pairs comprise at least one amplification primer that specifically binds each miRNA, and the probes are labeled such that they are distinguishable from one another, thus allowing simultaneous quantification of multiple miRNAs.

Rolling circle amplification is a DNA-polymerase driven reaction that can replicate circularized oligonucleotide probes with either linear or geometric kinetics under isothermal conditions. In the presence of two primers, one hybridizing to the (+) strand of DNA, and the other hybridizing to the (−) strand, a complex pattern of strand displacement results in the generation of over $10^9$ copies of each DNA molecule in 90 minutes or less. Tandemly linked copies of a closed circle DNA molecule may be formed by using a single primer. The process can also be performed using a matrix-associated DNA. The template used for rolling circle amplification may be reverse transcribed. This method can be used as a highly sensitive indicator of miRNA sequence and expression level at very low miRNA concentrations.

miRNA may also be detected using hybridization-based methods, including but not limited to hybridization arrays (e.g., microarrays), NanoString™ analysis, Northern Blot analysis, branched DNA (bDNA) signal amplification, and in situ hybridization.

Microarrays can be used to measure the expression levels of large numbers of miRNAs simultaneously. Microarrays can be fabricated using a variety of technologies, including printing with fine-pointed pins onto glass slides, photolithography using pre-made masks, photolithography using dynamic micromirror devices, ink-jet printing, or electrochemistry on microelectrode arrays. Also useful are microfluidic TaqMan Low-Density Arrays, which are based on an array of microfluidic qRT-PCR reactions, as well as related microfluidic qRT-PCR based methods.

In one example of microarray detection, various oligonucleotides (e.g., 200+ 5'-amino-modified-C6 oligos) corresponding to human sense miRNA sequences are spotted on three-dimensional CodeLink slides (GE Health/Amersham Biosciences) at a final concentration of about 20 μM and processed according to manufacturer's recommendations. First strand cDNA synthesized from 20 μg TRIzol-purified total RNA is labeled with biotinylated ddUTP using the Enzo BioArray end labeling kit (Enzo Life Sciences Inc.). Hybridization, staining, and washing can be performed according to a modified Affymetrix Antisense genome array protocol.

Axon B-4000 scanner and Gene-Pix Pro 4.0 software or other suitable software can be used to scan images. Non-positive spots after background subtraction, and outliers detected by the ESD procedure, are removed. The resulting signal intensity values may be normalized to per-chip median values and then used to obtain geometric means and standard errors for each miRNA. Each miRNA signal can be transformed to log base 2, and a one-sample t test can be conducted. Independent hybridizations for each sample can be performed on chips with each miRNA spotted multiple times to increase the robustness of the data.

Microarrays can be used for the expression profiling of miRNAs in diseases. For example, RNA can be extracted from a sample and, optionally, the miRNAs are size-selected from total RNA. Oligonucleotide linkers can be attached to the 5' and 3' ends of the miRNAs and the resulting ligation products are used as templates for an RT-PCR reaction. The sense strand PCR primer can have a fluorophore attached to its 5' end, thereby labeling the sense strand of the PCR product. The PCR product is denatured and then hybridized to the microarray. A PCR product, referred to as the target nucleic acid that is complementary to the corresponding miRNA capture probe sequence on the array will hybridize, via base pairing, to the spot at which the capture probes are affixed. The spot will then fluoresce when excited using a microarray laser scanner.

The fluorescence intensity of each spot is then evaluated in terms of the number of copies of a particular miRNA, using a number of positive and negative controls and array data normalization methods, which will result in assessment of the level of expression of a particular miRNA.

Total RNA containing the miRNA extracted from a sample can also be used directly without size-selection of the miRNAs. For example, the RNA can be 3' end labeled using T4 RNA ligase and a fluorophore-labeled short RNA linker. Fluorophore-labeled miRNAs complementary to the corresponding miRNA capture probe sequences on the array hybridize, via base pairing, to the spot at which the capture probes are affixed. The fluorescence intensity of each spot is then evaluated in terms of the number of copies of a particular miRNA, using a number of positive and negative controls and array data normalization methods, which will result in assessment of the level of expression of a particular miRNA.

Several types of microarrays can be employed including, but not limited to, spotted oligonucleotide microarrays, pre-fabricated oligonucleotide microarrays or spotted long oligonucleotide arrays.

miRNAs can also be detected without amplification using the nCounter® Analysis System (NanoString™ Technologies, Seattle, Wash.). This technology employs two nucleic acid-based probes that hybridize in solution (e.g., a reporter probe and a capture probe). After hybridization, excess probes are removed, and probe/target complexes are analyzed in accordance with the manufacturer's protocol. nCounter® miRNA assay kits are available from NanoString™ Technologies, which are capable of distinguishing between highly similar miRNAs with great specificity.

miRNAs can also be detected using branched DNA (bDNA) signal amplification (see, for example, Urdea, Nature Biotechnology (1994), 12:926-928). miRNA assays based on bDNA signal amplification are commercially available. One such assay is the QuantiGene® 2.0 miRNA Assay (Affymetrix, Santa Clara, Calif.).

Northern Blot and in situ hybridization may also be used to detect miRNAs. Suitable methods for performing Northern Blot and in situ hybridization are known in the art.

Advanced sequencing methods can likewise be used as available. For example, miRNAs can be detected using Illumina® Next Generation Sequencing (e.g., Sequencing-By-Synthesis or TruSeq methods, using, for example, the HiSeq, HiScan, GenomeAnalyzer, or MiSeq systems (Illumina, Inc., San Diego, Calif.)). miRNAs can also be detected using Ion Torrent Sequencing (Ion Torrent Systems, Inc., Gulliford, Conn.), or other suitable methods of semiconductor sequencing.

Mass spectroscopy can also be used to quantify miRNA using RNase mapping. Isolated RNAs can be enzymatically digested with RNA endonucleases (RNases) having high specificity (e.g., RNase TI, which cleaves at the 3'-side of all unmodified guanosine residues) prior to their analysis by MS or tandem MS (MS/MS) approaches. The first approach developed utilized the on-line chromatographic separation of endonuclease digests by reversed phase HPLC coupled directly to ESTMS. The presence of posttranscriptional modifications can be revealed by mass shifts from those expected based upon the RNA sequence. Ions of anomalous mass/charge values can then be isolated for tandem MS sequencing to locate the sequence placement of the post-transcriptionally modified nucleoside.

Matrix-assisted laser desorption/ionization mass spectrometry (MALDI-MS) has also been used as an analytical approach for obtaining information about post-transcriptionally modified nucleosides. MALDI-based approaches can be differentiated from EST-based approaches by the separation step. In MALDI-MS, the mass spectrometer is used to separate the miRNA.

To analyze a limited quantity of intact miRNAs, a system of capillary LC coupled with nanoESI-MS can be employed, by using a linear ion trap-orbitrap hybrid mass spectrometer (LTQ Orbitrap XL, Thermo Fisher Scientific) or a tandem-quadrupole time-of-flight mass spectrometer (QSTAR® XL, Applied Biosystems) equipped with a custom-made nanospray ion source, a Nanovolume Valve (Valco Instruments), and a splitless nano HPLC system (DiNa, KYA Technologies). Analyte/TEAA is loaded onto a nano-LC trap column, desalted, and then concentrated. Intact miRNAs are eluted from the trap column and directly injected into a CI 8 capillary column, and chromatographed by RP-HPLC using a gradient of solvents of increasing polarity. The chromatographic eluent is sprayed from a sprayer tip attached to the capillary column, using an ionization voltage that allows ions to be scanned in the negative polarity mode.

Additional methods for miRNA detection and measurement include, for example, strand invasion assay (Third Wave Technologies, Inc.), surface plasmon resonance (SPR), cDNA, MTDNA (metallic DNA; Advance Technologies, Saskatoon, SK), and single-molecule methods such as the one developed by US Genomics. Multiple miRNAs can be detected in a microarray format using a novel approach that combines a surface enzyme reaction with nanoparticle-amplified SPR imaging (SPRI). The surface reaction of poly(A) polymerase creates poly(A) tails on miRNAs hybridized onto locked nucleic acid (LNA) microarrays. DNA-modified nanoparticles are then adsorbed onto the poly(A) tails and detected with SPRI. This ultrasensitive nanoparticle-amplified SPRI methodology can be used for miRNA profiling at attamole levels.

In certain embodiments, labels, dyes, or labeled probes and/or primers are used to detect amplified or unamplified miRNAs. The skilled artisan will recognize which detection methods are appropriate based on the sensitivity of the detection method and the abundance of the target. Depending on the sensitivity of the detection method and the abundance of the target, amplification may or may not be required prior to detection. One skilled in the art will recognize the detection methods where miRNA amplification is preferred.

A probe or primer may include standard (A, T or U, G and C) bases, or modified bases. Modified bases include, but are not limited to, the AEGIS bases (from Eragen Biosciences). In certain aspects, bases are joined by a natural phosphodiester bond or a different chemical linkage. Different chemical linkages include, but are not limited to, a peptide bond or a Locked Nucleic Acid (LNA) linkage.

In a further aspect, oligonucleotide probes or primers present in an amplification reaction are suitable for monitoring the amount of amplification product produced as a function of time. In certain aspects, probes having different single stranded versus double stranded character are used to detect the nucleic acid. Probes include, but are not limited to, the 5'-exonuclease assay (e.g., TaqMan™) probes, stem-loop molecular beacons, stemless or linear beacons, peptide nucleic acid (PNA) Molecular Beacons, linear PNA beacons, non-FRET probes, Sunrise™/AmplifluorB™ probes, stem-loop and duplex Scorpion™ probes, bulge loop probes, pseudo knot probes, cyclicons, MGB Eclipse™ probe (Epoch Biosciences), hairpin probes, PNA light-up probes, anti-primer quench probes, self-assembled nanoparticle probes, and ferrocene-modified probes.

In certain embodiments, one or more of the primers in an amplification reaction can include a label. In yet further embodiments, different probes or primers comprise detectable labels that are distinguishable from one another. In some embodiments a nucleic acid, such as the probe or primer, may be labeled with two or more distinguishable labels. In some aspects, a label is attached to one or more probes and has one or more of the following properties: (i) provides a detectable signal; (ii) interacts with a second label to modify the detectable signal provided by the second label, e.g., FRET (Fluorescent Resonance Energy Transfer); (iii) stabilizes hybridization, e.g., duplex formation; and (iv) provides a member of a binding complex or affinity set, e.g., affinity, antibody-antigen, ionic complexes, hapten-ligand (e.g. biotin-avidin). In still other aspects, use of labels can be accomplished using any one of a large number of known techniques employing known labels, linkages, linking groups, reagents, reaction conditions, and analysis and purification methods.

miRNAs can be detected by direct or indirect methods. In a direct detection method, one or more miRNAs are detected by a detectable label that is linked to a nucleic acid molecule. In such methods, the miRNAs may be labeled prior to binding to the probe. Therefore, binding is detected by screening for the labeled miRNA that is bound to the probe. The probe is optionally linked to a bead in the reaction volume.

In certain embodiments, nucleic acids are detected by direct binding with a labeled probe, and the probe is subsequently detected. In one embodiment of the invention, the nucleic acids, such as amplified miRNAs, are detected using FlexMAP Microspheres (Luminex) conjugated with probes to capture the desired nucleic acids. Some methods may involve detection with polynucleotide probes modified with fluorescent labels or branched DNA (bDNA) detection, for example.

In other embodiments, nucleic acids are detected by indirect detection methods. For example, a biotinylated probe may be combined with a streptavidin-conjugated dye to detect the bound nucleic acid. The streptavidin molecule binds a biotin label on amplified miRNA, and the bound miRNA is detected by detecting the dye molecule attached to the streptavidin molecule. In one embodiment, the streptavidin-conjugated dye molecule comprises Phycolink® Streptavidin R-Phycoerythrin (PROzyme). Other conjugated dye molecules are known to persons skilled in the art.

Labels include, but are not limited to: light-emitting, light-scattering, and light-absorbing compounds which generate or quench a detectable fluorescent, chemiluminescent, or bioluminescent signal. A dual labeled fluorescent probe that includes a reporter fluorophore and a quencher fluorophore is used in some embodiments. It will be appreciated that pairs of fluorophores are chosen that have distinct emission spectra so that they can be easily distinguished.

In certain embodiments, labels are hybridization-stabilizing moieties which serve to enhance, stabilize, or influence hybridization of duplexes, e.g., intercalators and intercalating dyes (including, but not limited to, ethidium bromide and SYBR-Green), minor-groove binders, and cross-linking functional groups.

In other embodiments, methods relying on hybridization and/or ligation to quantify miRNAs may be used, including oligonucleotide ligation (OLA) methods and methods that allow a distinguishable probe that hybridizes to the target nucleic acid sequence to be separated from an unbound probe. As an example, HARP-like probes may be used to measure the quantity of miRNAs. In such methods, after hybridization between a probe and the targeted nucleic acid, the probe is modified to distinguish the hybridized probe from the unhybridized probe. Thereafter, the probe may be amplified and/or detected. In general, a probe inactivation region comprises a subset of nucleotides within the target hybridization region of the probe. To reduce or prevent amplification or detection of a HARP probe that is not hybridized to its target nucleic acid, and thus allow detection of the target nucleic acid, a post-hybridization probe inactivation step is carried out using an agent which is able to distinguish between a HARP probe that is hybridized to its targeted nucleic acid sequence and the corresponding unhybridized HARP probe. The agent is able to inactivate or modify the unhybridized HARP probe such that it cannot be amplified.

A probe ligation reaction may also be used to quantify miRNAs. In a Multiplex Ligation-dependent Probe Amplification (MLPA) technique, pairs of probes which hybridize immediately adjacent to each other on the target nucleic acid are ligated to each other driven by the presence of the target nucleic acid. In some aspects, MLPA probes have flanking PCR primer binding sites. MLPA probes are specifically amplified when ligated, thus allowing for detection and quantification of miRNA biomarkers.

An miRNA expression profile may be calculated based on a sample from a subject. In some embodiments, the miRNA expression profile may be used to diagnosis prostate cancer and to evaluate its aggressiveness. In some implementations, a subject's miRNA expression profile may be used to predict biochemical recurrence after a first treatment for prostate cancer. For example, the profile may be used to predict recurrence after radical prostatectomy. In another implementation, a subject's miRNA expression profile may be used to predict biochemical recurrence after a second treatment for prostate cancer. For example, the profile may be used to predict recurrence after salvage radiation therapy. In other embodiments, an miRNA expression profile may be used to evaluate the effectiveness of a prostate cancer treatment regimen.

For example, in some embodiments, the profile includes miRNA-137, miRNA-1283, or a combination thereof. In some embodiments, the profile includes at least 1, 2, 3, 4, 5, 6, 7, 8, 9, 10, or 11 of the miRNAs listed in Table 1. As disclosed herein, these miRNAs are deregulated in prostate cancer and may be used to diagnose prostate cancer. In particular, hsa-miR-205-5p, hsa-miR-1283, hsa-miR-221-3p, hsa-miR-222-3p, hsa-miR-145-5p, hsa-miR-1253, hsa-miR-133a, hsa-miR-1, and hsa-miR-143-3p may be differentially expressed at least two-fold less in prostate cancer cells compared to epithelial cells; while hsa-miR-137 and hsa-miR-375 may be differentially expressed at least two-fold higher in prostate cancer cells compared to epithelial cells. In some embodiments, the method further comprises treating a subject having a profile indicative of prostate cancer. Treatment may include a biopsy to confirm the existence and aggressiveness of prostate cancer tumor.

TABLE 1

Eleven miRNAs differentially regulated in prostate tumor tissue as compared to the surrounding epithelial tissue.

| miRNA ID | ratio: tumor versus epithelium | p-value: tumor versus epithelium |
|---|---|---|
| hsa-miR-205-5p | 5.0 ↓ | 0.0002 |
| hsa-miR-1283 | 3.3 ↓ | 0.0024 |
| hsa-miR-221-3p | 3.3 ↓ | <.0001 |
| hsa-miR-222-3p | 2.5 ↓ | <.0001 |
| hsa-miR-145-5p | 2.5 ↓ | 0.0002 |
| hsa-miR-1253 | 2.5 ↓ | 0.0015 |
| hsa-miR-133a | 2.0 ↓ | <.0001 |
| hsa-miR-1 | 2.0 ↓ | <.0001 |
| hsa-miR-1 | 2.0 ↓ | 0.0006 |
| hsa-miR-137 | 2.1 ↑ | 0.0173 |
| hsa-miR-375 | 2.4 ↑ | <.0001 |

One example implementation includes a method of using an miRNA expression profile to predict biochemical recurrence after radical prostatectomy. The profile may include at least one of the miRNAs listed in Table 2 including at least 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 64, 65, 66, 67, 68, 69, 70, 71, 72, 73, 74, 75, 76, 77, 78, 79, 80, 81, 82, 83, 84, 85, 86, 87, or 88 of the miRNAs listed in Table 2. The miRNA expression profile may be used to calculate a recurrence risk score. In some cases, the recurrence risk score may be an indication of how soon recurrence will occur. A higher risk score may indicate that recurrence will occur at an earlier date than a lower risk score. A high recurrence risk may indicate a recurrence within 1-5 years after radical prostatectomy. In other implementations, a high recurrence risk indicates a recurrence within 2-4 years after the treatment. In still other implementations, a high recurrence risk indicates a recurrence within 36 months after radical prostatectomy. If a subject is found to have a high recurrence risk score, subsequent treatment options might include radiation therapy, adjuvant therapy, or in some cases, palliative care. If a subject is found to have a low recurrence risk score, subsequent treatment options may include continued clinical monitoring without radiation or adjuvant therapy.

TABLE 2 miRNAs that predict biochemical recurrence post-radical prostatectomy (RP) via multivariate Cox-regression analysis

| miR_ID | D'Amico nomogram | | | Stephensen nomogram (categorical) | | | Stephensen nomogram (continuous) | | |
|---|---|---|---|---|---|---|---|---|---|
| | Hazard Ratio | p-value | Confidence Interval | Hazard Ratio | p-value | Confidence Interval | Hazard Ratio | p-value | Confidence Interval |
| hsa-miR-107 | 3.69 | 0.0002 | (1.9, 7.3) | 3.42 | 0.0005 | (1.7, 6.9) | 3.37 | 0.0006 | (1.7, 6.7) |
| hsa-miR-98 | 3.49 | 0.0003 | (1.8, 6.9) | 2.37 | 0.0086 | (1.2, 4.5) | 2.44 | 0.0059 | (1.3, 4.6) |
| hsa-let-7a-5p | 3.24 | 0.0006 | (1.7, 6.4) | 2.18 | 0.0188 | (1.1, 4.2) | 2.23 | 0.0156 | (1.2, 4.3) |
| hsa-miR-324-5p | 3.03 | 0.0008 | (1.6, 5.8) | 3.08 | 0.0007 | (1.6, 5.9) | 2.92 | 0.0011 | (1.5, 5.6) |
| hsa-miR-1060-5p | 3.02 | 0.0031 | (1.5, 6.3) | 2.95 | 0.005 | (1.4, 6.3) | 3.04 | 0.004 | (1.4, 6.5) |
| hsa-let-7f-5p | 3.01 | 0.0013 | (1.5, 5.9) | 3.03 | 0.0017 | (1.5, 6.1) | 3.13 | 0.0011 | (1.6, 6.2) |
| hsa-let-7e-5p | 3 | 0.0009 | (1.6, 5.7) | 2.22 | 0.044 | (1.2, 4.2) | 2.27 | 0.0106 | (1.2, 4.3) |
| hsa-miR-28-5p | 2.97 | 0.0011 | (1.5, 5.7) | 2.5 | 0.0054 | (1.3, 4.8) | 2.51 | 0.0058 | (1.3, 4.8) |
| hsa-miR-29c-3p | 2.94 | 0.0014 | (1.5, 5.7) | 3.04 | 0.0014 | (1.5, 6) | 2.86 | 0.0023 | (1.5, 5.6) |
| hsa-let-7g-5p | 2.94 | 0.0016 | (1.5, 5.7) | 2.2 | 0.0162 | (1.2, 4.2) | 2.22 | 0.0136 | (1.2, 4.2) |
| hsa-miR-148a-3p | 2.9 | 0.0032 | (1.4, 5.9) | 2.69 | 0.0071 | (1.3, 5.5) | 2.88 | 0.0036 | (1.4, 5.9) |
| hsa-miR-18b-5p | 2.78 | 0.0025 | (1.4, 5.4) | 4.23 | 0.0001 | (2.1, 8.7) | 4.02 | 0.0002 | (1.9, 8.4) |
| hsa-miR-15a-5p | 2.76 | 0.003 | (1.4, 5.4) | 2.88 | 0.0026 | (1.4, 5.7) | 2.91 | 0.0022 | (1.5, 5.8) |
| hsa-miR-106a-5p + miR-17-5p | 2.72 | 0.007 | (1.3, 5.6) | 2.79 | 0.0065 | (1.3, 5.8) | 2.69 | 0.0084 | (1.3, 5.6) |
| hsa-miR-365a-3p | 2.7 | 0.0055 | (1.3, 5.4) | 2.93 | 0.0027 | (1.5, 5.9) | 3.14 | 0.0013 | (1.6, 6.3) |
| hsa-miR-194-5p | 2.68 | 0.0091 | (1.3, 5.6) | 2.49 | 0.0226 | (1.1, 5.4) | 2.52 | 0.0177 | (1.2, 5.4) |
| hsa-miR-4454 | 2.67 | 0.0061 | (1.3, 5.4) | 2.73 | 0.0057 | (1.3, 5.6) | 2.7 | 0.0059 | (1.3, 5.5) |
| hsa-miR-191-5p | 2.67 | 0.004 | (1.4, 5.2) | 2.55 | 0.0079 | (1.3, 5.1) | 2.65 | 0.0051 | (1.3, 5.2) |
| hsa-miR-141-3p | 2.64 | 0.007 | (1.3, 5.3) | 2.68 | 0.0071 | (1.3, 5.5) | 2.74 | 0.0055 | (1.3, 5.6) |
| hsa-miR-548aa | 2.62 | 0.0048 | (1.3, 5.1) | 2.86 | 0.0063 | (1.3, 6.1) | 2.62 | 0.0069 | (1.3, 5.3) |
| hsa-miR-497-5p | 2.61 | 0.0035 | (1.4, 5) | 2.2 | 0.0146 | (1.2, 4.1) | 2.12 | 0.0185 | (1.1, 4) |
| hsa-miR-30c-5p | 2.6 | 0.0035 | (1.4, 4.9) | 2.89 | 0.0014 | (1.5, 5.5) | 2.68 | 0.0025 | (1.4, 5.1) |
| hsa-miR-4448 | 2.58 | 0.0052 | (1.3, 5) | 2.6 | 0.0052 | (1.3, 5.1) | 2.35 | 0.0107 | (1.2, 4.5) |
| hsa-miR-548v | 2.56 | 0.0074 | (1.3, 5.1) | 2.29 | 0.0158 | (1.2, 4.5) | 2.38 | 0.0129 | (1.2, 4.7) |
| hsa-miR-148b-3p | 2.52 | 0.0087 | (1.3, 5) | 2.7 | 0.0063 | (1.3, 5.5) | 2.61 | 0.0079 | (1.3, 5.3) |
| hsa-miR-1260b | 2.51 | 0.0072 | (1.3, 4.9) | 2.49 | 0.0158 | (1.2, 5.2) | 2.49 | 0.0109 | (1.2, 5) |
| hsa-miR-375 | 2.5 | 0.0093 | (1.3, 5) | 2.22 | 0.038 | (1, 4.7) | 2.33 | 0.0262 | (1.1, 4.9) |
| hsa-miR-221-3p | 2.5 | 0.0052 | (1.3, 4.8) | 2.63 | 0.0036 | (1.4, 5) | 2.65 | 0.0041 | (1.4, 5.2) |
| hsa-miR-423-5p | 2.5 | 0.0101 | (1.2, 5) | 2.65 | 0.0073 | (1.3, 5.4) | 2.77 | 0.0044 | (1.4, 5.6) |
| hsa-miR-195-5p | 2.46 | 0.005 | (1.3, 4.6) | 2.06 | 0.0251 | (1.1, 3.9) | 2.04 | 0.0242 | (1.1, 3.8) |
| hsa-miR-27b-3p | 2.42 | 0.0067 | (1.3, 4.6) | 2.13 | 0.019 | (1.1, 4) | 2.03 | 0.026 | (1.1, 3.8) |
| hsa-miR-483-3p | 2.42 | 0.0143 | (1.2, 4.9) | 2.33 | 0.0278 | (1.1, 5) | 2.4 | 0.0191 | (1.2, 5) |
| hsa-miR-193a-5p | 2.4 | 0.0101 | (1.2, 4.7) | 3.49 | 0.0006 | (1.7, 7.1) | 3.77 | 0.0004 | (1.8, 7.9) |
| hsa-miR-660-5p | 2.38 | 0.0104 | (1.2, 4.6) | 3.39 | 0.001 | (1.6, 7) | 2.92 | 0.002 | (1.5, 5.7) |
| hsa-miR-374b-5p | 2.37 | 0.0073 | (1.3, 4.5) | 1.96 | 0.0365 | (1, 3.7) | 1.93 | 0.037 | (1, 3.6) |
| hsa-miR-1206 | 2.36 | 0.0145 | (1.2, 4.7) | 2.29 | 0.0234 | (1.1, 4.7) | 2.33 | 0.0184 | (1.2, 4.7) |
| hsa-miR-30b-5p | 2.32 | 0.0169 | (1.2, 4.6) | 3.64 | 0.0008 | (1.7, 7.7) | 3.03 | 0.0021 | (1.5, 6.1) |
| hsa-let-7d-5p | 2.31 | 0.0089 | (1.2, 4.3) | 1.91 | 0.0438 | (1, 3.6) | 1.95 | 0.0354 | (1, 3.6) |
| hsa-miR-135a-5p | 2.3 | 0.012 | (1.2, 4.4) | 2.03 | 0.0281 | (1.1, 3.8) | 2.15 | 0.0165 | (1.2, 4) |
| hsa-miR-24-3p | 2.3 | 0.0095 | (1.2, 4.3) | 2.05 | 0.0238 | (1.1, 3.8) | 1.98 | 0.0307 | (1.1, 3.7) |
| hsa-miR-199a-3p + miR-199b | 2.28 | 0.0101 | (1.2, 4.3) | 1.93 | 0.04 | (1, 3.6) | 1.94 | 0.0366 | (1, 3.6) |

TABLE 2-continued miRNAs that predict biochemical recurrence post-radical prostatectomy (RP) via multivariate Cox-regression analysis

| miR_ID | D'Amico nomogram | | | Stephensen nomogram (categorical) | | | Stephensen nomogram (continuous) | | |
|---|---|---|---|---|---|---|---|---|---|
| | Hazard Ratio | p-value | Confidence Interval | Hazard Ratio | p-value | Confidence Interval | Hazard Ratio | p-value | Confidence Interval |
| hsa-miR-130a-3p | 2.15 | 0.0164 | (1.2, 4) | 2.03 | 0.0288 | (1.1, 3.8) | 2.04 | 0.0254 | (1.1, 3.8) |
| hsa-miR-1915-3p | 2.15 | 0.02 | (1.1, 4.1) | 2.46 | 0.0091 | (1.3, 4.8) | 2.12 | 0.0237 | (1.1, 4) |
| hsa-miR-99b-5p | 2.15 | 0.0198 | (1.1, 4.1) | 2.06 | 0.0305 | (1.1, 4) | 1.88 | 0.0479 | (1, 3.5) |
| hsa-miR-93-5p | 2.11 | 0.0315 | (1.1, 4.2) | 2.68 | 0.0049 | (1.3, 5.3) | 2.45 | 0.0099 | (1.2, 4.8) |
| hsa-miR-30d-5p | 2.1 | 0.0229 | (1.1, 4) | 2.35 | 0.0119 | (1.2, 4.6) | 2.36 | 0.008 | (1.3, 4.4) |
| hsa-miR-15b-5p | 2.05 | 0.0347 | (1.1, 4) | 2.38 | 0.0132 | (1.2, 4.7) | 2.25 | 0.0178 | (1.2, 4.4) |
| hsa-miR-23b-3p | 2 | 0.0303 | (1.1, 3.7) | 2 | 0.0318 | (1.1, 3.7) | 2.01 | 0.0286 | (1.1, 3.7) |
| hsa-miR-421 | 1.95 | 0.0393 | (1, 3.7) | 1.98 | 0.0393 | (1, 3.8) | 2.06 | 0.0265 | (1.1, 3.9) |
| hsa-miR-145-5p | 1.88 | 0.0462 | (1, 3.5) | 2.49 | 0.0059 | (1.3, 4.8) | 2.49 | 0.0069 | (1.3, 4.8) |
| hsa-miR-548t-5p | 0.53 | 0.0449 | (0.3, 1) | 0.35 | 0.0026 | (0.2, 0.7) | 0.39 | 0.0049 | (0.2, 0.8) |
| hsa-miR-1180 | 0.52 | 0.0464 | (0.3, 1) | 0.35 | 0.0028 | (0.2, 0.7) | 0.36 | 0.0044 | (0.2, 0.7) |
| hsa-miR-515-3p | 0.52 | 0.0471 | (0.3, 1) | 0.51 | 0.0437 | (0.3, 1) | 0.5 | 0.0334 | (0.3, 0.9) |
| hsa-miR-508-5p | 0.51 | 0.0365 | (0.3, 1) | 0.31 | 0.0012 | (0.2, 0.6) | 0.35 | 0.0021 | (0.2, 0.7) |
| hsa-miR-513a-3p | 0.51 | 0.0428 | (0.3, 1) | 0.39 | 0.0064 | (0.2, 0.8) | 0.45 | 0.0169 | (0.2, 0.9) |
| hsa-miR-566 | 0.51 | 0.031 | (0.3, 0.9) | 0.42 | 0.013 | (0.2, 0.8) | 0.5 | 0.0282 | (0.3, 0.9) |
| hsa-miR-613 | 0.5 | 0.0363 | (0.3, 1) | 0.39 | 0.0059 | (0.2, 0.8) | 0.41 | 0.0088 | (0.2, 0.8) |
| hsa-miR-1200 | 0.5 | 0.0353 | (0.3, 1) | 0.38 | 0.0041 | (0.2, 0.7) | 0.35 | 0.0027 | (0.2, 0.7) |
| hsa-miR-762 | 0.49 | 0.0323 | (0.3, 0.9) | 0.3 | 0.001 | (0.2, 0.6) | 0.33 | 0.0021 | (0.2, 0.7) |
| hsa-miR-450b-3p | 0.49 | 0.0324 | (0.2, 0.9) | 0.42 | 0.0113 | (0.2, 0.8) | 0.44 | 0.0149 | (0.2, 0.9) |
| hsa-miR-1205 | 0.48 | 0.021 | (0.3, 0.9) | 0.42 | 0.0139 | (0.2, 0.8) | 0.45 | 0.0136 | (0.2, 0.9) |
| hsa-miR-3168 | 0.48 | 0.0212 | (0.3, 0.9) | 0.38 | 0.0059 | (0.2, 0.8) | 0.4 | 0.0064 | (0.2, 0.8) |
| hsa-miR-548d-5p | 0.47 | 0.0471 | (0.2, 1) | 0.45 | 0.0327 | (0.2, 0.9) | 0.41 | 0.0189 | (0.2, 0.9) |
| hsa-miR-320a | 0.47 | 0.0271 | (0.2, 0.9) | 0.41 | 0.0095 | (0.2, 0.8) | 0.41 | 0.01 | (0.2, 0.8) |
| hsa-miR-3136-5p | 0.47 | 0.0231 | (0.2, 0.9) | 0.47 | 0.0266 | (0.2, 0.9) | 0.45 | 0.0173 | (0.2, 0.9) |
| hsa-miR-3934 | 0.47 | 0.0166 | (0.2, 0.9) | 0.41 | 0.0058 | (0.2, 0.8) | 0.37 | 0.003 | (0.2, 0.7) |
| hsa-miR-409-3p | 0.45 | 0.019 | (0.2, 0.9) | 0.41 | 0.01 | (0.2, 0.8) | 0.34 | 0.0032 | (0.2, 0.7) |
| hsa-miR-516a-3p | 0.45 | 0.0216 | (0.2, 0.9) | 0.4 | 0.0089 | (0.2, 0.8) | 0.4 | 0.0074 | (0.2, 0.8) |
| hsa-miR-1288 | 0.45 | 0.0128 | (0.2, 0.8) | 0.5 | 0.034 | (0.3, 0.9) | 0.49 | 0.0282 | (0.3, 0.9) |
| hsa-miR-541-3p | 0.44 | 0.0108 | (0.2, 0.8) | 0.41 | 0.006 | (0.2, 0.8) | 0.44 | 0.0101 | (0.2, 0.8) |
| hsa-miR-1257 | 0.44 | 0.025 | (0.2, 0.9) | 0.27 | 0.0005 | (0.1, 0.6) | 0.25 | 0.0005 | (0.1, 0.5) |
| hsa-miR-548ak | 0.44 | 0.0139 | (0.2, 0.8) | 0.26 | 0.0003 | (0.1, 0.5) | 0.27 | 0.0004 | (0.1, 0.6) |
| hsa-miR-1323 | 0.44 | 0.0171 | (0.2, 0.9) | 0.45 | 0.02 | (0.2, 0.9) | 0.45 | 0.0232 | (0.2, 0.9) |
| hsa-miR-216a | 0.41 | 0.0076 | (0.2, 0.8) | 0.24 | 0.0002 | (0.1, 0.5) | 0.34 | 0.0018 | (0.2, 0.7) |
| hsa-miR-922 | 0.41 | 0.0097 | (0.2, 0.8) | 0.3 | 0.0006 | (0.1, 0.6) | 0.32 | 0.0011 | (0.2, 0.6) |
| hsa-miR-302a-3p | 0.41 | 0.0067 | (0.2, 0.8) | 0.36 | 0.0053 | (0.2, 0.7) | 0.39 | 0.0041 | (0.2, 0.7) |
| hsa-miR-1276 | 0.4 | 0.011 | (0.2, 0.8) | 0.35 | 0.0045 | (0.2, 0.7) | 0.35 | 0.0033 | (0.2, 0.7) |
| hsa-miR-34c-3p | 0.4 | 0.0046 | (0.2, 0.8) | 0.36 | 0.0028 | (0.2, 0.7) | 0.4 | 0.0046 | (0.2, 0.8) |
| hsa-miR-572 | 0.39 | 0.0048 | (0.2, 0.8) | 0.25 | 0.0003 | (0.1, 0.5) | 0.35 | 0.0014 | (0.2, 0.7) |
| hsa-miR-1908 | 0.36 | 0.0029 | (0.2, 0.7) | 0.4 | 0.0098 | (0.2, 0.8) | 0.39 | 0.0067 | (0.2, 0.8) |
| hsa-miR-568 | 0.35 | 0.0026 | (0.2, 0.7) | 0.25 | 0.0001 | (0.1, 0.5) | 0.28 | 0.0003 | (0.1, 0.6) |
| hsa-miR-576-3p | 0.35 | 0.0028 | (0.2, 0.7) | 0.27 | 0.0002 | (0.1, 0.5) | 0.28 | 0.0002 | (0.1, 0.5) |
| hsa-miR-486-3p | 0.34 | 0.002 | (0.2, 0.7) | 0.28 | 0.0004 | (0.1, 0.6) | 0.29 | 0.0004 | (0.1, 0.6) |
| hsa-miR-638 | 0.33 | 0.001 | (0.2, 0.6) | 0.31 | 0.0005 | (0.2, 0.6) | 0.32 | 0.0007 | (0.2, 0.6) |
| hsa-miR-885-5p | 0.31 | 0.0007 | (0.2, 0.6) | 0.44 | 0.0122 | (0.2, 0.8) | 0.42 | 0.007 | (0.2, 0.8) |
| hsa-miR-1286 | 0.31 | 0.0013 | (0.1, 0.6) | 0.33 | 0.0047 | (0.2, 0.7) | 0.3 | 0.0016 | (0.1, 0.6) |
| hsa-miR-450b-5p | 0.28 | 0.0005 | (0.1, 0.6) | 0.33 | 0.0019 | (0.2, 0.7) | 0.31 | 0.001 | (0.2, 0.6) |
| hsa-miR-890 | 0.25 | 0.0001 | (0.1, 0.5) | 0.27 | 0.0006 | (0.1, 0.6) | 0.34 | 0.0025 | (0.2, 0.7) |

Another exemplary implementation includes a method of using a miRNA expression profile to predict biochemical recurrence after radiation therapy, such as salvage radiation therapy. The profile may include at least one of the miRNAs listed in Table 3, including at least 1, 2, 3, 4, 5, 6, 7, 8, or 9 of the miRNAs listed in Table 3. In some embodiments, the profile may include at least miRNA-601 and miRNA-4516. The profile may be used alone or in conjunction with other prognostic parameters to calculate the recurrence risk score after radiation therapy. For example, the profile may be used in combination with the subject's age, Gleason score, tumor stage (pT), lymph node score (pN), PSA levels, resection status, D'Amico classification, Stephenson nomograms, or any combination thereof to calculate the recurrent risk score.

In some cases, the recurrence risk score may be an indication of how soon recurrence may occur. For example, a high recurrence risk may indicate a recurrence within 1-5 years after radiation therapy. In other implementations, a high recurrence risk indicates a recurrence within 2-4 years after the treatment. In still other implementations, a high recurrence risk indicates a recurrence within 36 months after radiation therapy. If a subject is found to have a high recurrence risk score, subsequent treatment options might include radical prostatectomy, adjuvant therapy, or in some cases, palliative care. If a subject is found to have a low recurrence risk score, subsequent treatment options might include continued clinical monitoring without radical prostatectomy or radical prostatectomy with clinical monitoring.

TABLE 3

Nine miRNAs predictive of biochemical recurrence after salvage radiation therapy.

| miRNA ID | hazard ratio (high versus low) | p-value | Confidence interval |
|---|---|---|---|
| hsa-miR-628-3p | 6.6 | 0.0036 | 1.9-23.5 |
| hsa-miR-1193 | 5 | 0.0064 | 1.6-15.6 |
| hsa-miR-601 | 4.6 | 0.0037 | 1.6-12.7 |
| hsa-miR-4516 | 3.6 | 0.0128 | 1.3-10 |
| hsa-miR-320e | 3.2 | 0.0339 | 1.1-9.6 |
| hsa-miR-508-3p | 3 | 0.0296 | 1.1-8 |
| hsa-miR-598 | 0.3 | 0.0304 | 0.1-0.9 |
| hsa-miR-626 | 0.3 | 0.0391 | 0.1-0.9 |
| hsa-miR-563 | 0.3 | 0.0228 | 0.1-0.8 |

Recurrence risk scores after radical prostatectomy or radiation therapy or can be calculated using standard mathematical methods, models, and algorithms. In some embodiments, the risk score is a regression value, e.g., where a regression value of about 1 is an indication of recurrence. For example, the miRNA profile may be analyzed by multivariate regression analysis (e.g., determined by linear regression), a Cox regression model, or principal component analysis to derive a risk score. In other implementations, the miRNA profile or levels of specific miRNA biomarkers may be used in conjunction with other factors (for example, age, PSA levels, pathologic tumor (pT) and lymph node (pN) classification, Gleason score, resection status, D'Amico classification, and/or Stephenson nomograms) to calculate a recurrence risk score. For example, the miRNA profile may be used with other factors to create nomograms for predicting the recurrence risk score. In still other implementations, specific miRNA biomarkers are used to calculate the recurrence risk score. For example, in some embodiments, levels of miRNA relative to control values are negatively/positively correlated to risk score.

In some embodiments, miRNA panels contain numerous data points that are best managed and stored in a computer readable form. Therefore, in preferred embodiments, the risk score is a regression value derived from the miRNA panels as a weighted function of the quantified miRNA. The weighted function can be derived from linear regression analysis of experimental results comparing miRNA of normal subjects versus those with prostate cancer and/or biochemical recurrence. Each miRNA species can be multiplied by a weighting constant and summed.

Generally speaking, a regression value is a single value that is sensitive to changes in abundance of miRNA species of a miRNA profile, with a regression value of about 1 being indicative of a high risk of recurrence. For example, a regression value of about 0 can be indicative of low risk of recurrence, while a regression value of about 0.4, 0.5, 0.6, 0.7, 0.8, 0.9, 1, and more may be indicative of high risk of recurrence Prior to analysis, the data in each dataset can be collected by measuring the values for each miRNA biomarker, usually in duplicate or triplicate or in multiple replicates. The data may be manipulated, for example raw data may be transformed using standard curves, and the average of replicate measurements used to calculate the average and standard deviation for each patient. These values may be transformed before being used in the models, e.g. log-transformed, Box-Cox transformed, etc. This data can then be input into an analytical process with defined parameter.

The analytic classification process may be any type of learning algorithm with defined parameters, or in other words, a predictive model. In general, the analytical process will be in the form of a model generated by a statistical analytical method such as those described below. Examples of such analytical processes may include a linear algorithm, a quadratic algorithm, a polynomial algorithm, a decision tree algorithm, or a voting algorithm. Using any suitable learning algorithm, an appropriate reference or training dataset can be used to determine the parameters of the analytical process to be used for classification, i.e., develop a predictive model. The reference or training dataset to be used will depend on the desired classification to be determined. The dataset may include data from two, three, four or more classes.

The number of features that may be used by an analytical process to classify a test subject with adequate certainty is 2 or more. In some embodiments, it is 3 or more, 4 or more, 10 or more, or between 10 and 200. Depending on the degree of certainty sought, however, the number of features used in an analytical process can be more or less, but in all cases is at least 2. In one embodiment, the number of features that may be used by an analytical process to classify a test subject is optimized to allow a classification of a test subject with high certainty.

Suitable data analysis algorithms are known in the art. In one embodiment, a data analysis algorithm of the disclosure comprises Classification and Regression Tree (CART), Multiple Additive Regression Tree (MART), Prediction Analysis for Microarrays (PAM), or Random Forest analysis. Such algorithms classify complex spectra from biological materials, such as a blood sample, to distinguish subjects as normal or as possessing biomarker levels characteristic of a particular condition (e.g., biochemical recurrence). In other embodiments, a data analysis algorithm of the disclosure comprises ANOVA and nonparametric equivalents, linear discriminant analysis, logistic regression analysis, nearest neighbor classifier analysis, neural networks, principal component analysis, hierarchical cluster analysis, quadratic discriminant analysis, regression classifiers and support vector machines.

As will be appreciated by those of skill in the art, a number of quantitative criteria can be used to communicate the performance of the comparisons made between a test marker profile and reference marker profiles. These include area under the curve (AUC), hazard ratio (HR), relative risk (RR), reclassification, positive predictive value (PPV), negative predictive value (NPV), accuracy, sensitivity and specificity, Net reclassification Index, Clinical Net reclassification Index. In addition, other constructs such a receiver operator curves (ROC) can be used to evaluate analytical process performance.

The predicted risk of recurrence can be used to select an appropriate therapy and further treat the subject. The term "treatment" refers to the medical management of a patient with the intent to cure, ameliorate, stabilize, or prevent a disease, pathological condition, or disorder. This term includes active treatment, that is, treatment directed specifically toward the improvement of a disease, pathological condition, or disorder, and also includes causal treatment, that is, treatment directed toward removal of the cause of the associated disease, pathological condition, or disorder. In addition, this term includes palliative treatment, that is, treatment designed for the relief of symptoms rather than the curing of the disease, pathological condition, or disorder; preventative treatment, that is, treatment directed to minimizing or partially or completely inhibiting the development of the associated disease, pathological condition, or disorder; and supportive treatment, that is, treatment employed to supplement another specific therapy directed toward the improvement of the associated disease, pathological condition, or disorder. The term "treatment" therefore includes clinical intervention to alter or prevent the development or spread of prostate cancer. Treatment may include surgical approaches, radiation therapies, adjuvant therapies, or ultrasound treatments, alone or in any combination. Surgical therapies or treatments may include cryosurgery, orchiectomy, or prostatectomy. Prostatectomy may include removal of part or all of the prostate gland. Radical prostatectomy includes removal of all of the prostate gland, the seminal vesicles, the nearby tissue, and the nearby lymph nodes. The method of prostatectomy may be retropubic, suprapubic, perineal, minimally-invasive, nerve-sparing, laparoscopic, or robotic-assisted.

Radiation therapies or treatments may include external beam radiation therapy or internal radiation therapy. External beam radiation therapy may include three-dimensional conformal radiation therapy, intensity modulated radiation therapy, stereotactic body radiation therapy, or protein beam radiation therapy. Internal radiation therapy (or brachytherapy) may include permanent or temporary approaches. As used herein, salvage radiation therapy is radiation treatment that occurs after a first round of treatment for prostate cancer.

Adjuvant therapies or treatments may include chemotherapy, hormone therapy, biologic therapy (including immunotherapy), radiation therapy or targeted therapy. Chemotherapeutic treatments may include administration of Docetaxel (Taxotere®), Cabazitaxel (Jevtana®), Mitoxantrone (Novantrone®), Estramustine (Emcyt®), Doxorubicin (Adriamycin®), Etoposide (VP-16), Vinblastine (Velban®), Paclitaxel (Taxol®), Carboplatin (Paraplatin®), or Vinorelbine (Navelbine®), alone or in any combination. Hormone therapies may include luteinizing hormone-releasing hormone agonists, luteinizing hormone-releasing hormone antagonists, CYP17 inhibitors, anti-androgens, or estrogens.

Also disclosed is a kit for predicting biochemical recurrence after radical prostatectomy. The kit may include a panel of oligonucleotides configured to bind to a group of miRNAs consisting of those listed in Table 2. Also disclosed is a kit for predicting biochemical recurrence after radiation treatment or therapy. The kit may include a panel of oligonucleotides configured to bind to a group of miRNAs consisting of those listed in Table 3.

A number of embodiments of the invention have been described. Nevertheless, it will be understood that various modifications may be made without departing from the spirit and scope of the invention. Accordingly, other embodiments are within the scope of the following claims.

EXAMPLE

Example 1: An miRNA-Based Predictive Model for Biochemical Recurrence Following Post-Prostatectomy Salvage Radiation Therapy Materials and Methods
Patient Cohort.

Figure 6:
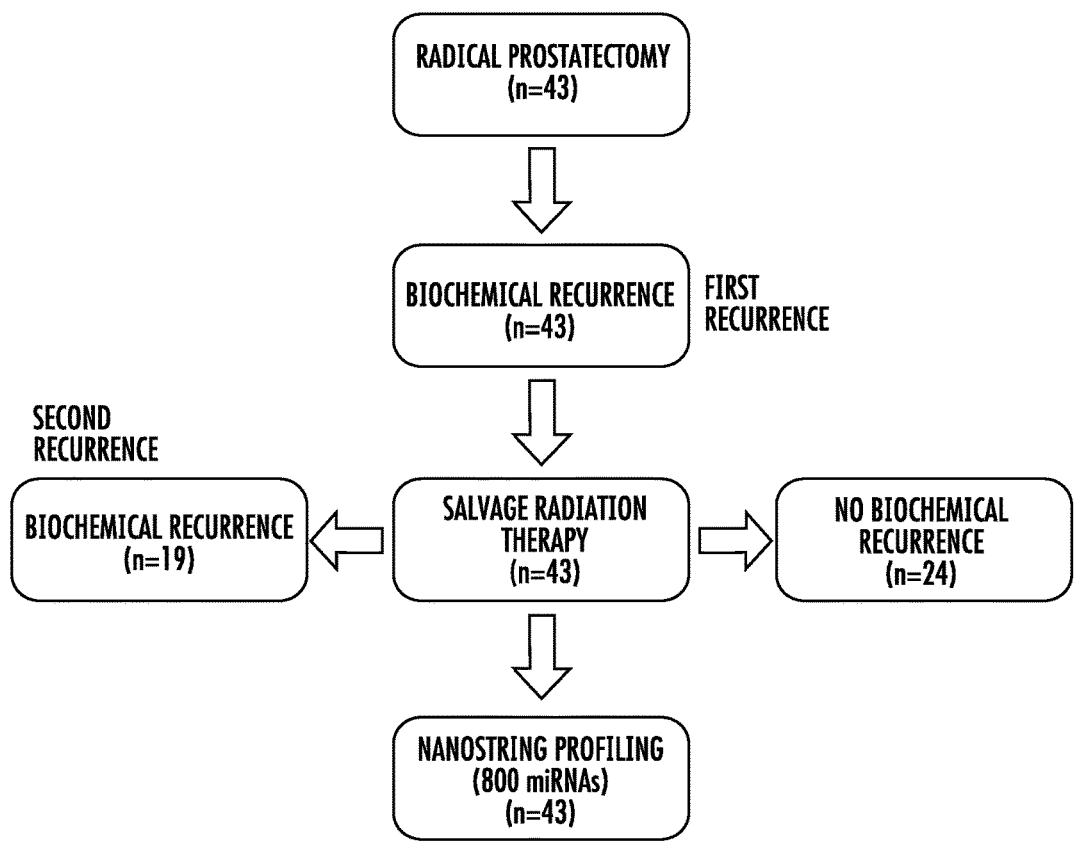
FIG. 6 shows a flow chart of the study design used in the example.

FFPE blocks from 43 patients with PCa who had undergone RP (1997-2009) followed by salvage RT between 2005 and 2011 at the University of Freiburg, Germany, were used in this study. A flow chart of the study design can be found in FIG. 6. Patients who received adjuvant RT (RT initiated less than 6 months after RP) were excluded from the analysis. Follow-up time after RT was defined to be greater than 4 years. A clinical database was established which contained patient characteristics, tumor classification according to the International Union Against Cancer (UICC)/American Joint Committee on Cancer (AJCC) 2010 TNM system due to the dates of the earliest radical prostatectomies in the study, tumor grading according to Gleason score without inclusion of tertiary score, radiation treatment details including toxicities, and follow-up details including PSA concentrations. There were no significant differences in terms of radiation techniques, planning target volume generation, doses and radiation volumes in the cohort. All patients were treated 1.8-2.0 Gy per fraction to a total dose of 66.6-74 Gy. Use of hormone therapy and whole pelvis radiation was at the discretion of the treating physician. Recurrence was defined as either biochemical failure (BF) with a rise of PSA≥0.2 ng/ml at least twice as per the AUA recommendation or clinical progression with local (prostatic fossa), regional (lymph nodes) or distant (metastasis) recurrence. Imaging tests (CT, PET/CT or bone scan) were done when clinically indicated in cases of BF.

Ethics Statement.

This study was approved by both the Medical Center University Freiburg and The Ohio State University institutional review boards with waived patient consent due to the archival nature of the study. In addition, data and tissue samples pertaining to this study were de-identified prior to analysis.

Sample Processing & RNA Isolation.

All formalin-fixed, paraffin-embedded (FFPE) blocks were reviewed by the same pathologist specialized in genitourinary diseases and Gleason scores were reassessed for each core using the ISUP 2005 grading system (Epstein et al., American Journal of Surgical Pathology, 2005). Tissue samples from the Medical Center University of Freiburg pathology tissue bank were obtained which included tissue from prostate tumor, non-neoplastic prostate epithelium, and non-neoplastic prostate stroma. Areas of interest were marked on an H&E stained slide and 1-mm diameter biopsy cores were punched from each area of interest. Cores from tumor were taken from the area with the highest Gleason Score and were enriched for tumor (>70/o).

Total RNA was isolated using a combination of RecoverAll Total Nucleic Acid Isolation digestion buffer, AM1975, (Life Technologies; Carlsbad, Calif.) with Qiagen FFPE miRNeasy kit, Cat. #217504 (Qiagen; Venlo, Limburg). In brief, cores were digested overnight using RecoverAll Total Nucleic Acid Isolation digestion buffer and proteinase K leading to enhanced digestion of the core. Once cores were digested (next day), the Qiagen FFPE miRNeasy manual was followed starting at the 80° C. for 15 minute incubation. RNA concentrations were measured using a NanoDrop 2000 spectrophotometer (Thermo Scientific; Waltham, Mass.).

miRNA4 Expression Analysis.

For miRNA expression data generation, the NanoString human v2 array, which contains 800 miRNA probes, was used. Forty three tumor, 31 epithelium, and 21 stroma samples were analyzed. Expression analysis was conducted at The Ohio State University Nucleic Acid Core Facility (Columbus, Ohio). A total of 100 ng RNA input was used per sample and conditions were set according to the manufacturer's recommended protocol (NanoString Technologies; Seattle, Wash.). miRNAs were quantified using the nCounter Digital Analyzer as counts. miRNAs were filtered out from downstream analysis if total counts were less than 32 across 90% of the samples. Four hundred and seventy seven miRs were left after the filtering. Data were normalized by the geometric mean of all targets using the nSolver software (NanoString Technologies; Seattle, Wash.).

Statistical Analysis.

For tissue specific comparisons, 31 matched tumor and epithelium, 21 matched tumor and stroma, and 21 epithelium and stroma pairs were used. Normalized NanoString data were analyzed using Analysis of variance (ANOVA) with repeated measures method. A pairwise comparison was used to determine expression differences between tumor, stroma and epithelium.

To compare the difference in miRNA expression between late and early time to first biochemical recurrence post-RP (36 months as a cutoff) or between the time to the recurrence post-salvage RT, 2-sample t-tests were used. For each miRNA, patients were dichotomized into high and low groups based on the median miRNA expression and the difference in the probabilities of the time to the recurrence (post-RP or post-salvage RT recurrence) were compared using the log-rank test for each miRNA. Multivariate analyses were performed using COX proportional hazard regression models. ROC curve analysis was performed to determine the capability and cut-off level of variables that distinguished between the recurrence and non-recurrence of post-salvage RT. All analyses were performed using SAS 9.3 (SAS, Inc; Cary, N.C.) or R 3.0.

Results

Prostate Issue-Specific miRNA Expression Profiles.

In order to validate known miRNAs and identify novel miRNAs differentially regulated in prostate tumor tissue and adjacent tissues, expression data from tumor tissue (n=43) benign epithelium (n=31) and stroma (n=21) of 43 evaluable patients were analyzed using NanoString technology. As shown in Table 4, 45 miRNAs were significantly differentially expressed 1.5-fold or greater in tumor compared to epithelium; of those 11 were differentially expressed greater than 2-fold (p-value<0.05) (Table 1). One hundred and eight miRNAs were significantly differentially expressed greater than 1.5-fold in tumor when compared with stroma and of those miRNAs, 27 were differentially expressed 2-fold or more (p-value<0.05) (Table 4). Comparing epithelium and stroma samples, 84 miRNAs were significantly differentially expressed greater than 1.5-fold and of those miRNAs, 24 were differentially expressed 2-fold or more (ANOVA, p-value<0.05) (Table 4). Of the miRNAs significantly differentially expressed 1.5-fold or greater between all tissues types, 330 miRNAs were similar among all comparisons (FIG. 1).

TABLE 4

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-205-5p | 0.19748 | 0.0002 | hsa-miR-204-5p | 0.30722 | <.0001 | hsa-miR-4508 | 0.3007 | <.0001 |
| hsa-miR-1283 | 0.26303 | 0.0024 | hsa-miR-221-3p | 0.33791 | <.0001 | hsa-miR-4425 | 0.3839 | <.0001 |
| hsa-miR-221-3p | 0.34003 | <.0001 | hsa-miR-222-3p | 0.3428 | <.0001 | hsa-miR-548a1 | 0.3959 | <.0001 |
| hsa-miR-222-3p | 0.35894 | <.0001 | hsa-miR-143-3p | 0.35346 | <.0001 | hsa-miR-454-3p | 0.4133 | <.0001 |
| hsa-miR-145-5p | 0.40273 | 0.0002 | hsa-miR-23b-3p | 0.38186 | <.0001 | hsa-miR-548p | 0.4279 | <.0001 |
| hsa-miR-1253 | 0.4223 | 0.0015 | hsa-miR-145-5p | 0.38408 | 0.0005 | hsa-miR-516a-5p | 0.431 | <.0001 |
| hsa-miR-133a | 0.48172 | <.0001 | hsa-miR-1 | 0.40192 | <.0001 | hsa-miR-370 | 0.4452 | <.0001 |
| hsa-miR-1 | 0.49242 | <.0001 | hsa-miR-133a | 0.43283 | <.0001 | hsa-miR-219-1-3p | 0.4564 | <.0001 |
| hsa-miR-143-3p | 0.49585 | 0.0006 | hsa-miR-199a-3p?miR-199b- | 0.43876 | <.0001 | hsa-miR-1185-5p | 0.4752 | <.0001 |
| hsa-miR-549 | 0.50386 | 0.0011 | hsa-miR-454-3p | 0.45904 | <.0001 | hsa-miR-424-5p | 0.4819 | <.0001 |
| hsa-miR-204-5p | 0.50859 | <.0001 | hsa-miR-455-3p | 0.45906 | <.0001 | hsa-miR-325 | 0.4957 | <.0001 |
| hsa-miR-130a-3p | 0.51 | <.0001 | hsa-miR-214-3p | 0.46623 | <.0001 | hsa-miR-455-3p | 0.5222 | <.0001 |
| hsa-miR-27b-3p | 0.51173 | 0.0003 | hsa-miR-516a-5p | 0.46797 | <.0001 | hsa-miR-23c | 0.5531 | <.0001 |
| hsa-miR-378e | 0.5256 | 0.0022 | hsa-miR-130a-3p | 0.47211 | <.0001 | hsa-miR-4284 | 0.5584 | <.0001 |
| hsa-miR-100-5p | 0.52834 | <.0001 | hsa-miR-27b-3p | 0.47864 | 0.0004 | hsa-miR-606 | 0.5637 | <.0001 |
| hsa-miR-23b-3p | 0.52907 | 0.0003 | hsa-let-7e-5p | 0.48272 | <.0001 | hsa-miR-342-5p | 0.5668 | 0.0025 |
| hsa-miR-22-3p | 0.55427 | <.0001 | hsa-miR-34a-5p | 0.49571 | <.0001 | hsa-miR-548aj-3p | 0.5704 | <.0001 |
| hsa-miR-199a-5p | 0.55888 | <.0001 | hsa-miR-4508 | 0.50746 | <.0001 | hsa-miR-208a | 0.5787 | <.0001 |
| hsa-let-7e-5p | 0.56457 | 0.0001 | hsa-miR-205-5p | 0.52804 | 0.1611 | hsa-miR-495 | 0.589 | <.0001 |
| hsa-miR-455-5p | 0.56705 | <.0001 | hsa-miR-23a-3p | 0.53566 | 0.0003 | hsa-miR-654-3p | 0.5903 | <.0001 |
| hsa-miR-181a-5p | 0.56875 | <.0001 | hsa-miR-152 | 0.53615 | <.0001 | hsa-miR-384 | 0.5913 | <.0001 |
| hsa-miR-34a-5p | 0.61779 | <.0001 | hsa-miR-342-5p | 0.5428 | 0.0006 | hsa-miR-665 | 0.5983 | <.0001 |
| hsa-miR-99b-5p | 0.61884 | <.0001 | hsa-miR-424-5p | 0.55591 | <.0001 | hsa-miR-517a-3p | 0.6028 | <.0001 |
| hsa-miR-125b-5p | 0.62136 | 0.0011 | hsa-miR-370 | 0.5609 | <.0001 | hsa-miR-204-5p | 0.6041 | 0.0105 |
| hsa-miR-99a-5p | 0.62307 | 0.0014 | hsa-miR-127-3p | 0.56517 | <.0001 | hsa-miR-323a-3p | 0.6054 | <.0001 |
| hsa-miR-126-3p | 0.62482 | 0.002 | hsa-miR-29b-3p | 0.56706 | 0.0017 | hsa-miR-615-5p | 0.6125 | 0.0007 |
| hsa-miR-23a-3p | 0.63183 | 0.0022 | hsa-miR-125b-5p | 0.56976 | 0.0007 | hsa-miR-127-3p | 0.6199 | <.0001 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-199a-3p?miR-199b-3p | 0.6353 | 0.0045 | hsa-miR-23c | 0.57329 | <.0001 | hsa-miR-659-3p | 0.6211 | <.0001 |
| hsa-miR-542-5p | 0.64145 | 0.0001 | hsa-miR-548al | 0.58235 | <.0001 | hsa-miR-16-5p | 0.6262 | 0.0075 |
| hsa-miR-223-3p | 0.65116 | 0.0055 | hsa-miR-219-1-3p | 0.58486 | <.0001 | hsa-miR-1277-3p | 0.6276 | <.0001 |
| hsa-miR-30c-5p | 0.65141 | 0.0039 | hsa-miR-1233 | 0.58704 | <.0001 | hsa-miR-580 | 0.6333 | <.0001 |
| hsa-miR-24-3p | 0.65778 | 0.0064 | hsa-miR-100-5p | 0.59362 | 0.0018 | hsa-miR-3184-5p | 0.6376 | <.0001 |
| hsa-miR-593-3p | 0.66992 | 0.0005 | hsa-miR-4425 | 0.5989 | 0.0004 | hsa-miR-301a-3p | 0.6538 | 0.0002 |
| hsa-miR-548aa | 0.6759 | 0.0093 | hsa-miR-99b-5p | 0.5999 | <.0001 | hsa-miR-342-3p | 0.6675 | 0.0081 |
| hsa-miR-214-3p | 0.67866 | 0.0001 | hsa-miR-542-5p | 0.60152 | <.0001 | hsa-miR-658 | 0.6708 | 0.0002 |
| hsa-miR-338-3p | 0.68031 | <.0001 | hsa-miR-455-5p | 0.60434 | <.0001 | hsa-miR-532-5p | 0.6751 | 0.075 |
| hsa-miR-125a-5p | 0.69004 | 0.002 | hsa-miR-208a | 0.60571 | <.0001 | hsa-miR-362-3p | 0.686 | 0.0014 |
| hsa-miR-136-5p | 0.69037 | 0.0003 | hsa-miR-29a-3p | 0.60724 | 0.0015 | hsa-miR-214-3p | 0.687 | 0.0014 |
| hsa-miR-3195 | 0.70188 | 0.0401 | hsa-miR-338-3p | 0.61242 | <.0001 | hsa-miR-2682-5p | 0.6889 | 0.0002 |
| hsa-miR-218-5p | 0.7088 | 0.0005 | hsa-miR-199a-5p | 0.61379 | 0.001 | hsa-miR-199a-3p?miR-199b-3p | 0.6906 | 0.0481 |
| hsa-miR-597 | 0.71327 | <.0001 | hsa-miR-342-3p | 0.61403 | 0.0009 | hsa-miR-4458 | 0.6912 | 0.0089 |
| hsa-miR-1276 | 0.71574 | 0.0559 | hsa-miR-495 | 0.61987 | <.0001 | hsa-miR-423-5p | 0.6914 | <.0001 |
| hsa-miR-365a-3p | 0.71864 | 0.0043 | hsa-miR-28-5p | 0.62129 | 0.0001 | hsa-miR-9-5p | 0.6943 | 0.0043 |
| hsa-miR-1972 | 0.72462 | 0.2171 | hsa-miR-548p | 0.62147 | 0.0001 | hsa-miR-656 | 0.6953 | 0.0001 |
| hsa-miR-29b-3p | 0.73214 | 0.0447 | hsa-miR-218-5p | 0.62385 | <.0001 | hsa-miR-152 | 0.6982 | 0.0019 |
| hsa-miR-2054 | 0.73497 | 0.0077 | hsa-miR-136-5p | 0.62575 | <.0001 | hsa-miR-548a-3p | 0.708 | <.0001 |
| hsa-let-7c | 0.7384 | 0.025 | hsa-miR-24-3p | 0.6271 | 0.0071 | hsa-miR-26a-5p | 0.7113 | 0.1328 |
| hsa-miR-187-3p | 0.73981 | 0.0021 | hsa-miR-99a-5p | 0.62879 | 0.005 | hsa-miR-518c-3p | 0.7113 | 0.0034 |
| hsa-let-7f-5p | 0.75246 | 0.0538 | hsa-let-7g-5p | 0.63233 | 0.0044 | hsa-miR-143-3p | 0.7128 | 0.1438 |
| hsa-miR-199b-5p | 0.753 | 0.07 | hsa-miR-325 | 0.63463 | 0.0002 | hsa-miR-628-3p | 0.7149 | 0.0004 |
| hsa-miR-376c | 0.75684 | 0.0012 | hsa-miR-384 | 0.63628 | <.0001 | hsa-miR-140-3p | 0.7178 | 0.0241 |
| hsa-let-7i-5p | 0.75956 | 0.0196 | hsa-miR-665 | 0.64696 | <.0001 | hsa-miR-515-5p | 0.7197 | 0.0024 |
| hsa-miR-497-5p | 0.76253 | 0.0381 | hsa-miR-126-3p | 0.65011 | 0.0111 | hsa-miR-518b | 0.7205 | 0.0008 |
| hsa-miR-4454 | 0.76289 | 0.0449 | hsa-miR-301a-3p | 0.65348 | <.0001 | hsa-miR-23b-3p | 0.7217 | 0.1064 |
| hsa-miR-1264 | 0.76687 | 0.0017 | hsa-let-7i-5p | 0.65827 | 0.0021 | hsa-miR-769-5p | 0.7223 | 0.0037 |
| hsa-miR-152 | 0.76791 | 0.0057 | hsa-miR-150-5p | 0.65898 | 0.0402 | hsa-miR-423-3p | 0.725 | <.0001 |
| hsa-miR-4532 | 0.76849 | 0.041 | hsa-let-7c | 0.65939 | 0.0071 | hsa-miR-4443 | 0.7266 | 0.0443 |
| hsa-miR-548n | 0.76868 | 0.0007 | hsa-miR-16-5p | 0.66035 | 0.0115 | hsa-miR-761 | 0.7302 | 0.0293 |
| hsa-miR-376a-3p | 0.76928 | 0.0259 | hsa-miR-22-3p | 0.66408 | 0.0093 | hsa-miR-548ad | 0.7314 | <.0001 |
| hsa-miR-29a-3p | 0.76964 | 0.0511 | hsa-miR-323a-3p | 0.66624 | <.0001 | hsa-miR-182-5p | 0.735 | 0.0253 |
| hsa-miR-1233 | 0.77009 | 0.0143 | hsa-miR-186-5p | 0.66711 | 0.0004 | hsa-miR-598 | 0.7374 | 0.0212 |
| hsa-miR-331-5p | 0.77148 | 0.0013 | hsa-miR-199b-5p | 0.66732 | 0.0235 | hsa-miR-33a-5p | 0.7449 | 0.0004 |
| hsa-miR-935 | 0.77435 | 0.0088 | hsa-let-7d-5p | 0.66936 | 0.0013 | hsa-miR-891b | 0.7495 | 0.0033 |
| hsa-miR-98 | 0.77954 | 0.0489 | hsa-miR-187-3p | 0.67114 | 0.0004 | hsa-miR-1231 | 0.7539 | 0.0025 |
| hsa-miR-3185 | 0.78001 | 0.0014 | hsa-miR-548aj-3p | 0.68079 | 0.0003 | hsa-miR-450b-5p | 0.7555 | 0.0033 |
| hsa-miR-150-5p | 0.78714 | 0.1781 | hsa-miR-193a-5p | 0.68614 | 0.0002 | hsa-miR-1908 | 0.757 | 0.0211 |
| hsa-miR-450a-5p | 0.7886 | 0.005 | hsa-miR-769-5p | 0.68692 | 0.0005 | hsa-miR-1233 | 0.7623 | 0.0325 |
| hsa-let-7g-5p | 0.79354 | 0.0952 | hsa-miR-1185-5p | 0.6921 | 0.0008 | hsa-miR-3934 | 0.7638 | 0.0029 |
| hsa-miR-574-5p | 0.79496 | 0.0731 | hsa-miR-1277-3p | 0.69368 | 0.0002 | hsa-miR-1827 | 0.7688 | 0.0028 |
| hsa-miR-1279 | 0.79531 | 0.0037 | hsa-miR-125a-5p | 0.69606 | 0.0069 | hsa-miR-626 | 0.7695 | 0.0368 |
| hsa-miR-4647 | 0.79609 | 0.0019 | hsa-miR-140-3p | 0.70238 | 0.0113 | hsa-miR-432-5p | 0.77 | 0.0038 |
| hsa-miR-1180 | 0.79817 | 0.0066 | hsa-miR-26a-5p | 0.70328 | 0.0999 | hsa-miR-28-5p | 0.7729 | 0.0361 |
| hsa-miR-548ah-5p | 0.80004 | 0.0272 | hsa-miR-30c-5p | 0.70347 | 0.0324 | hsa-miR-1303 | 0.7743 | 0.293 |
| hsa-miR-155-5p | 0.80335 | 0.0058 | hsa-miR-1231 | 0.7152 | 0.0002 | hsa-miR-29b-3p | 0.7745 | 0.1657 |
| hsa-miR-28-5p | 0.80389 | 0.0333 | hsa-miR-365a-3p | 0.71628 | 0.01 | hsa-let-7d-5p | 0.7748 | 0.047 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-548ab | 0.80432 | 0.143 | hsa-miR-891b | 0.7167 | 0.0004 | hsa-miR-2276 | 0.7748 | 0.0048 |
| hsa-miR-548d-3p | 0.80626 | 0.0652 | hsa-miR-324-5p | 0.72099 | 0.0018 | hsa-miR-3180 | 0.7751 | 0.0098 |
| hsa-miR-548q | 0.8071 | 0.0243 | hsa-miR-30a-5p | 0.7224 | 0.0103 | hsa-miR-508-5p | 0.776 | 0.0179 |
| hsa-miR-324-5p | 0.808 | 0.0191 | hsa-miR-2682-5p | 0.72275 | 0.0005 | hsa-miR-938 | 0.7777 | 0.0008 |
| hsa-miR-18b-5p | 0.80887 | 0.0466 | hsa-miR-4443 | 0.72908 | 0.0351 | hsa-miR-568 | 0.7787 | 0.0289 |
| hsa-miR-2117 | 0.81113 | 0.0056 | hsa-miR-615-5p | 0.73109 | 0.0178 | hsa-miR-663a | 0.7796 | 0.0344 |
| hsa-miR-193a-5p | 0.8171 | 0.0194 | hsa-miR-451a | 0.73252 | 0.2396 | hsa-miR-451a | 0.7819 | 0.3798 |
| hsa-miR-135b-5p | 0.81825 | 0.0265 | hsa-miR-519b-5p?miR-519c- | 0.73405 | 0.0012 | hsa-miR-425-5p | 0.7833 | 0.0161 |
| hsa-miR-378a-3p?miR-3781 | 0.82024 | 0.043 | hsa-miR-628-3p | 0.73439 | 0.0005 | hsa-miR-1208 | 0.7839 | 0.0026 |
| hsa-miR-181c-5p | 0.82102 | 0.0326 | hsa-miR-517a-3p | 0.73463 | 0.0049 | hsa-miR-590-5p | 0.7843 | 0.0008 |
| hsa-miR-144-3p | 0.82476 | 0.1619 | hsa-miR-656 | 0.74057 | 0.0006 | hsa-miR-140-5p | 0.7862 | 0.0723 |
| hsa-miR-4741 | 0.8292 | 0.0026 | hsa-miR-525-3p | 0.74313 | 0.0009 | hsa-miR-186-5p | 0.7866 | 0.0393 |
| hsa-miR-496 | 0.83049 | 0.012 | hsa-miR-193b-3p | 0.74989 | 0.0162 | hsa-miR-450b-3p | 0.7866 | 0.0555 |
| hsa-miR-572 | 0.83232 | 0.0326 | hsa-miR-518b | 0.75744 | 0.0023 | hsa-miR-29a-3p | 0.789 | 0.1379 |
| hsa-miR-374b-5p | 0.83109 | 0.1435 | hsa-miR-548ad | 0.75989 | 0.0002 | hsa-miR-15b-5p | 0.7922 | 0.0906 |
| hsa-miR-2116-5p | 0.83417 | 0.152 | hsa-let-7f-5p | 0.76069 | 0.099 | hsa-miR-647 | 0.7938 | 0.0128 |
| hsa-miR-411-5p | 0.83444 | 0.0047 | hsa-miR-4532 | 0.76287 | 0.0621 | hsa-miR-563 | 0.7944 | 0.0704 |
| hsa-miR-485-3p | 0.83546 | 0.0342 | hsa-miR-219-5p | 0.76613 | 0.0009 | hsa-miR-374a-5p | 0.7953 | 0.1439 |
| hsa-miR-500a-5p?miR-501-5 | 0.83688 | 0.0032 | hsa-miR-98 | 0.76711 | 0.0629 | hsa-miR-525-3p | 0.7954 | 0.0133 |
| hsa-miR-381 | 0.83799 | 0.0095 | hsa-miR-654-3p | 0.76727 | 0.0127 | hsa-miR-564 | 0.7965 | 0.014 |
| hsa-miR-483-3p | 0.84189 | 0.0352 | hsa-miR-376c | 0.76883 | 0.0061 | hsa-let-7g-5p | 0.7969 | 0.17 |
| hsa-miR-514a-3p | 0.84402 | 0.0197 | hsa-miR-27a-3p | 0.76885 | 0.0052 | hsa-miR-330-5p | 0.7973 | 0.0061 |
| hsa-miR-26b-5p | 0.84428 | 0.1897 | hsa-miR-658 | 0.77687 | 0.0105 | hsa-miR-132-3p | 0.7975 | 0.0429 |
| hsa-miR-1260b | 0.84432 | 0.0971 | hsa-miR-876-3p | 0.78233 | 0.0078 | hsa-miR-448 | 0.7978 | 0.0094 |
| hsa-miR-337-5p | 0.84565 | 0.0224 | hsa-miR-518c-3p | 0.78329 | 0.0234 | hsa-miR-499a-3p | 0.7991 | 0.037 |
| hsa-miR-1268b | 0.84788 | 0.0528 | hsa-miR-423-5p | 0.78341 | 0.0023 | hsa-miR-519b-5p?miR-519c- | 0.7994 | 0.0234 |
| hsa-miR-186-5p | 0.84807 | 0.0874 | hsa-miR-548a-3p | 0.78351 | 0.0012 | hsa-miR-34-5p | 0.8024 | 0.0925 |
| hsa-miR-1228-3p | 0.8511 | 0.0225 | hsa-miR-450a-5p | 0.78371 | 0.0102 | hsa-miR-4455 | 0.8128 | 0.0184 |
| hsa-miR-302a-3p | 0.85302 | 0.0611 | hsa-miR-3180 | 0.78474 | 0.0091 | hsa-miR-302e | 0.813 | 0.0072 |
| hsa-miR-193b-3p | 0.85351 | 0.1281 | hsa-miR-574-3p | 0.78502 | 0.0036 | hsa-miR-1 | 0.8162 | 0.2971 |
| hsa-miR-30a-5p | 0.85415 | 0.1501 | hsa-miR-329 | 0.78556 | 0.0068 | hsa-miR-566 | 0.8177 | 0.0085 |
| hsa-miR-542-3p | 0.85423 | 0.0159 | hsa-miR-409-3p | 0.78858 | 0.0009 | hsa-miR-1226-3p | 0.8199 | 0.0388 |
| hsa-miR-1322 | 0.85552 | 0.242 | hsa-miR-626 | 0.79136 | 0.0473 | hsa-miR-362-5p | 0.8234 | 0.0287 |
| hsa-miR-4488 | 0.85664 | 0.2798 | hsa-miR-423-3p | 0.79275 | 0.0002 | hsa-miR-614 | 0.8235 | 0.0899 |
| hsa-miR-31-5p | 0.85829 | 0.0339 | hsa-miR-761 | 0.79752 | 0.0928 | hsa-miR-203 | 0.8272 | 0.1033 |
| hsa-miR-616-3p | 0.86079 | 0.0899 | hsa-miR-26b-5p | 0.79835 | 0.1237 | hsa-miR-194-5p | 0.8291 | 0.0232 |
| hsa-miR-299-3p | 0.86189 | 0.1465 | hsa-miR-3184-5p | 0.80096 | 0.017 | hsa-miR-1909-3p | 0.8297 | 0.0583 |
| hsa-miR-548y | 0.86239 | 0.2626 | hsa-miR-606 | 0.80164 | 0.0596 | hsa-miR-876-3p | 0.8298 | 0.0528 |
| hsa-miR-942 | 0.86319 | 0.0639 | hsa-miR-140-5p | 0.80273 | 0.0811 | hsa-miR-1234 | 0.8304 | 0.196 |
| hsa-miR-621 | 0.86382 | 0.0223 | hsa-miR-580 | 0.80698 | 0.0285 | hsa-miR-941 | 0.8306 | 0.0151 |
| hsa-let-7d-5p | 0.86396 | 0.1677 | hsa-miR-548z | 0.80723 | 0.0725 | hsa-miR-137 | 0.8309 | 0.6049 |
| hsa-miR-1183 | 0.8664 | 0.1806 | hsa-miR-564 | 0.80728 | 0.0141 | hsa-miR-449c-5p | 0.8309 | 0.0176 |
| hsa-miR-142-3p | 0.86645 | 0.4337 | hsa-miR-432-5p | 0.80804 | 0.0113 | hsa-miR-766-3p | 0.8321 | 0.0305 |
| hsa-miR-181b-5p?miR-181d | 0.86658 | 0.0456 | hsa-miR-502-3p | 0.8096 | 0.027 | hsa-miR-654-5p | 0.8324 | 0.0387 |
| hsa-miR-550b-3p | 0.87051 | 0.0826 | hsa-miR-2276 | 0.81166 | 0.0133 | hsa-miR-150-5p | 0.8372 | 0.4019 |
| hsa-miR-382-5p | 0.87084 | 0.0517 | hsa-miR-181a-5p | 0.81425 | 0.1639 | hsa-miR-1539 | 0.8377 | 0.0301 |
| hsa-miR-3123 | 0.87195 | 0.0998 | hsa-miR-330-5p | 0.81446 | 0.0082 | hsa-miR-193a-5p | 0.8397 | 0.0877 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-888-5p | 0.87198 | 0.2774 | hsa-miR-181c-5p | 0.81462 | 0.0485 | hsa-miR-582-5p | 0.8397 | 0.193 |
| hsa-miR-644a | 0.87422 | 0.0368 | hsa-miR-374a-5p | 0.81635 | 0.1688 | hsa-miR-548z | 0.8409 | 0.168 |
| hsa-miR-489 | 0.8745 | 0.0665 | hsa-miR-659-3p | 0.82019 | 0.032 | hsa-miR-3175 | 0.8448 | 0.1257 |
| hsa-miR-548x-3p | 0.87658 | 0.0164 | hsa-miR-30e-5p | 0.82168 | 0.0439 | hsa-miR-30a-5p | 0.8458 | 0.2013 |
| hsa-miR-574-3p | 0.87658 | 0.0657 | hsa-miR-331-5p | 0.82218 | 0.0271 | hsa-miR-23a-3p | 0.8478 | 0.3381 |
| hsa-miR-455-3p | 0.8791 | 0.151 | hsa-miR-223-3p | 0.82409 | 0.252 | hsa-miR-147b | 0.8489 | 0.0448 |
| hsa-miR-409-3p | 0.88122 | 0.0383 | hsa-miR-28-3p | 0.82816 | 0.06 | hsa-miR-1252 | 0.8497 | 0.0297 |
| hsa-miR-520h | 0.88512 | 0.1182 | hsa-miR-487b | 0.83064 | 0.0901 | hsa-miR-494 | 0.8534 | 0.5664 |
| hsa-miR-30e-5p | 0.88546 | 0.1542 | hsa-miR-941 | 0.83681 | 0.0134 | hsa-let-7e-5p | 0.855 | 0.3462 |
| hsa-let-7b-5p | 0.88572 | 0.2839 | hsa-miR-598 | 0.83935 | 0.1527 | hsa-miR-27a-3p | 0.8569 | 0.1123 |
| hsa-miR-570-3p | 0.88585 | 0.2204 | hsa-miR-3934 | 0.83946 | 0.0357 | hsa-miR-519e-3p | 0.8577 | 0.0654 |
| hsa-miR-613 | 0.88767 | 0.0886 | hsa-miR-1303 | 0.84322 | 0.4554 | hsa-miR-219-5p | 0.8614 | 0.0692 |
| hsa-miR-361-3p | 0.88855 | 0.0404 | hsa-miR-154-5p | 0.84332 | 0.022 | hsa-miR-576-5p | 0.8647 | 0.3077 |
| hsa-miR-219-5p | 0.88944 | 0.0864 | hsa-miR-3123 | 0.84833 | 0.0809 | hsa-let-7i-5p | 0.8667 | 0.3005 |
| hsa-miR-548l | 0.88987 | 0.147 | hsa-miR-582-5p | 0.85037 | 0.1998 | hsa-miR-340-5p | 0.8671 | 0.2222 |
| hsa-miR-548i | 0.89029 | 0.2241 | hsa-miR-499a-3p | 0.85063 | 0.107 | hsa-miR-30b-5p | 0.8705 | 0.47 |
| hsa-miR-1281 | 0.89159 | 0.1645 | hsa-miR-647 | 0.85363 | 0.0661 | hsa-miR-18a-5p | 0.8711 | 0.0366 |
| hsa-miR-320a | 0.89169 | 0.1508 | hsa-miR-362-3p | 0.85368 | 0.1384 | hsa-miR-125a-3p | 0.8721 | 0.1376 |
| hsa-miR-548t-5p | 0.89363 | 0.054 | hsa-miR-1909-3p | 0.85371 | 0.0876 | hsa-miR-329 | 0.8762 | 0.152 |
| hsa-miR-329 | 0.89653 | 0.1554 | hsa-miR-4647 | 0.85411 | 0.0498 | hsa-miR-193b-3p | 0.8786 | 0.297 |
| hsa-miR-27a-3p | 0.89721 | 0.1793 | hsa-miR-1197 | 0.85476 | 0.104 | hsa-miR-548k | 0.8798 | 0.0902 |
| hsa-miR-330-3p | 0.89791 | 0.1081 | hsa-miR-568 | 0.8551 | 0.1413 | hsa-miR-218-5p | 0.8801 | 0.2557 |
| hsa-miR-936 | 0.89831 | 0.1364 | hsa-miR-378a-3p?miR-378i | 0.85528 | 0.1533 | hsa-miR-1197 | 0.8835 | 0.2242 |
| hsa-miR-548ai | 0.90028 | 0.2245 | hsa-miR-4516 | 0.8565 | 0.3469 | hsa-miR-199b-5p | 0.8862 | 0.514 |
| hsa-miR-511 | 0.90062 | 0.1724 | hsa-miR-147b | 0.85907 | 0.0481 | hsa-miR-502-3p | 0.8885 | 0.2353 |
| hsa-miR-520d-5p?miR-518a- | 0.90099 | 0.3025 | hsa-miR-133b | 0.86212 | 0.0552 | hsa-miR-130b-3p | 0.8898 | 0.0765 |
| hsa-miR-1244 | 0.9021 | 0.1306 | hsa-miR-132-3p | 0.86318 | 0.1577 | hsa-miR-1288 | 0.8904 | 0.1939 |
| hsa-miR-28-3p | 0.90283 | 0.2441 | hsa-miR-644a | 0.86469 | 0.0453 | hsa-miR-324-5p | 0.8923 | 0.2856 |
| hsa-miR-133b | 0.90719 | 0.1516 | hsa-miR-576-5p | 0.86526 | 0.2811 | hsa-miR-331-3p | 0.8926 | 0.1019 |
| hsa-miR-1294 | 0.90865 | 0.131 | hsa-miR-331-3p | 0.86535 | 0.0288 | hsa-let-7c | 0.893 | 0.4757 |
| hsa-miR-502-3p | 0.9112 | 0.2624 | hsa-miR-448 | 0.87229 | 0.0892 | hsa-miR-885-5p | 0.8939 | 0.1828 |
| hsa-miR-548a-5p | 0.91163 | 0.2632 | hsa-miR-125a-3p | 0.87331 | 0.1192 | hsa-miR-409-3p | 0.8949 | 0.1254 |
| hsa-miR-127-3p | 0.91175 | 0.2156 | hsa-miR-4284 | 0.87385 | 0.2568 | hsa-miR-574-3p | 0.8955 | 0.195 |
| hsa-miR-4421 | 0.91184 | 0.1852 | hsa-miR-483-3p | 0.87497 | 0.1434 | hsa-miR-195-5p | 0.8973 | 0.4947 |
| hsa-miR-487b | 0.91329 | 0.3443 | hsa-miR-381 | 0.87604 | 0.08 | hsa-miR-660-5p | 0.8974 | 0.3295 |
| hsa-miR-3161 | 0.91548 | 0.2538 | hsa-miR-15b-5p | 0.87891 | 0.3149 | hsa-miR-148b-3p | 0.8981 | 0.2877 |
| hsa-miR-520b | 0.91619 | 0.175 | hsa-miR-508-5p | 0.87897 | 0.192 | hsa-miR-154-5p | 0.8982 | 0.1667 |
| hsa-let-7a-5p | 0.91625 | 0.5293 | hsa-miR-195-5p | 0.88028 | 0.394 | hsa-miR-133a | 0.8985 | 0.5882 |
| hsa-miR-553 | 0.91766 | 0.3302 | hsa-miR-337-5p | 0.88047 | 0.1197 | hsa-miR-338-3p | 0.9002 | 0.2716 |
| hsa-miR-519b-5p?miR-519c- | 0.91824 | 0.2904 | hsa-miR-450b-5p | 0.8811 | 0.1456 | hsa-miR-95 | 0.9004 | 0.1652 |
| hsa-miR-342-3p | 0.91988 | 0.4973 | hsa-miR-194-5p | 0.88202 | 0.102 | hsa-miR-185-5p | 0.9037 | 0.136 |
| hsa-miR-548v | 0.92183 | 0.2955 | hsa-miR-1281 | 0.88308 | 0.1821 | hsa-miR-216a | 0.9049 | 0.341 |
| hsa-miR-513a-3p | 0.92256 | 0.4578 | hsa-miR-33a-5p | 0.88454 | 0.0966 | hsa-miR-3928 | 0.9059 | 0.2575 |
| hsa-miR-664-3p | 0.92369 | 0.437 | hsa-miR-9-5p | 0.88546 | 0.2947 | hsa-miR-627 | 0.906 | 0.1383 |
| hsa-miR-376b | 0.92459 | 0.1983 | hsa-miR-181b-5p?miR-181d | 0.88642 | 0.1328 | hsa-miR-136-5p | 0.9064 | 0.3979 |
| hsa-miR-210 | 0.92523 | 0.2923 | hsa-miR-362-5p | 0.88765 | 0.1486 | hsa-miR-187-3p | 0.9072 | 0.3855 |
| hsa-miR-603 | 0.92617 | 0.3078 | hsa-miR-566 | 0.88865 | 0.0945 | hsa-miR-212-3p | 0.9079 | 0.11 |
| hsa-miR-196b-5p | 0.92757 | 0.3763 | hsa-miR-605 | 0.89644 | 0.1065 | hsa-miR-487b | 0.9095 | 0.4092 |
| hsa-miR-4516 | 0.92986 | 0.6167 | hsa-miR-299-3p | 0.89717 | 0.3452 | hsa-miR-3168 | 0.9132 | 0.3994 |
| hsa-miR-190a | 0.93095 | 0.3815 | hsa-miR-3928 | 0.89766 | 0.1901 | hsa-miR-4448 | 0.914 | 0.4098 |
| hsa-miR-525-3p | 0.93423 | 0.3643 | hsa-miR-1208 | 0.89912 | 0.1483 | hsa-miR-891a | 0.914 | 0.2676 |
| hsa-miR-151a-3p | 0.93664 | 0.3061 | ha-miR-361-3p | 0.89914 | 0.1001 | hsa-miR-7-5p | 0.9143 | 0.3712 |
| hsa-miR-451a | 0.93687 | 0.7793 | hsa-miR-330-3p | 0.90075 | 0.166 | hsa-miR-4431 | 0.9159 | 0.4413 |
| hsa-miR-337-3p | 0.93766 | 0.2066 | hsa-miR-654-5p | 0.90227 | 0.2121 | hsa-miR-125b- | 0.917 | 0.6024 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-2053 | 0.93773 | 0.2563 | hsa-miR-1234 | 0.90353 | 0.4511 | hsa-miR-28-3p | 0.9173 | 0.4106 |
| hsa-miR-767-3p | 0.93809 | 0.5095 | hsa-miR-2054 | 0.90621 | 0.4352 | hsa-miR-1299 | 0.9188 | 0.4891 |
| hsa-miR-146a-5p | 0.93873 | 0.553 | hsa-miR-212-3p | 0.90683 | 0.0867 | hsa-miR-1273e | 0.9197 | 0.6613 |
| hsa-miR-154-5p | 0.93892 | 0.328 | hsa-miR-503 | 0.90715 | 0.2236 | hsa-miR-4516 | 0.9211 | 0.6372 |
| hsa-miR-1246 | 0.93942 | 0.5169 | hsa-miR-4454 | 0.9119 | 0.5378 | hsa-miR-635 | 0.9254 | 0.4293 |
| hsa-miR-1268a | 0.93999 | 0.5754 | hsa-miR-302e | 0.91322 | 0.198 | hsa-miR-130a-3p | 0.9257 | 0.6682 |
| hsa-miR-1179 | 0.94024 | 0.4189 | hsa-miR-18a-5p | 0.91533 | 0.15 | hsa-miR-128 | 0.9273 | 0.3585 |
| hsa-miR-502-5p | 0.94069 | 0.4311 | hsa-miR-4741 | 0.91789 | 0.2047 | hsa-miR-30e-5p | 0.928 | 0.462 |
| hsa-miR-579 | 0.94091 | 0.4659 | hsa-miR-1539 | 0.92148 | 0.2789 | hsa-miR-1206 | 0.9294 | 0.4775 |
| hsa-miR-216b | 0.9414 | 0.3302 | hsa-miR-494 | 0.9244 | 0.7625 | hsa-miR-551a | 0.9305 | 0.2295 |
| hsa-miR-876-3p | 0.94278 | 0.4558 | hsa-miR-374b-5p | 0.92559 | 0.5775 | hsa-miR-1287 | 0.9321 | 0.2824 |
| hsa-miR-720 | 0.94824 | 0.7109 | hsa-miR-551a | 0.92991 | 0.1986 | hsa-miR-503 | 0.9347 | 0.4246 |
| hsa-miR-1231 | 0.94873 | 0.4796 | hsa-miR-10a-5p | 0.93342 | 0.1992 | hsa-miR-146b-5p | 0.9353 | 0.6001 |
| hsa-miR-769-3p | 0.94997 | 0.3611 | hsa-miR-4488 | 0.93445 | 0.6736 | hsa-miR-27b-3p | 0.9353 | 0.7453 |
| hsa-miR-604 | 0.95019 | 0.5286 | hsa-miR-1180 | 0.93497 | 0.4574 | hsa-miR-542-5p | 0.9378 | 0.6131 |
| hsa-miR-29c-3p | 0.95054 | 0.7542 | hsa-miR-766-3p | 0.9357 | 0.3968 | hsa-miR-3605-5p | 0.9385 | 0.463 |
| hsa-miR-769-5p | 0.95101 | 0.5758 | hsa-miR-548v | 0.93764 | 0.4626 | hsa-miR-605 | 0.9414 | 0.3969 |
| hsa-miR-605 | 0.9522 | 0.4093 | hsa-miR-590-5p | 0.93952 | 0.3375 | hsa-miR-600 | 0.9439 | 0.6542 |
| hsa-miR-4531 | 0.95225 | 0.544 | hsa-miR-660-5p | 0.94003 | 0.5529 | hsa-miR-26b-5p | 0.9456 | 0.7157 |
| hsa-miR-149-5p | 0.95254 | 0.6534 | hsa-miR-585 | 0.9468 | 0.5064 | hsa-miR-3196 | 0.9483 | 0.4982 |
| hsa-miR-629-5p | 0.95263 | 0.427 | hsa-miR-663a | 0.94768 | 0.6205 | hsa-miR-133b | 0.9503 | 0.5282 |
| hsa-miR-762 | 0.95392 | 0.4759 | hsa-miR-320a | 0.9515 | 0.578 | hsa-miR-24-3p | 0.9534 | 0.7878 |
| hsa-miR-1260a | 0.95424 | 0.733 | hsa-miR-500a-5p?miR-501-5 | 0.95526 | 0.4835 | hsa-miR-145-5p | 0.9537 | 0.8626 |
| hsa-miR-944 | 0.9554 | 0.5858 | hsa-miR-593-3p | 0.95687 | 0.7196 | hsa-miR-548ak | 0.9541 | 0.6052 |
| hsa-miR-548g-3p | 0.95594 | 0.5799 | hsa-let-7b-5p | 0.95718 | 0.731 | hsa-miR-222-3p | 0.955 | 0.795 |
| ha-miR-891b | 0.95622 | 0.567 | hsa-miR-185-5p | 0.95726 | 0.4907 | hsa-miR-10a-5p | 0.9559 | 0.4257 |
| hsa-miR-342-5p | 0.95759 | 0.7714 | hsa-miR-548x-3p | 0.95727 | 0.4694 | hsa-miR-1238 | 0.9576 | 0.606 |
| hsa-miR-877-5p | 0.95936 | 0.5789 | hsa-miR-146b-5p | 0.95881 | 0.7263 | hsa-miR-1973 | 0.9599 | 0.6683 |
| hsa-miR-548z | 0.96001 | 0.6945 | hsa-miR-885-5p | 0.96225 | 0.6247 | hsa-miR-622 | 0.9605 | 0.7344 |
| hsa-miR-4461 | 0.96024 | 0.4531 | hsa-miR-4421 | 0.9656 | 0.654 | hsa-miR-631 | 0.9607 | 0.6559 |
| hsa-miR-3131 | 0.96062 | 0.6035 | hsa-miR-4448 | 0.9657 | 0.7335 | hsa-miR-361-5p | 0.9661 | 0.8247 |
| hsa-miR-107 | 0.96199 | 0.6981 | hsa-miR-1299 | 0.96591 | 0.7633 | hsa-miR-578 | 0.9666 | 0.613 |
| hsa-miR-422a | 0.96403 | 0.517 | hsa-miR-142-3p | 0.96685 | 0.8702 | hsa-miR-99b-5p | 0.9694 | 0.7629 |
| hsa-miR-1224-5p | 0.96518 | 0.6597 | hsa-miR-190a | 0.96758 | 0.7205 | hsa-miR-4286 | 0.9696 | 0.9182 |
| hsa-miR-1200 | 0.96529 | 0.6354 | hsa-miR-603 | 0.96817 | 0.7022 | hsa-miR-2110 | 0.97 | 0.726 |
| hsa-miR-514b-5p | 0.96682 | 0.5939 | hsa-miR-1827 | 0.96837 | 0.6848 | hsa-miR-585 | 0.972 | 0.7443 |
| hsa-miR-1197 | 0.96745 | 0.6949 | hsa-miR-146a-5p | 0.96956 | 0.7971 | hsa-miR-188-5p | 0.9721 | 0.6888 |
| hsa-miR-331-3p | 0.96949 | 0.5881 | hsa-miR-422a | 0.97541 | 0.6963 | hsa-miR-3123 | 0.9729 | 0.7805 |
| hsa-miR-922 | 0.96962 | 0.7249 | hsa-miR-1183 | 0.97607 | 0.84 | hsa-miR-15a-5p | 0.9742 | 0.8672 |
| hsa-miR-503 | 0.97056 | 0.6713 | hsa-miR-2053 | 0.9774 | 0.7194 | hsa-miR-758 | 0.9759 | 0.7889 |
| hsa-miR-641 | 0.97173 | 0.6183 | hsa-miR-614 | 0.97769 | 0.8319 | hsa-miR-491-5p | 0.9767 | 0.7886 |
| hsa-miR-585 | 0.97412 | 0.7183 | hsa-miR-1287 | 0.97848 | 0.7228 | hsa-miR-1286 | 0.9795 | 0.778 |
| hsa-miR-10b-5p | 0.97556 | 0.8255 | hsa-miR-376a-3p | 0.98049 | 0.8793 | hsa-miR-3182 | 0.9801 | 0.8843 |
| hsa-miR-10a-5p | 0.97653 | 0.6146 | hsa-miR-148b-3p | 0.9821 | 0.8487 | hsa-miR-1205 | 0.9808 | 0.8358 |
| hsa-miR-302d-3p | 0.97696 | 0.6623 | hsa-miR-216a | 0.98215 | 0.8548 | hsa-miR-484 | 0.9833 | 0.7766 |
| hsa-miR-541-3p | 0.97753 | 0.8314 | hsa-miR-15a-5p | 0.98227 | 0.9032 | hsa-miR-98 | 0.9841 | 0.9139 |
| hsa-miR-140-3p | 0.97853 | 0.8558 | hsa-miR-10b-5p | 0.98273 | 0.8907 | hsa-miR-548an | 0.9876 | 0.8702 |
| hsa-miR-548d-5p | 0.98011 | 0.8023 | hsa-miR-519e-3p | 0.98275 | 0.8217 | hsa-miR-644a | 0.9891 | 0.8846 |
| hsa-miR-195-5p | 0.98098 | 0.8843 | hsa-miR-769-3p | 0.98299 | 0.7862 | hsa-miR-1281 | 0.9905 | 0.9221 |
| hsa-miR-135a-5p | 0.98215 | 0.9142 | hsa-miR-4461 | 0.98448 | 0.7975 | hsa-miR-550a-5p | 0.9906 | 0.9103 |
| hsa-miR-1323 | 0.98516 | 0.8577 | hsa-miR-548ak | 0.98669 | 0.8754 | hsa-miR-181c-5p | 0.9922 | 0.9423 |
| hsa-miR-200a-3p | 0.9872 | 0.9468 | hsa-miR-340-5p | 0.98783 | 0.9107 | hsa-miR-4532 | 0.9927 | 0.9613 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| ha-miR-1305 | 0.98728 | 0.8947 | hsa-miR-3131 | 0.98788 | 0.8889 | hsa-miR-221-3p | 0.9938 | 0.977 |
| hsa-miR-890 | 0.98839 | 0.8723 | hsa-miR-4458 | 0.99005 | 0.938 | hsa-miR-450a-5p | 0.9938 | 0.9491 |
| hsa-miR-26a-5p | 0.98867 | 0.9514 | hsa-miR-553 | 0.99174 | 0.9334 | hsa-miR-1273d | 0.9955 | 0.9538 |
| hsa-miR-449a | 0.98895 | 0.9066 | hsa-miR-3196 | 0.99292 | 0.9232 | hsa-miR-320e | 0.9963 | 0.9778 |
| hsa-miR-3928 | 0.99091 | 0.8995 | hsa-miR-1252 | 0.99342 | 0.9236 | hsa-miR-365a-3p | 0.9967 | 0.9803 |
| hsa-miR-1913 | 0.99104 | 0.9241 | hsa-miR-938 | 0.99533 | 0.9443 | hsa-miR-371a-5p | 0.9967 | 0.9803 |
| hsa-miR-612 | 0.99148 | 0.8915 | hsa-let-7a-5p | 0.9975 | 0.9873 | hsa-miR-3690 | 0.9968 | 0.9678 |
| hsa-miR-3147 | 0.99367 | 0.9534 | hsa-miR-361-5p | 1.00123 | 0.9933 | hsa-miR-302b-3p | 0.9995 | 0.9956 |
| hsa-miR-3136-5p | 0.99724 | 0.9673 | hsa-miR-629-5p | 1.00218 | 0.9748 | hsa-miR-142-5p | 1.0002 | 0.9981 |
| hsa-miR-383 | 0.99746 | 0.9707 | hsa-miR-107 | 1.0038 | 0.9732 | hsa-miR-191-5p | 1.0025 | 0.9854 |
| hsa-miR-517c-3p?miR-519a- | 0.99763 | 0.9773 | hsa-miR-337-3p | 1.00518 | 0.9279 | hsa-miR-330-3p | 1.0032 | 0.9683 |
| hsa-miR-212-3p | 0.99888 | 0.982 | hsa-miR-210 | 1.00523 | 0.9498 | hsa-miR-1193 | 1.0049 | 0.9587 |
| hsa-miR-551a | 0.99937 | 0.9899 | hsa-miR-144-3p | 1.00627 | 0.9677 | hsa-miR-193a-3p | 1.0069 | 0.9495 |
| hsa-miR-301a-3p | 0.99944 | 0.9949 | hsa-miR-1286 | 1.01378 | 0.8432 | hsa-miR-10b-5p | 1.0074 | 0.9566 |
| hsa-miR-576-5p | 1.00059 | 0.996 | hsa-miR-877-5p | 1.01405 | 0.8686 | hsa-miR-125a-5p | 1.0087 | 0.9494 |
| hsa-miR-125a-3p | 1.00141 | 0.9852 | hsa-miR-600 | 1.01741 | 0.887 | hsa-miR-99a-5p | 1.0092 | 0.9567 |
| hsa-miR-4443 | 1.00348 | 0.9786 | hsa-miR-548t-5p | 1.01855 | 0.7764 | hsa-let-7f-5p | 1.0109 | 0.95 |
| hsa-miR-1290 | 1.00524 | 0.9724 | hsa-miR-3690 | 1.01992 | 0.7911 | hsa-miR-422a | 1.0118 | 0.8623 |
| hsa-miR-562 | 1.00627 | 0.9219 | hsa-miR-382-5p | 1.02019 | 0.7998 | hsa-miR-361-3p | 1.0119 | 0.8611 |
| hsa-miR-21-5p | 1.00693 | 0.9603 | hsa-miR-3195 | 1.03104 | 0.8727 | hsa-miR-376c | 1.0158 | 0.8726 |
| hsa-miR-30d-5p | 1.00729 | 0.9464 | hsa-miR-3175 | 1.03184 | 0.76 | hsa-miR-129-2-3p | 1.0161 | 0.8436 |
| hsa-miR-941 | 1.00742 | 0.9047 | hsa-miR-193a-3p | 1.03188 | 0.7587 | hsa-miR-548v | 1.0171 | 0.8547 |
| hsa-miR-15a-5p | 1.00825 | 0.9497 | hsa-miR-135b-5p | 1.03315 | 0.7435 | hsa-miR-151a-5p | 1.019 | 0.8623 |
| hsa-miR-192-5p | 1.0087 | 0.8649 | hsa-miR-425-5p | 1.03877 | 0.6823 | hsa-miR-181b-5p?miR-181d | 1.0229 | 0.788 |
| hsa-miR-892b | 1.01175 | 0.9175 | hsa-miR-151a-3p | 1.04061 | 0.5803 | hsa-miR-4461 | 1.0252 | 0.7002 |
| hsa-miR-147b | 1.012 | 0.858 | hsa-miR-1908 | 1.04193 | 0.7106 | hsa-miR-3131 | 1.0284 | 0.7627 |
| hsa-miR-1257 | 1.01212 | 0.8746 | hsa-miR-2110 | 1.04254 | 0.611 | hsa-miR-146a-5p | 1.0328 | 0.8001 |
| hsa-miR-3180 | 1.01242 | 0.8766 | hsa-miR-484 | 1.04274 | 0.4547 | hsa-miR-769-3p | 1.0348 | 0.6112 |
| hsa-miR-596 | 1.01273 | 0.9014 | hsa-miR-30b-5p | 1.04349 | 0.8134 | hsa-miR-3676-3p | 1.0366 | 0.7464 |
| hsa-miR-582-5p | 1.01275 | 0.9091 | hsa-miR-1226-3p | 1.04564 | 0.6148 | hsa-miR-190a | 1.0393 | 0.693 |
| hsa-miR-564 | 1.0135 | 0.8579 | hsa-miR-450b-3p | 1.04638 | 0.6959 | hsa-miR-483-3p | 1.0393 | 0.6879 |
| hsa-miR-498 | 1.01664 | 0.863 | hsa-miR-485-3p | 1.04692 | 0.6253 | hsa-miR-126-3p | 1.0405 | 0.8198 |
| hsa-miR-139-3p | 1.0177 | 0.7956 | hsa-miR-203 | 1.04832 | 0.6632 | hsa-miR-299-3p | 1.0409 | 0.7414 |
| hsa-miR-764 | 1.01891 | 0.8182 | hsa-miR-550a-5p | 1.04838 | 0.5521 | hsa-miR-337-5p | 1.0412 | 0.6385 |
| hsa-miR-573 | 1.01961 | 0.8305 | hsa-miR-514b-5p | 1.04867 | 0.5067 | hsa-miR-2053 | 1.0423 | 0.5401 |
| hsa-miR-516a-3p | 1.01963 | 0.7684 | hsa-miR-491-5p | 1.04893 | 0.5647 | hsa-miR-378a-3p?miR-3781 | 1.0427 | 0.7163 |
| hsa-miR-410 | 1.01972 | 0.7527 | hsa-miR-621 | 1.04955 | 0.4936 | hsa-miR-107 | 1.0435 | 0.7225 |
| hsa-miR-140-5p | 1.02101 | 0.8498 | hsa-miR-130b-3p | 1.05035 | 0.4229 | hsa-miR-603 | 1.0453 | 0.6216 |
| hsa-miR-330-5p | 1.02157 | 0.7477 | hsa-miR-3168 | 1.05144 | 0.6205 | hsa-miR-381 | 1.0454 | 0.5748 |
| hsa-miR-577 | 1.02282 | 0.7785 | hsa-miR-1288 | 1.05462 | 0.525 | hsa-miR-629-5p | 1.052 | 0.4887 |
| hsa-miR-3690 | 1.02317 | 0.7281 | hsa-miR-520b | 1.05982 | 0.4228 | hsa-miR-581 | 1.0548 | 0.5738 |
| hsa-miR-193a-3p | 1.02481 | 0.7863 | hsa-miR-532-5p | 1.06335 | 0.764 | hsa-miR-877-5p | 1.057 | 0.5365 |
| hsa-miR-146b-5p | 1.02518 | 0.8151 | hsa-miR-302a-3p | 1.06923 | 0.4786 | hsa-miR-139-3p | 1.0571 | 0.4952 |
| hsa-miR-524-3p | 1.02594 | 0.7721 | hsa-miR-383 | 1.06984 | 0.3905 | hsa-miR-4421 | 1.059 | 0.4902 |
| hsa-miR-374a-5p | 1.02648 | 0.8398 | hsa-miR-4455 | 1.07281 | 0.3845 | hsa-miR-196a-5p | 1.0616 | 0.4664 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-628-3p | 1.02729 | 0.714 | hsa-miR-196b-5p | 1.07565 | 0.4471 | hsa-miR-106b-5p | 1.0617 | 0.589 |
| hsa-miR-638 | 1.02794 | 0.7089 | hsa-miR-139-3p | 1.0758 | 0.3417 | hsa-miR-331-5p | 1.0657 | 0.4888 |
| hsa-miR-626 | 1.02835 | 0.7848 | hsa-miR-7-5p | 1.07688 | 0.4321 | hsa-miR-455-5p | 1.0658 | 0.4954 |
| hsa-miR-1909-3p | 1.02898 | 0.7237 | hsa-miR-622 | 1.07817 | 0.5021 | hsa-miR-197-3p | 1.0665 | 0.4606 |
| hsa-miR-1245b-5p | 1.02975 | 0.7085 | hsa-miR-1205 | 1.07905 | 0.3892 | hsa-miR-601 | 1.0667 | 0.692 |
| hsa-miR-569 | 1.03288 | 0.6721 | hsa-miR-515-5p | 1.07934 | 0.4344 | hsa-miR-670 | 1.0668 | 0.3681 |
| hsa-miR-548ak | 1.03411 | 0.6576 | hsa-miR-892b | 1.07993 | 0.5468 | hsa-miR-320a | 1.0671 | 0.4941 |
| hsa-miR-1286 | 1.03498 | 0.5748 | hsa-miR-1294 | 1.08157 | 0.2713 | hsa-miR-892b | 1.0674 | 0.63 |
| hsa-miR-134 | 1.03615 | 0.6441 | hsa-miR-548q | 1.08185 | 0.4539 | hsa-miR-569 | 1.0698 | 0.4628 |
| hsa-miR-361-5p | 1.03639 | 0.7832 | hsa-miR-128 | 1.08235 | 0.3071 | hsa-miR-519d | 1.0709 | 0.4525 |
| hsa-miR-23c | 1.03653 | 0.7424 | hsa-miR-5481 | 1.0843 | 0.3701 | hsa-miR-337-3p | 1.072 | 0.2546 |
| hsa-miR-670 | 1.03753 | 0.5374 | hsa-miR-548k | 1.08475 | 0.2493 | hsa-miR-383 | 1.0726 | 0.4012 |
| hsa-miR-519d | 1.03845 | 0.6192 | hsa-miR-151a-5p | 1.08674 | 0.4176 | hsa-miR-4647 | 1.0729 | 0.4024 |
| hsa-miR-367-3p | 1.03879 | 0.5742 | hsa-miR-188-5p | 1.08676 | 0.2146 | hsa-miR-367-3p | 1.0791 | 0.3501 |
| hsa-miR-548ad | 1.03888 | 0.5374 | hsa-miR-1224-5p | 1.08747 | 0.3582 | hsa-miR-510 | 1.0792 | 0.4039 |
| hsa-miR-1202 | 1.03909 | 0.6248 | hsa-miR-3182 | 1.09454 | 0.4881 | hsa-miR-30c-5p | 1.0799 | 0.6524 |
| hsa-miR-486-3p | 1.04377 | 0.6742 | hsa-miR-95 | 1.0959 | 0.198 | hsa-let-7b-5p | 1.0807 | 0.5663 |
| hsa-miR-208a | 1.04663 | 0.6111 | hsa-miR-890 | 1.09663 | 0.2639 | hsa-miR-553 | 1.0807 | 0.4624 |
| hsa-miR-3196 | 1.04706 | 0.4816 | hsa-miR-3676-3p | 1.09698 | 0.3779 | hsa-miR-548am-3p | 1.0814 | 0.4381 |
| hsa-miR-660-5p | 1.04747 | 0.6149 | hsa-miR-604 | 1.09738 | 0.312 | hsa-miR-34c-3p | 1.0838 | 0.4174 |
| hsa-miR-2276 | 1.04751 | 0.522 | hsa-miR-320e | 1.09932 | 0.4561 | hsa-miR-514b-5p | 1.0847 | 0.2865 |
| hsa-miR-2682-5p | 1.04912 | 0.534 | hsa-miR-2117 | 1.09951 | 0.2509 | hsa-miR-210 | 1.0865 | 0.3483 |
| hsa-miR-432-5p | 1.0494 | 0.5044 | hsa-miR-511 | 1.10043 | 0.2681 | hsa-miR-96-5p | 1.0866 | 0.4574 |
| hsa-miR-1287 | 1.04981 | 0.3723 | hsa-miR-627 | 1.10058 | 0.1269 | hsa-miR-663b | 1.0884 | 0.5685 |
| hsa-miR-18a-5p | 1.05079 | 0.3594 | hsa-miR-569 | 1.10495 | 0.2506 | hsa-let-7a-5p | 1.0887 | 0.6102 |
| hsa-miR-196a-5p | 1.05109 | 0.4665 | hsa-miR-670 | 1.1068 | 0.1364 | hsa-miR-4488 | 1.0908 | 0.6111 |
| hsa-miR-518b | 1.05125 | 0.5167 | hsa-miR-411-5p | 1.10829 | 0.1434 | hsa-miR-548x-3p | 1.092 | 0.1723 |
| hsa-miR-1299 | 1.05132 | 0.6237 | hsa-miR-578 | 1.1098 | 0.1038 | hsa-miR-93-5p | 1.0956 | 0.4768 |
| hsa-miR-495 | 1.05238 | 0.4235 | hsa-miR-1260b | 1.10989 | 0.3609 | hsa-miR-199a-5p | 1.0983 | 0.5314 |
| hsa-miR-16-5p | 1.05457 | 0.7057 | hsa-miR-449a | 1.11082 | 0.3282 | hsa-miR-4741 | 1.107 | 0.1573 |
| hsa-miR-1178 | 1.05511 | 0.6021 | hsa-miR-376b | 1.11204 | 0.1244 | hsa-miR-192-5p | 1.1087 | 0.0955 |
| hsa-miR-4448 | 1.0566 | 0.5445 | hsa-miR-519d | 1.11209 | 0.2184 | hsa-miR-890 | 1.1095 | 0.2362 |
| hsa-miR-3676-3p | 1.05827 | 0.5413 | hsa-miR-196a-5p | 1.11584 | 0.1593 | hsa-miR-374b-5p | 1.1097 | 0.4804 |
| hsa-miR-550a-5p | 1.05837 | 0.4205 | hsa-miR-3161 | 1.11694 | 0.2067 | hsa-miR-151a-3p | 1.111 | 0.1718 |
| hsa-miR-185-5p | 1.05923 | 0.3065 | hsa-miR-192-5p | 1.11837 | 0.0561 | hsa-miR-638 | 1.1145 | 0.2241 |
| hsa-miR-484 | 1.06042 | 0.2383 | hsa-miR-367-3p | 1.12096 | 0.1394 | hsa-miR-142-3p | 1.1159 | 0.617 |
| hsa-miR-576-3p | 1.06339 | 0.6063 | hsa-miR-502-5p | 1.12695 | 0.1759 | hsa-miR-526a?miR-520c-5p? | 1.1185 | 0.2165 |
| hsa-miR-194-5p | 1.06388 | 0.3577 | hsa-miR-891a | 1.12738 | 0.1188 | hsa-miR-1202 | 1.1207 | 0.2286 |
| hsa-miR-25-3p | 1.06439 | 0.3626 | hsa-miR-548i | 1.13004 | 0.2572 | hsa-miR-297 | 1.121 | 0.1325 |
| hsa-miR-499a-3p | 1.06446 | 0.4772 | hsa-miR-496 | 1.13055 | 0.1337 | hsa-miR-449a | 1.1232 | 0.3087 |
| hsa-miR-656 | 1.0651 | 0.3901 | hsa-miR-572 | 1.13185 | 0.1951 | hsa-miR-100-5p | 1.1236 | 0.4917 |
| hsa-miR-587 | 1.06598 | 0.299 | hsa-miR-641 | 1.1324 | 0.0601 | hsa-miR-92a-3p | 1.1247 | 0.28 |
| hsa-miR-151a-5p | 1.06647 | 0.4782 | hsa-miR-542-3p | 1.13491 | 0.0822 | hsa-miR-1183 | 1.1266 | 0.3514 |
| hsa-miR-34c-3p | 1.06774 | 0.4283 | hsa-miR-30d-5p | 1.13544 | 0.301 | hsa-miR-1224-5p | 1.1267 | 0.2197 |
| hsa-miR-412 | 1.07032 | 0.3075 | hsa-miR-21-5p | 1.13566 | 0.4183 | hsa-miR-30d-5p | 1.1272 | 0.3578 |
| hsa-miR-197-3p | 1.07078 | 0.3479 | hsa-miR-197-3p | 1.14199 | 0.1098 | hsa-miR-21-5p | 1.1278 | 0.4706 |
| hsa-miR-544a | 1.07111 | 0.2608 | hsa-miR-548g-3p | 1.14204 | 0.1052 | hsa-miR-1275 | 1.1287 | 0.1227 |
| hsa-miR-491-5p | 1.07395 | 0.3326 | hsa-miR-541-3p | 1.14281 | 0.2713 | hsa-miR-412 | 1.1317 | 0.124 |
| hsa-miR-2110 | 1.07478 | 0.3216 | hsa-miR-638 | 1.14562 | 0.1075 | hsa-miR-1255b-5p | 1.1388 | 0.175 |
| hsa-miR-335-5p | 1.0751 | 0.3498 | hsa-miR-758 | 1.14772 | 0.1127 | hsa-miR-548t-5p | 1.1398 | 0.0613 |
| hsa-miR-647 | 1.07538 | 0.3343 | hsa-miR-142-5p | 1.149 | 0.1466 | hsa-miR-500a-5p?miR-501-5 | 1.1415 | 0.0603 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-384 | 1.07602 | 0.4199 | hsa-miR-597 | 1.15015 | 0.0643 | hsa-miR-134 | 1.1457 | 0.1441 |
| hsa-miR-885-5p | 1.07641 | 0.2924 | hsa-miR-1238 | 1.15053 | 0.0802 | hsa-miR-587 | 1.1513 | 0.0593 |
| hsa-miR-600 | 1.07793 | 0.486 | hsa-miR-31-5p | 1.15316 | 0.0779 | hsa-miR-604 | 1.1549 | 0.1422 |
| hsa-miR-362-5p | 1.07801 | 0.3012 | hsa-miR-3185 | 1.15415 | 0.0901 | hsa-miR-520b | 1.1568 | 0.0621 |
| hsa-miR-665 | 1.08141 | 0.3907 | hsa-miR-635 | 1.1561 | 0.1199 | hsa-miR-1257 | 1.1574 | 0.1152 |
| hsa-miR-1275 | 1.08173 | 0.2273 | hsa-miR-936 | 1.15707 | 0.0744 | hsa-miR-196b-5p | 1.1596 | 0.1489 |
| hsa-miR-132-3p | 1.08238 | 0.3874 | hsa-miR-34c-3p | 1.15727 | 0.1216 | hsa-miR-641 | 1.1653 | 0.0302 |
| hsa-miR-200b-3p | 1.08312 | 0.7339 | hsa-miR-1200 | 1.16154 | 0.0796 | hsa-miR-335-5p | 1.1672 | 0.0993 |
| hsa-miR-494 | 1.08321 | 0.7285 | hsa-miR-762 | 1.16285 | 0.0474 | hsa-miR-541-3p | 1.1691 | 0.2259 |
| hsa-miR-654-5p | 1.08393 | 0.2684 | hsa-miR-1273e | 1.16307 | 0.4026 | hsa-miR-524-3p | 1.1692 | 0.1446 |
| hsa-miR-216a | 1.08537 | 0.349 | hsa-miR-129-2-3p | 1.164 | 0.0503 | hsa-miR-1180 | 1.1714 | 0.1032 |
| hsa-miR-516a-5p | 1.0857 | 0.5371 | hsa-miR-1202 | 1.1645 | 0.0899 | hsa-miR-382-5p | 1.1715 | 0.063 |
| hsa-miR-566 | 1.08683 | 0.1804 | hsa-miR-767-3p | 1.16771 | 0.1599 | hsa-miR-3151 | 1.1766 | 0.2653 |
| hsa-miR-1234 | 1.08802 | 0.4787 | hsa-miR-497-5p | 1.17009 | 0.2799 | hsa-miR-504 | 1.1768 | 0.1087 |
| hsa-miR-526a?miR-520c-5p? | 1.08817 | 0.2627 | hsa-miR-664-3p | 1.17017 | 0.176 | hsa-miR-515-3p | 1.1836 | 0.0414 |
| hsa-miR-1303 | 1.08895 | 0.6728 | hsa-miR-1257 | 1.17139 | 0.0714 | hsa-miR-516a-3p | 1.1893 | 0.0324 |
| hsa-miR-761 | 1.09222 | 0.4538 | hsa-miR-548d-5p | 1.17155 | 0.0852 | hsa-miR-1294 | 1.1903 | 0.024 |
| hsa-miR-548ag | 1.09315 | 0.3109 | hsa-miR-155-5p | 1.17583 | 0.0651 | hsa-miR-548g-3p | 1.1947 | 0.0425 |
| hsa-miR-301b | 1.09334 | 0.3664 | hsa-miR-191-5p | 1.18001 | 0.2107 | hsa-miR-4454 | 1.1953 | 0.2636 |
| hsa-miR-448 | 1.09335 | 0.2066 | hsa-miR-563 | 1.18507 | 0.1538 | hsa-miR-548d-5p | 1.1953 | 0.0682 |
| hsa-miR-423-3p | 1.0935 | 0.0886 | hsa-miR-548n | 1.18543 | 0.0447 | hsa-miR-502-5p | 1.198 | 0.0562 |
| hsa-miR-148b-3p | 1.09351 | 0.2887 | hsa-miR-1973 | 1.18692 | 0.0609 | hsa-miR-22-3p | 1.1981 | 0.2657 |
| hsa-miR-924 | 1.09646 | 0.2791 | hsa-miR-134 | 1.18709 | 0.0525 | hsa-miR-376b | 1.2027 | 0.0136 |
| hsa-miR-568 | 1.0981 | 0.3176 | hsa-miR-548am-3p | 1.19409 | 0.0657 | hsa-miR-1200 | 1.2033 | 0.0423 |
| hsa-miR-3151 | 1.09854 | 0.4385 | hsa-miR-514a-3p | 1.19528 | 0.0294 | hsa-miR-486-3p | 1.2044 | 0.1323 |
| hsa-miR-3934 | 1.09913 | 0.1938 | hsa-miR-612 | 1.19691 | 0.014 | hsa-miR-612 | 1.2072 | 0.0152 |
| hsa-miR-1539 | 1.09995 | 0.1558 | hsa-miR-510 | 1.19719 | 0.0399 | hsa-miR-498 | 1.2074 | 0.1049 |
| hsa-miR-1205 | 1.10016 | 0.224 | hsa-miR-524-3p | 1.19951 | 0.0731 | hsa-miR-378b | 1.2079 | 0.0263 |
| hsa-miR-323a-3p | 1.10052 | 0.1961 | hsa-miR-1273d | 1.19973 | 0.0161 | hsa-miR-621 | 1.215 | 0.0117 |
| hsa-miR-518c-3p | 1.10129 | 0.3015 | hsa-miR-449c-5p | 1.19997 | 0.0133 | hsa-miR-5481 | 1.2185 | 0.0427 |
| hsa-miR-320e | 1.10345 | 0.3818 | hsa-miR-613 | 1.20146 | 0.0218 | hsa-miR-762 | 1.219 | 0.0152 |
| hsa-miR-548am-3p | 1.10426 | 0.2401 | hsa-miR-1193 | 1.20585 | 0.0402 | hsa-miR-630 | 1.2198 | 0.3633 |
| hsa-miR-1277-3p | 1.10537 | 0.2115 | hsa-miR-944 | 1.20636 | 0.0514 | hsa-miR-144-3p | 1.2201 | 0.2275 |
| hsa-miR-548a-3p | 1.10666 | 0.1136 | hsa-miR-1322 | 1.208 | 0.2103 | hsa-miR-3161 | 1.2201 | 0.035 |
| hsa-miR-508-3p | 1.1088 | 0.2365 | hsa-miR-3605-5p | 1.20972 | 0.0225 | hsa-miR-511 | 1.2219 | 0.0318 |
| hsa-miR-510 | 1.10934 | 0.1753 | hsa-miR-548an | 1.21068 | 0.0102 | hsa-miR-421 | 1.2246 | 0.1195 |
| hsa-miR-15b-5p | 1.1094 | 0.3606 | hsa-miR-412 | 1.21125 | 0.0131 | hsa-miR-924 | 1.2268 | 0.0483 |
| hsa-miR-454-3p | 1.11064 | 0.2589 | hsa-miR-516a-3p | 1.21267 | 0.0123 | hsa-miR-2054 | 1.233 | 0.1213 |
| hsa-miR-1255b-5p | 1.11373 | 0.1774 | hsa-miR-548d-3p | 1.21463 | 0.1382 | hsa-miR-301b | 1.2334 | 0.0801 |
| hsa-miR-3182 | 1.11674 | 0.3393 | hsa-miR-526a?miR-520c-5p? | 1.2171 | 0.0238 | hsa-miR-767-3p | 1.2448 | 0.0635 |
| hsa-miR-188-5p | 1.11797 | 0.0627 | hsa-miR-1275 | 1.22092 | 0.0083 | hsa-miR-371a-3p | 1.2516 | 0.0073 |
| hsa-miR-297 | 1.12112 | 0.0722 | hsa-miR-371a-5p | 1.22316 | 0.1173 | hsa-miR-485-3p | 1.2531 | 0.0271 |
| hsa-miR-622 | 1.12253 | 0.2463 | hsa-miR-548ah-5p | 1.22483 | 0.0731 | hsa-miR-302a-3p | 1.2535 | 0.0276 |
| hsa-miR-302e | 1.12332 | 0.0648 | hsa-miR-4431 | 1.22707 | 0.0606 | hsa-miR-596 | 1.2572 | 0.0661 |
| hsa-miR-19a-3p | 1.12386 | 0.2563 | hsa-miR-587 | 1.22728 | 0.0045 | hsa-miR-508-3p | 1.258 | 0.031 |
| hsa-miR-766-3p | 1.12453 | 0.0944 | hsa-miR-498 | 1.22748 | 0.0623 | hsa-miR-183-5p | 1.2592 | 0.0259 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-92a-3p | 1.12681 | 0.1893 | hsa-miR-335-5p | 1.25483 | 0.0117 | hsa-miR-764 | 1.2607 | 0.021 |
| hsa-miR-508-5p | 1.13265 | 0.1552 | hsa-miR-302b-3p | 1.25595 | 0.0174 | hsa-miR-135b-5p | 1.2626 | 0.0312 |
| hsa-miR-423-5p | 1.13314 | 0.069 | hsa-miR-297 | 1.25673 | 0.0021 | hsa-miR-944 | 1.2627 | 0.0234 |
| hsa-miR-598 | 1.13823 | 0.2308 | hsa-miR-486-3p | 1.25706 | 0.0511 | hsa-miR-548ag | 1.2653 | 0.0286 |
| hsa-miR-363-3p | 1.13885 | 0.2874 | hsa-miR-581 | 1.25919 | 0.0123 | hsa-miR-223-3p | 1.2656 | 0.1899 |
| hsa-miR-340-5p | 1.13924 | 0.1814 | hsa-miR-1244 | 1.2611 | 0.0035 | hsa-miR-664-3p | 1.2668 | 0.0573 |
| hsa-miR-129-2-3p | 1.14559 | 0.0479 | hsa-miR-149-5p | 1.26297 | 0.0606 | hsa-miR-302f | 1.2686 | 0.0025 |
| hsa-miR-519e-3p | 1.14585 | 0.0505 | hsa-miR-92a-3p | 1.26733 | 0.0235 | hsa-miR-548i | 1.2693 | 0.0403 |
| hsa-miR-1208 | 1.14691 | 0.0374 | hsa-miR-1246 | 1.26786 | 0.0329 | hsa-miR-410 | 1.2701 | 0.0022 |
| hsa-miR-578 | 1.14814 | 0.0164 | hsa-miR-1255b-5p | 1.26827 | 0.0102 | hsa-miR-575 | 1.2703 | 0.2163 |
| hsa-miR-142-5p | 1.14872 | 0.1026 | hsa-miR-922 | 1.26837 | 0.0195 | hsa-miR-544a | 1.2712 | 0.0017 |
| hsa-miR-3168 | 1.15141 | 0.1199 | hsa-miR-1264 | 1.27188 | 0.0104 | hsa-miR-106a-5p?miR-17-5p | 1.2719 | 0.1073 |
| hsa-miR-424-5p | 1.1535 | 0.2223 | hsa-miR-631 | 1.27273 | 0.0062 | hsa-miR-376a-3p | 1.2746 | 0.0827 |
| hsa-miR-504 | 1.15386 | 0.0913 | hsa-miR-596 | 1.27319 | 0.0404 | hsa-miR-936 | 1.288 | 0.0045 |
| hsa-miR-658 | 1.15814 | 0.0869 | hsa-miR-548aa | 1.27905 | 0.1386 | hsa-miR-1178 | 1.3006 | 0.037 |
| hsa-miR-371a-3p | 1.16525 | 0.0265 | hsa-miR-764 | 1.28458 | 0.0086 | hsa-miR-1915-3p | 1.3012 | 0.1537 |
| hsa-miR-450b-5p | 1.16625 | 0.0478 | hsa-miR-3151 | 1.29255 | 0.0649 | hsa-miR-922 | 1.3081 | 0.0133 |
| hsa-miR-128 | 1.1672 | 0.0271 | hsa-miR-616-3p | 1.2934 | 0.0114 | hsa-miR-1260b | 1.3145 | 0.027 |
| hsa-miR-20a-5p?miR-20b-5p | 1.16878 | 0.2296 | hsa-miR-410 | 1.29514 | 0.0005 | hsa-miR-25-3p | 1.3189 | 0.0013 |
| hsa-miR-1252 | 1.16907 | 0.013 | hsa-miR-29c-3p | 1.29989 | 0.1558 | hsa-miR-149-5p | 1.3259 | 0.0336 |
| hsa-miR-302f | 1.16997 | 0.015 | hsa-miR-1228-3p | 1.30829 | 0.0011 | hsa-miR-411-5p | 1.3282 | 0.0003 |
| hsa-miR-421 | 1.17012 | 0.1469 | hsa-miR-216b | 1.31174 | 0.0003 | hsa-miR-542-3p | 1.3286 | 0.0005 |
| hsa-miR-758 | 1.17605 | 0.0367 | hsa-miR-302d-3p | 1.31527 | <.0001 | hsa-miR-3136-5p | 1.3334 | 0.0008 |
| hsa-miR-191-5p | 1.17701 | 0.1645 | hsa-miR-935 | 1.31633 | 0.0124 | hsa-miR-548q | 1.3404 | 0.0108 |
| ha-miR-7-5p | 1.17781 | 0.0535 | hsa-miR-942 | 1.31869 | 0.0027 | hsa-miR-3147 | 1.3417 | 0.0278 |
| hsa-miR-130b-3p | 1.18037 | 0.0033 | hsa-miR-579 | 1.31883 | 0.0048 | hsa-miR-31-5p | 1.3436 | 0.0009 |
| hsa-miR-429 | 1.18081 | 0.3073 | hsa-miR-1260a | 1.32174 | 0.0766 | hsa-miR-302d-3p | 1.3463 | <.0001 |
| hsa-miR-802 | 1.18407 | 0.0662 | hsa-miR-3136-5p | 1.32974 | 0.0005 | hsa-miR-1246 | 1.3496 | 0.0119 |
| hsa-miR-1288 | 1.18449 | 0.0255 | hsa-miR-3147 | 1.33318 | 0.0226 | hsa-miR-613 | 1.3535 | 0.0006 |
| hsa-miR-614 | 1.18719 | 0.0727 | hsa-miR-924 | 1.34512 | 0.003 | hsa-miR-2117 | 1.3555 | 0.001 |
| hsa-miR-33a-5p | 1.1875 | 0.0099 | hsa-miR-548y | 1.34667 | 0.0492 | hsa-miR-572 | 1.3599 | 0.0035 |
| hsa-miR-378b | 1.18839 | 0.0154 | hsa-miR-301b | 1.34854 | 0.0094 | hsa-miR-496 | 1.3613 | 0.0007 |
| hsa-miR-548aj-3p | 1.19351 | 0.0458 | hsa-miR-4286 | 1.35165 | 0.2898 | hsa-miR-29c-3p | 1.3675 | 0.1115 |
| hsa-miR-615-5p | 1.19365 | 0.1238 | hsa-miR-504 | 1.3579 | 0.002 | hsa-miR-19b-3p | 1.3688 | 0.0718 |
| hsa-miR-581 | 1.19377 | 0.0285 | hsa-miR-570-3p | 1.35797 | 0.0078 | hsa-miR-562 | 1.3735 | 0.0001 |
| hsa-miR-590-5p | 1.19793 | 0.0026 | hsa-miR-1268b | 1.3582 | 0.002 | hsa-miR-802 | 1.3784 | 0.0045 |
| hsa-miR-30b-5p | 1.1987 | 0.2592 | hsa-miR-544a | 1.36155 | <.0001 | hsa-miR-1260a | 1.3851 | 0.0522 |
| hsa-miR-1193 | 1.19995 | 0.0246 | hsa-miR-1178 | 1.37223 | 0.0085 | hsa-miR-216b | 1.3934 | <.0001 |
| hsa-miR-1238 | 1.20141 | 0.011 | hsa-miR-489 | 1.38103 | 0.0002 | hsa-miR-1244 | 1.398 | 0.0001 |
| hsa-miR-1273d | 1.20516 | 0.0058 | hsa-miR-562 | 1.38213 | <.0001 | hsa-miR-579 | 1.4017 | 0.0013 |
| hsa-miR-19b-3p | 1.21303 | 0.1808 | hsa-miR-548ag | 1.38318 | 0.0018 | hsa-miR-1322 | 1.412 | 0.0338 |
| hsa-miR-627 | 1.21475 | 0.0008 | hsa-miR-18b-5p | 1.38553 | 0.0077 | hsa-miR-573 | 1.4132 | 0.0024 |
| hsa-miR-663a | 1.21558 | 0.0461 | hsa-miR-663b | 1.38979 | 0.0218 | hsa-miR-577 | 1.4145 | 0.0007 |
| hsa-miR-95 | 1.21715 | 0.0027 | hsa-miR-1206 | 1.39039 | 0.0013 | hsa-miR-514a-3p | 1.4162 | 0.0001 |
| hsa-miR-517a-3p | 1.21862 | 0.0377 | hsa-miR-508-3p | 1.39488 | 0.0013 | hsa-miR-892a | 1.4259 | 0.0005 |
| hsa-miR-3175 | 1.22147 | 0.0313 | hsa-miR-25-3p | 1.40385 | <.0001 | hsa-miR-593-3p | 1.4283 | 0.0083 |
| hsa-miR-892a | 1.2248 | 0.0141 | hsa-miR-182-5p | 1.40985 | 0.0087 | hsa-miR-181a-5p | 1.4317 | 0.0242 |
| hsa-miR-548an | 1.22589 | 0.0023 | hsa-miR-548ab | 1.4142 | 0.0412 | hsa-miR-576-3p | 1.4504 | 0.0118 |
| hsa-miR-371a-5p | 1.22724 | 0.0731 | hsa-miR-106b-5p | 1.42311 | 0.0013 | hsa-miR-363-3p | 1.4607 | 0.0118 |
| hsa-miR-548k | 1.23291 | 0.0014 | hsa-miR-4531 | 1.42635 | 0.0003 | hsa-miR-155-5p | 1.4637 | 0.0001 |
| hsa-miR-891a | 1.23345 | 0.0029 | hsa-miR-421 | 1.43292 | 0.0044 | hsa-miR-429 | 1.4637 | 0.0543 |
| hsa-miR-1973 | 1.23646 | 0.0099 | hsa-miR-378b | 1.43551 | <.0001 | hsa-miR-1245b-5p | 1.4667 | 0.0002 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-362-3p | 1.24436 | 0.0227 | hsa-miR-520h | 1.43753 | 0.0001 | hsa-miR-3195 | 1.469 | 0.0621 |
| hsa-miR-635 | 1.24932 | 0.0084 | hsa-miR-573 | 1.44089 | 0.0008 | hsa-miR-3185 | 1.4797 | <.0004 |
| hsa-miR-3184-5p | 1.25619 | 0.006 | hsa-miR-577 | 1.44676 | 0.0002 | hsa-miR-32-5p | 1.4894 | 0.0037 |
| hsa-miR-302b-3p | 1.25664 | 0.0075 | hsa-miR-520d-5p?miR-518a- | 1.45297 | 0.0018 | hsa-miR-517c-3p?miR-519a- | 1.4897 | 0.0002 |
| hsa-miR-106a-5p?miR-17-5p | 1.25898 | 0.0654 | hsa-miR-548ai | 1.45619 | 0.0003 | hsa-miR-4531 | 1.4979 | 0.0001 |
| hsa-miR-1827 | 1.25962 | 0.0017 | hsa-miR-1279 | 1.45798 | <.0001 | hsa-miR-616-3p | 1.5026 | 0.0003 |
| hsa-miR-370 | 1.25977 | 0.0467 | hsa-miR-371a-3p | 1.45845 | <.0001 | hsa-miR-548d-3p | 1.5065 | 0.0043 |
| hsa-miR-1273e | 1.26465 | 0.1444 | hsa-miR-720 | 1.48248 | 0.0181 | hsa-miR-942 | 1.5277 | <.0001 |
| hsa-miR-203 | 1.26731 | 0.0163 | hsa-miR-302f | 1.48419 | <.0001 | hsa-miR-1323 | 1.5307 | <.0001 |
| hsa-miR-1915-3p | 1.27027 | 0.1207 | hsa-miR-517c-3p?miR-519a- | 1.48621 | 0.0001 | hsa-miR-548ah-5p | 1.531 | 0.0007 |
| hsa-miR-580 | 1.27429 | 0.0058 | hsa-miR-1323 | 1.50795 | <.0001 | hsa-miR-570-3p | 1.5329 | 0.0006 |
| hsa-ma-1226-3p | 1.27535 | 0.003 | hsa-miR-1245b-5p | 1.51034 | <.0001 | hsa-miR-497-5p | 1.5345 | 0.0071 |
| hsa-miR-9-5p | 1.27535 | 0.0205 | hsa-miR-574-5p | 1.51405 | 0.0051 | hsa-miR-1228-3p | 1.5372 | <.0001 |
| hsa-miR-663b | 1.27693 | 0.0524 | hsa-miR-513a-3p | 1.52259 | 0.0011 | hsa-miR-548n | 1.5422 | <.0001 |
| hsa-miR-938 | 1.27983 | 0.0001 | hsa-miR-1276 | 1.53513 | 0.031 | hsa-miR-548y | 1.5616 | 0.0064 |
| hsa-miR-325 | 1.28039 | 0.0181 | hsa-miR-550b-3p | 1.54097 | <.0001 | hsa-miR-720 | 1.5634 | 0.0118 |
| hsa-miR-219-1-3p | 1.28152 | 0.0276 | hsa-miR-576-3p | 1.54229 | 0.0022 | hsa-miR-19a-3p | 1.5669 | 0.0006 |
| hsa-miR-3605-5p | 1.28898 | 0.0009 | hsa-miR-888-5p | 1.55099 | 0.0031 | hsa-miR-489 | 1.5792 | <.0001 |
| hsa-miR-575 | 1.29601 | 0.1098 | hsa-miR-548a-5p | 1.5683 | <.0001 | hsa-miR-1913 | 1.5939 | 0.0001 |
| hsa-miR-654-3p | 1.29972 | 0.0057 | hsa-miR-93-5p | 1.5733 | 0.0004 | hsa-miR-20a-5p?miR-20b-5p | 1.6015 | 0.0035 |
| hsa-miR-630 | 1.30837 | 0.1428 | hsa-miR-1913 | 1.57965 | <.0001 | hsa-miR-1268b | 1.6019 | <.0001 |
| hsa-miR-4455 | 1.31987 | 0.0003 | hsa-miR-1179 | 1.58098 | <.0001 | hsa-miR-597 | 1.6125 | <.0001 |
| hsa-miR-659-3p | 1.32046 | 0.001 | hsa-miR-601 | 1.59139 | 0.0037 | hsa-miR-520d-5p?miR-518a- | 1.6126 | 0.0002 |
| hsa-miR-631 | 1.32484 | 0.0004 | hsa-miR-630 | 1.59598 | 0.0262 | hsa-miR-375 | 1.6127 | 0.0491 |
| hsa-miR-425-5p | 1.32618 | 0.0011 | hsa-miR-106a-5p?miR-17-5p | 1.60127 | 0.0013 | hsa-miR-548ai | 1.6175 | <.0001 |
| hsa-miR-450b-3p | 1.33027 | 0.0073 | hsa-miR-200a-3p | 1.61908 | 0.0311 | hsa-miR-520h | 1.6241 | <.0001 |
| hsa-miR-4431 | 1.33974 | 0.0032 | hsa-miR-802 | 1.63217 | <.0001 | hsa-miR-200a-3p | 1.6401 | 0.0368 |
| hsa-miR-106b-5p | 1.34038 | 0.0025 | hsa-miR-2116-5p | 1.63751 | 0.001 | hsa-miR-513a-3p | 1.6504 | 0.0003 |
| hsa-miR-1908 | 1.37633 | 0.0019 | hsa-miR-575 | 1.64634 | 0.00578 | hsa-miR-1264 | 1.6585 | <.0001 |
| hsa-miR-4286 | 1.394 | 0.1887 | hsa-miR-1915-3p | 1.65293 | 0.005 | hsa-miR-1179 | 1.6815 | <.0001 |
| hsa-miR-515-3p | 1.40777 | <.0001 | hsa-miR-19b-3p | 1.66034 | 0.0027 | hsa-miR-935 | 1.6999 | <.0001 |
| hsa-miR-606 | 1.42222 | 0.0011 | ha-miR-363-3p | 1.66351 | 0.0005 | hsa-miR-18b-5p | 1.7129 | <.0001 |
| hsa-miR-4458 | 1.4324 | 0.0026 | hsa-miR-515-3p | 1.66629 | <.0001 | hsa-miR-548a-5p | 1.7203 | <.0001 |
| hsa-miR-93-5p | 1.43606 | 0.0013 | hsa-miR-137 | 1.72395 | 0.1104 | hsa-miR-548ab | 1.7583 | 0.0023 |
| hsa-miR-449c-5p | 1.44412 | <.0001 | hsa-miR-429 | 1.72835 | 0.0041 | hsa-miR-550b-3p | 1.7702 | <.0001 |
| hsa-miR-548p | 1.45236 | 0.0005 | hsa-miR-892a | 1.74648 | <.0001 | hsa-miR-888-5p | 1.7787 | 0.0003 |
| hsa-miR-183-5p | 1.453 | <.0001 | hsa-miR-19a-3p | 1.76095 | <.0001 | hsa-miR-1279 | 1.8332 | <.0001 |
| hsa-miR-1185-5p | 1.45658 | 0.0001 | hsa-miR-549 | 1.77031 | 0.0141 | hsa-miR-135a-5p | 1.8694 | 0.0029 |
| hsa-miR-548al | 1.47105 | <.0001 | hsa-miR-1268a | 1.79717 | <.0001 | hsa-miR-548aa | 1.8924 | 0.0006 |
| hsa-miR-563 | 1.49178 | 0.0003 | hsa-miR-96-5p | 1.79891 | <.0001 | hsa-miR-574-5p | 1.9046 | <.0001 |
| hsa-miR-601 | 1.49193 | 0.0047 | hsa-miR-183-5p | 1.82967 | <.0001 | hsa-miR-1268a | 1.9119 | <.0001 |
| hsa-miR-1206 | 1.49602 | <.0001 | hsa-miR-135a-5p | 1.83599 | 0.0022 | hsa-miR-2116-5p | 1.963 | <.0001 |
| hsa-miR-515-5p | 1.49971 | <.0001 | hsa-miR-378e | 1.8429 | 0.0089 | hsa-miR-1290 | 2.1367 | 0.0001 |
| hsa-miR-4425 | 1.55984 | 0.0006 | hsa-miR-20a-5p?miR-20b-5p | 1.87176 | <.0001 | hsa-miR-1276 | 2.1448 | 0.0005 |
| hsa-miR-4284 | 1.56506 | <.0001 | hsa-miR-1972 | 1.99892 | 0.0212 | hsa-miR-200b-3p | 2.2761 | 0.005 |
| hsa-miR-32-5p | 1.57407 | 0.0001 | hsa-miR-1290 | 2.14789 | <.0001 | hsa-miR-148a-3p | 2.2933 | 0.0007 |

TABLE 4-continued

Comparison of miRNA expression levels from tumor tissue, epithelium, and stroma

| miR_ID | Ratio: Tu vs Ep | p-value: Tu vs Ep | miR_ID | Ratio: Tu vs St | p-value: Tu vs St | miR_ID | Ratio: Ep vs St | p-value: Ep vs St |
|---|---|---|---|---|---|---|---|---|
| hsa-miR-532-5p | 1.57499 | 0.0149 | hsa-miR-1253 | 2.27081 | 0.0066 | hsa-miR-1305 | 2.6512 | <.0001 |
| hsa-miR-96-5p | 1.65561 | <.0001 | hsa-miR-32-5p | 2.34437 | <.0001 | hsa-miR-205-5p | 2.6739 | 0.0443 |
| hsa-miR-4508 | 1.68748 | <.0001 | hsa-miR-200b-3p | 2.46532 | 0.0013 | hsa-miR-1972 | 2.7586 | 0.0019 |
| hsa-miR-148a-3p | 1.74273 | 0.0054 | hsa-miR-1305 | 2.61745 | <.0001 | hsa-miR-141-3p | 2.9576 | <.0001 |
| hsa-miR-141-3p | 1.76447 | 0.0041 | hsa-miR-1283 | 3.45147 | 0.0114 | hsa-miR-200c-3p | 3.0052 | 0.0002 |
| hsa-miR-182-5p | 1.91808 | <.0001 | hsa-miR-375 | 3.85162 | <.0001 | hsa-miR-378e | 3.5063 | <.0001 |
| hsa-miR-200c-3p | 1.99681 | 0.0038 | hsa-miR-148a-3p | 3.99653 | <.0001 | hsa-miR-549 | 3.5135 | <.0001 |
| hsa-miR-137 | 2.07477 | 0.0173 | hsa-miR-141-3p | 5.21869 | <.0001 | hsa-miR-1253 | 5.3773 | <.0001 |
| hsa-miR-375 | 2.38831 | <.0001 | hsa-miR-200c-3p | 6.00079 | <.0001 | hsa-miR-1283 | 13.122 | <.0001 |

Figure 2:
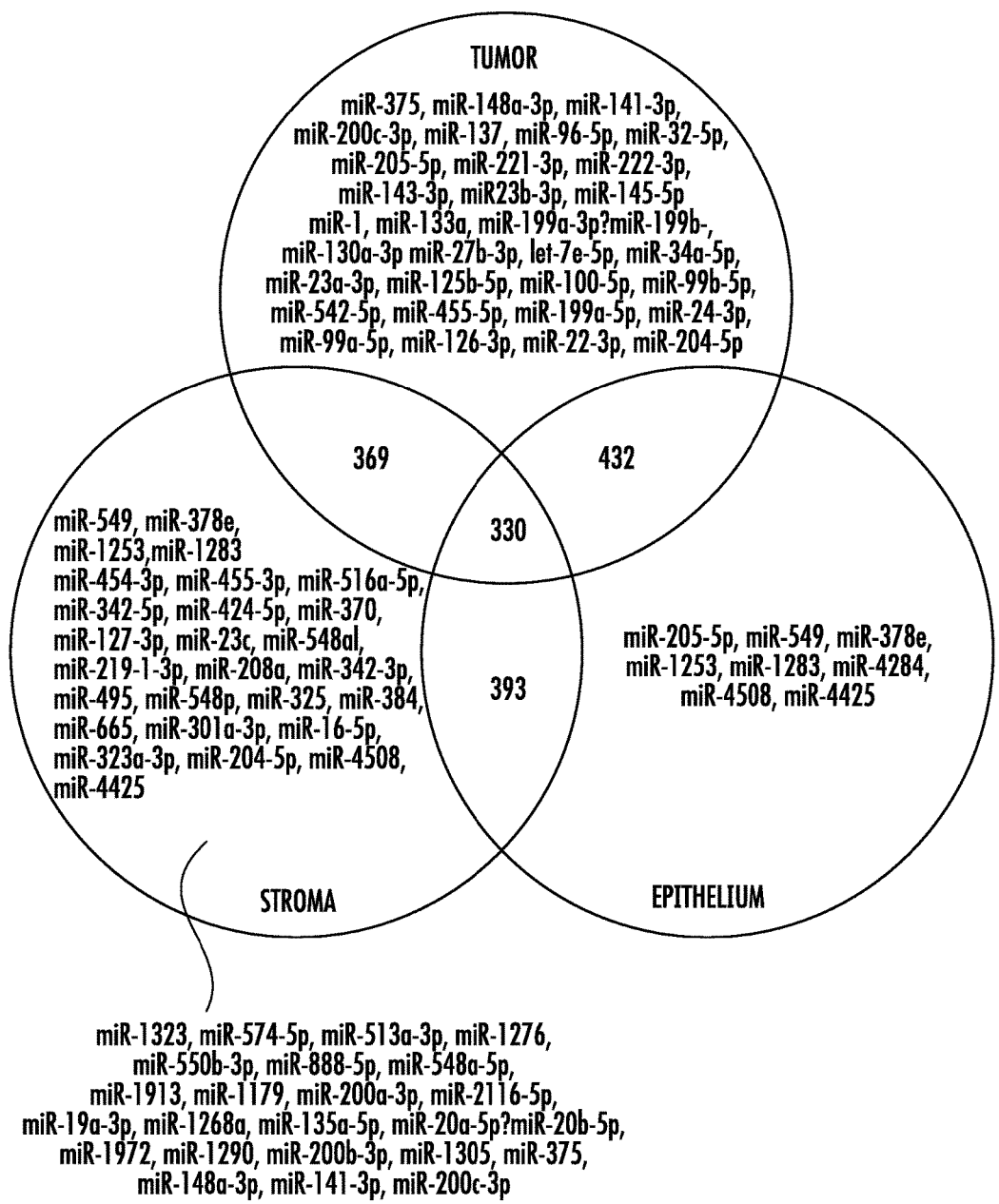
FIG. 2 shows a Venn diagram of the numbers of miRNAs commonly expressed among all tissue types (tumor, epithelium, and stroma), and lists by name those significantly differentially expressed 1.5-fold or greater between all tissues types.

Tumor samples had 7 miRNAs upregulated and 25 downregulated compared to both epithelium and stroma tissue, whereas epithelium samples had 5 miRNAs upregulated and 3 downregulated compared to tumor and stroma (FIG. 1). FIG. 1 is a Venn diagram showing numbers of commonly and differentially expressed miRNAs in prostate tumor, stroma, and epithelium. miRNAs commonly expressed among all tissue types as well as those significantly differentially expressed 1.5-fold or greater between all tissues types, using the repeated measures ANOVA are shown. miRNAs that were up-regulated (dark grey) and down-regulated (light grey) were identified in specific tissues meaning they were differentially expressed 1.5-fold or greater compared to the other two tissue types. Stroma samples appeared to be the most different when compared to either tumor or epithelium with 27 miRNAs upregulated and 23 downregulated (FIGS. 1 and 2). FIG. 2 gives the names of the miRNAs that were differentially expressed 1.5-fold or greater between all tissues types, using the repeated measures ANOVA. miR-1283 and miR-137 were for the first time identified to be deregulated in prostate tumor tissue compared to epithelium (Table 1).

miRNAs Predictive of PSA Recurrence Post-Prostatectomy: Univariate Analysis.

A clinical database was established for 43 PCa patients who underwent both RP and salvage RT Table 5. Risk factors included 32.5% of patients who had a Gleason score of 8 or above, 25.6% of patients who had seminal vesicle invasion or extraprostatic extension, and 41.9% of patients who had positive margins. Salvage RT was started at a median PSA value of 0.39 ng/ml. 19 patients (44.2%) experienced BF after salvage RT at a median time of 47.7 months (range 18.4-138.0 months). The median follow up times after RP and after salvage RT were 6.9 and 3.7 years, respectively.

TABLE 5

Clinical characteristics of 43 prostate cancer patients treated with salvage radiation therapy post-prostatectomy

| | PCa patients (n = 43) |
|---|---|
| Age at RP (years) | |
| Median (min-max) | 65 (45-73) |
| Follow-up post-RP (years) | |
| Median (min-max) | 6.9 (4.0-139) |
| Gleason score | |
| 6 | 8 (18.6%) |
| 7 | 21 (48.8%) |
| 8 | 8 (18.6%) |
| 9 | 5 (11.6%) |
| 10 | 1 (2.3%) |
| Pathological Tumor Stage | |
| T2 | 32 (74.4%) |
| T3 | 11 (25.6%) |
| Pathological N Stage | |
| N0 | 39 (89.0%) |
| N+ | 4 (11.0%) |
| Resection Status | |
| R0 | 20 (46.5%) |
| R1 | 18 (41.9%) |
| Rx | 5 (11.6%) |
| PSA at initial diagnosis (ng/mL) | 30 (69.8%) |
| <10 | |
| 10-20 | 10 (23.2%) |
| >20 | 3 (7.0%) |
| Risk groups (D'Amico) | |
| Low | 0 (0.0%) |
| Intermediate | 8 (18.6%) |
| High | 35 (81.4%) |
| Risk groups (Stephensen) | |
| Low | 25 (58.1%) |
| Intermediate | 7 (16.3%) |
| High | 7 (16.3%) |
| High+ | 4 (9.3%) |
| Androgen Deprivation Therapy | |
| Pre-op | 6 (13.9%) |
| Pre-RT | 3 (7.0%) |
| Concurrent | 4 (9.3%) |
| Time from RP to RT (months) | 34.5 |
| Median (min-max) | (10.4-123.1) |
| Follow-up post-RT (years) | 3.7 |

TABLE 5-continued

Clinical characteristics of 43 prostate cancer patients treated with salvage radiation therapy post-prostatectomy

| | PCa patients (n = 43) |
|---|---|
| Median (min-max) Pre-RT PSA (ng/mL) | (0.7-7.4) |
| <0.2 | 6 (14.0%) |
| 0.2-1.0 | 28 (65.1%) |
| 1.0-5.0 | 7 (16.2%) |
| >5.0 | 2 (4.7%) |
| Time from RT to BF (months) | 47.7 |
| Median (min-max) | (18.4-138.0) |
| Recurrence following RT | |
| Biochemical | 19 (44.2%) |
| Proven by imaging | 7 (16.3%) |
| Inside RT field | 0 (0.0%) |
| Outside RT field | 7 (16.3%) |

Using these data, miRNA expression was correlated with time to first biochemical recurrence to determine if miRNAs can predict biochemical recurrence post-RP. Time to first recurrence was defined as the time from prostatectomy to the start date of salvage RT. Using tumor expression only, 54 miRNAs were identified that were significantly differentially expressed 1.5-fold or greater between patients who had an early (≤36 months) versus late (>36 months) recurrence (Table 6). Thirty six months was used as the cut-off as it was near the median of time to recurrence. For another approach to identify miRNAs that correlated with time to first biochemical recurrence, patients were dichotomized according to median miRNA expression. Probabilities in the time to the first recurrences were compared between the two groups (high versus low miRNA expression) using log-rank tests. One hundred and twenty three miRNAs were identified that could differentiate the two groups in the time to first biochemical recurrence (p-value<0.05) Table 7.

TABLE 6 miRNA comparisons between early vs. late recurrence via ANOVA analysis

| miR_ID | Ratio (Late:Early) | p-value | Mean (Late) | Mean (Early) |
|---|---|---|---|---|
| hsa-miR-145-5p | 0.32202 | 0.0007 | 1630.94 | 5064.73 |
| hsa-miR-221-3p | 0.42762 | 0.0001 | 58.83 | 137.58 |
| hsa-miR-27b-3p | 0.43656 | 0.0007 | 252.18 | 577.66 |
| hsa-miR-200a-3p | 0.45447 | 0.0026 | 109.13 | 240.12 |
| hsa-miR-143-3p | 0.4547 | 0.0031 | 2009.27 | 4418.93 |
| hsa-miR-200b-3p | 0.47031 | 0.0108 | 218.29 | 464.15 |
| hsa-miR-26a-5p | 0.49082 | 0.0108 | 710.78 | 1448.16 |
| hsa-miR-29c-3p | 0.49275 | 0.0017 | 363.69 | 738.07 |
| hsa-miR-23b-3p | 0.49425 | 0.0041 | 373.89 | 756.47 |
| hsa-miR-24-3p | 0.51956 | 0.0019 | 95.16 | 183.16 |
| hsa-let-7e-5p | 0.53013 | 0.0006 | 182.99 | 345.18 |
| hsa-miR-130a-3p | 0.53557 | 0.0028 | 185.47 | 346.3 |
| hsa-miR-30c-5p | 0.54826 | 0.0008 | 54.97 | 100.26 |
| hsa-let-7f-5p | 0.55346 | 0.0015 | 346.13 | 625.4 |
| hsa-miR-195-5p | 0.55717 | 0.002 | 101.2 | 181.64 |
| hsa-miR-199a-3p?miR-199b- | 0.56099 | 0.0098 | 346.44 | 617.55 |
| hsa-miR-98 | 0.56358 | 0.0007 | 90.94 | 161.37 |
| hsa-miR-720 | 0.56623 | 0.0049 | 9822.96 | 17347.9 |
| hsa-miR-376a-3p | 0.56675 | 0.0008 | 75.02 | 132.38 |
| hsa-miR-361-5p | 0.5668 | 0.0036 | 120.3 | 212.24 |
| hsa-let-7a-5p | 0.56943 | 0.0015 | 5104.76 | 8964.63 |
| hsa-let-7c | 0.5733 | 0.0017 | 759.01 | 1323.94 |
| hsa-miR-23a-3p | 0.57904 | 0.0087 | 649.3 | 1121.34 |
| hsa-miR-1 | 0.58131 | 0.0148 | 63.43 | 109.11 |

TABLE 6-continued miRNA comparisons between early vs. late recurrence via ANOVA analysis

| miR_ID | Ratio (Late:Early) | p-value | Mean (Late) | Mean (Early) |
|---|---|---|---|---|
| hsa-miR-29b-3p | 0.58301 | 0.009 | 1144.22 | 1962.61 |
| hsa-miR-30b-5p | 0.59435 | 0.0202 | 457.48 | 769.71 |
| hsa-miR-125b-5p | 0.60235 | 0.0076 | 4021.05 | 6675.64 |
| hsa-let-7b-5p | 0.60465 | 0.0015 | 2390.02 | 3952.71 |
| hsa-miR-22-3p | 0.60552 | 0.0034 | 259.6 | 428.72 |
| hsa-miR-100-5p | 0.60641 | 0.0067 | 429.42 | 708.13 |
| hsa-miR-133a | 0.61408 | 0.0294 | 12.54 | 52.98 |
| hsa-miR-10b-5p | 0.61835 | 0.008 | 45.37 | 73.37 |
| hsa-miR-186-5p | 0.61856 | <.0001 | 49.96 | 80.78 |
| hsa-miR-34a-5p | 0.61913 | 0.0007 | 113.16 | 182.77 |
| hsa-miR-99a-5p | 0.62682 | 0.0164 | 8412.8 | 1342.14 |
| hsa-miR-497-5p | 0.62691 | 0.0137 | 81.88 | 130.61 |
| hsa-miR-301b | 0.628 | 0.0053 | 27.76 | 44.21 |
| hsa-let-7g-5p | 0.62865 | 0.012 | 1335.33 | 2124.12 |
| hsa-miR-374b-5p | 0.63133 | 0.0028 | 111.47 | 176.56 |
| hsa-miR-125a-5p | 0.63288 | 0.0025 | 101.97 | 161.11 |
| hsa-miR-222-3p | 0.63736 | 0.015 | 191.35 | 300.23 |
| hsa-miR-199a-5p | 0.63879 | 0.0082 | 130.97 | 205.04 |
| hsa-miR-324-5p | 0.64374 | <.0001 | 57.02 | 88.57 |
| hsa-miR-16-5p | 0.64478 | 0.0266 | 377.17 | 584.96 |
| hsa-miR-15a-5p | 0.64586 | 0.0112 | 256.56 | 397.23 |
| hsa-miR-429 | 0.6493 | 0.0489 | 60.01 | 92.42 |
| hsa-let-7d-5p | 0.65561 | 0.0014 | 166.14 | 253.42 |
| hsa-miR-29a-3p | 0.65694 | 0.0251 | 283.02 | 430.82 |
| hsa-miR-342-3p | 0.65812 | 0.028 | 192.38 | 292.32 |
| hsa-miR-141-3p | 0.65813 | 0.0285 | 545.9 | 829.48 |
| hsa-miR-541-3p | 1.51627 | 0.0057 | 26.71 | 17.29 |
| hsa-miR-568 | 1.5289 | 0.0054 | 36.92 | 24.15 |
| hsa-miR-342-5p | 1.9266 | 0.0091 | 19.29 | 10.01 |
| hsa-miR-137 | 2.69857 | 0.0111 | 233.38 | 86.48 |

TABLE 7 miRNAs that predict time to first recurrence via log-rank analysis

| miR_ID | p-value (log-rank) |
|---|---|
| hsa-miR-107 | 0.0001 |
| hsa-miR-576-3p | 0.0001 |
| hsa-let-7f-5p | 0.0003 |
| hsa-miR-1286 | 0.0003 |
| hsa-miR-486-3p | 0.0003 |
| hsa-miR-568 | 0.0005 |
| hsa-miR-106b-5p | 0.0006 |
| hsa-miR-890 | 0.0006 |
| hsa-miR-15a-5p | 0.0007 |
| hsa-miR-365a-3p | 0.0007 |
| hsa-miR-450b-5p | 0.0007 |
| hsa-miR-423-5p | 0.0008 |
| hsa-miR-572 | 0.0008 |
| hsa-miR-29c-3p | 0.0009 |
| hsa-miR-28-5p | 0.001 |
| hsa-miR-302a-3p | 0.0011 |
| hsa-miR-548aa | 0.0011 |
| hsa-miR-324-5p | 0.0014 |
| hsa-miR-18b-5p | 0.0015 |
| hsa-miR-1260b | 0.0016 |
| hsa-miR-141-3p | 0.0017 |
| hsa-miR-922 | 0.0019 |
| hsa-miR-148a-3p | 0.0021 |
| hsa-miR-148b-3p | 0.0022 |
| hsa-miR-98 | 0.0023 |
| hsa-miR-193a-5p | 0.0024 |
| hsa-miR-191-5p | 0.0025 |
| hsa-miR-548ak | 0.0027 |
| hsa-miR-1908 | 0.0029 |
| hsa-miR-548d-5p | 0.0033 |
| hsa-miR-375 | 0.0034 |
| hsa-miR-660-5p | 0.0034 |
| hsa-miR-194-5p | 0.0036 |

TABLE 7-continued miRNAs that predict time to first recurrence via log-rank analysis

| miR_ID | p-value (log-rank) |
|---|---|
| hsa-miR-483-3p | 0.0037 |
| hsa-miR-1257 | 0.0038 |
| hsa-miR-4454 | 0.0038 |
| hsa-let-7a-5p | 0.0041 |
| hsa-miR-638 | 0.0041 |
| hsa-miR-30b-5p | 0.0043 |
| hsa-miR-30c-5p | 0.0044 |
| hsa-miR-106a-5p?miR-17-5p | 0.0045 |
| hsa-let-7e-5p | 0.0046 |
| hsa-miR-1276 | 0.0047 |
| hsa-miR-516a-3p | 0.0047 |
| hsa-miR-30d-5p | 0.0049 |
| hsa-miR-320a | 0.0049 |
| hsa-miR-216a | 0.0059 |
| hsa-miR-1323 | 0.0063 |
| hsa-miR-450b-3p | 0.0069 |
| hsa-miR-3136-5p | 0.0074 |
| hsa-let-7g-5p | 0.0075 |
| hsa-miR-93-5p | 0.0075 |
| hsa-miR-885-5p | 0.0082 |
| hsa-miR-1206 | 0.0085 |
| hsa-miR-421 | 0.0085 |
| hsa-miR-1200 | 0.0091 |
| hsa-miR-548am-3p | 0.0107 |
| hsa-miR-34c-3p | 0.0111 |
| hsa-miR-3934 | 0.0112 |
| hsa-miR-497-5p | 0.0122 |
| hsa-miR-1205 | 0.0123 |
| hsa-miR-15b-5p | 0.0123 |
| hsa-miR-508-5p | 0.0127 |
| hsa-miR-409-3p | 0.0128 |
| hsa-miR-376a-3p | 0.0134 |
| hsa-miR-762 | 0.0138 |
| hsa-miR-195-5p | 0.0141 |
| hsa-miR-654-5p | 0.0151 |
| hsa-miR-130a-3p | 0.0153 |
| hsa-miR-1290 | 0.0154 |
| hsa-miR-1288 | 0.0157 |
| hsa-miR-613 | 0.0163 |
| hsa-miR-1279 | 0.0168 |
| hsa-miR-376c | 0.017 |
| hsa-miR-135a-5p | 0.0177 |
| hsa-miR-23b-3p | 0.0178 |
| hsa-miR-1915-3p | 0.0182 |
| hsa-miR-27b-3p | 0.0187 |
| hsa-miR-362-5p | 0.0195 |
| hsa-miR-4448 | 0.0198 |
| hsa-miR-196a-5p | 0.0199 |
| hsa-miR-541-3p | 0.0203 |
| hsa-miR-548l | 0.0207 |
| hsa-miR-570-3p | 0.0214 |
| hsa-miR-767-3p | 0.0214 |
| hsa-let-7d-5p | 0.0215 |
| hsa-miR-92a-3p | 0.0219 |
| hsa-miR-24-3p | 0.0224 |
| hsa-miR-221-3p | 0.0225 |
| hsa-miR-3168 | 0.0225 |
| hsa-miR-199a-3p?miR-199b- | 0.0237 |
| hsa-miR-4508 | 0.0241 |
| hsa-miR-374b-5p | 0.0251 |
| hsa-miR-548t-5p | 0.0251 |
| hsa-miR-3180 | 0.0252 |
| hsa-miR-495 | 0.0279 |
| hsa-miR-19b-3p | 0.0286 |
| hsa-miR-1180 | 0.0291 |
| hsa-miR-3196 | 0.0304 |
| hsa-miR-566 | 0.0325 |
| hsa-miR-524-3p | 0.0331 |
| hsa-miR-429 | 0.0332 |
| hsa-miR-145-5p | 0.0361 |
| hsa-let-7i-5p | 0.0366 |
| hsa-miR-29b-3p | 0.0374 |
| hsa-miR-137 | 0.0377 |
| hsa-miR-149-5p | 0.0378 |
| hsa-miR-891b | 0.0382 |
| hsa-miR-514b-5p | 0.0394 |
| hsa-miR-549 | 0.0394 |
| hsa-miR-513a-3p | 0.0403 |
| hsa-miR-548z | 0.041 |
| hsa-miR-511 | 0.0423 |
| hsa-miR-99b-5p | 0.0424 |
| hsa-miR-548v | 0.0438 |
| hsa-miR-766-3p | 0.0439 |
| hsa-miR-1245b-5p | 0.0445 |
| hsa-miR-143-3p | 0.0465 |
| hsa-miR-877-5p | 0.0465 |
| hsa-miR-146b-5p | 0.0473 |
| hsa-miR-515-3p | 0.0484 |
| hsa-miR-1179 | 0.0485 |
| hsa-miR-20a-5p?miR-20b-5p | 0.0488 | miRNAs Predictive of PSA Recurrence Post-Prostatectomy: Multivariate Analysis.

Figure 3A:
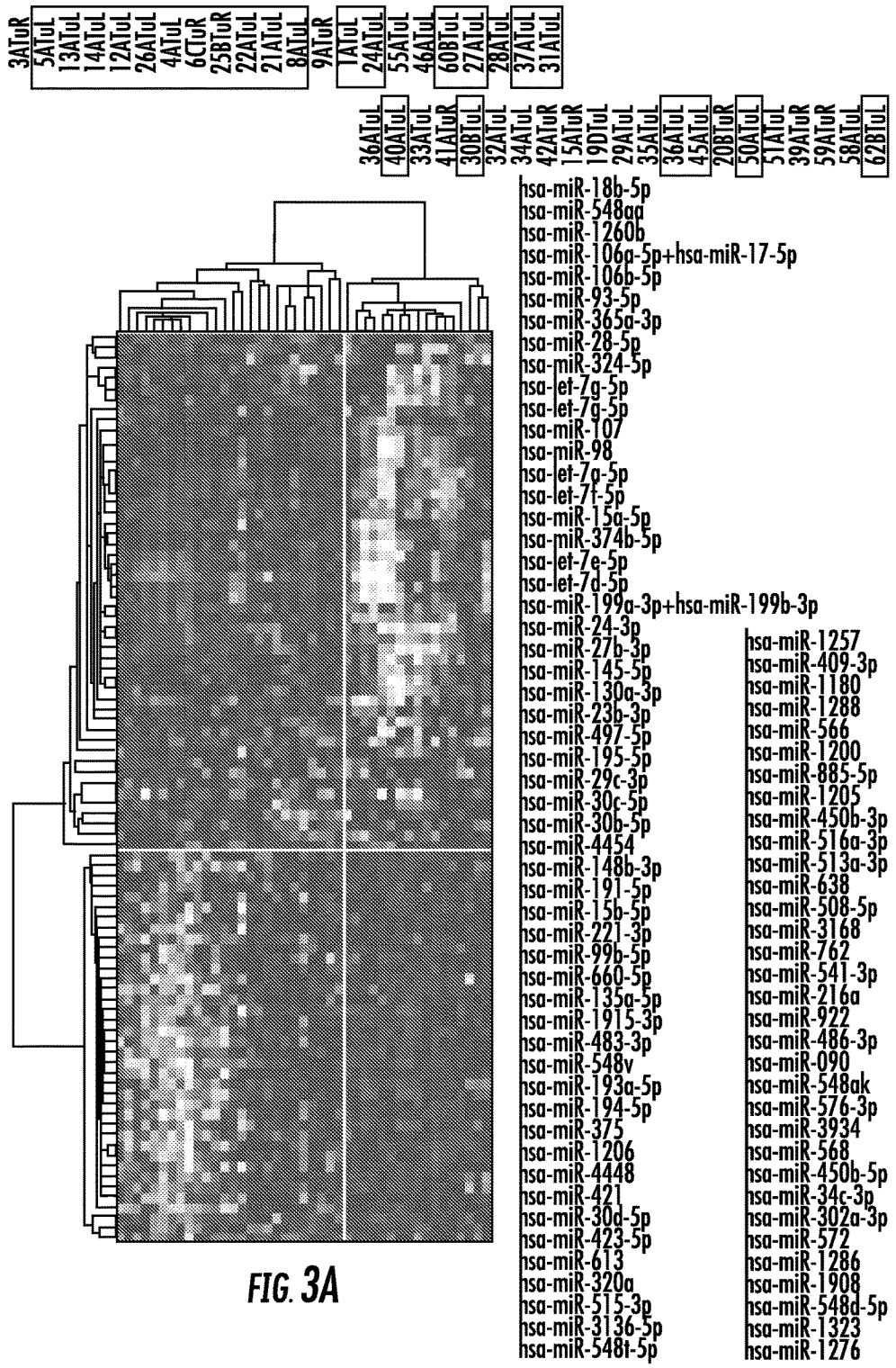
FIG. 3A shows a cluster analysis of 88 miRNAs predictive of first biochemical recurrence. The analysis may distinguish markers relating to early versus late recurrence after radical prostatectomy.
Figure 3B:
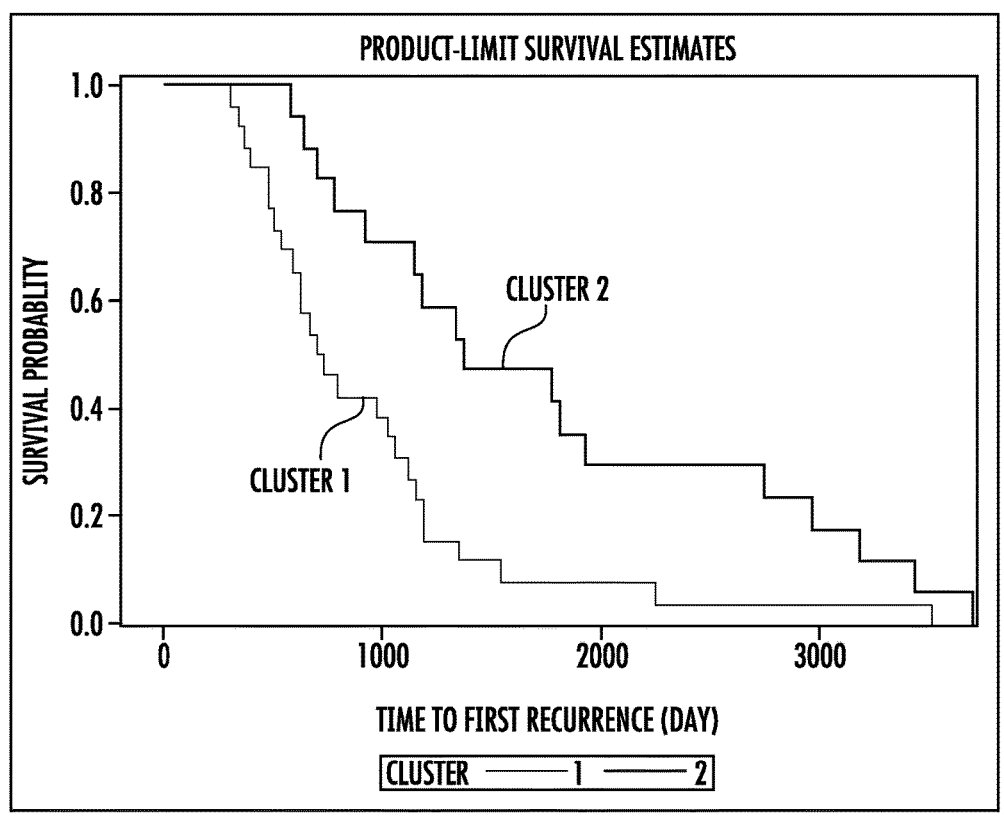
FIG. 3B shows a Kaplan-Meier plot of the cluster analysis in FIG. 3A

In order to determine if miRNAs can be independent markers of biochemical recurrence post-RP, two multivariate Cox regression analyses were performed using all 123 miRNAs identified to be predictive of biochemical recurrence post-prostatectomy (p-value<0.05) by univariate log-rank analysis Table 7. The first multivariate analysis considered initial PSA value (continuous) and Gleason score; age and resection status was eliminated as it did not seem to affect the recurrence in univariate analysis. Upon analysis of the first recurrence using multivariable Cox regression analysis, 97 miRNAs had p-values<0.05 (Table 8). In the second multivariate analysis, different clinical factors were taken into consideration. Three clinical covariates were examined independently, D'Amico score, Stephenson score (categorical), and Stephenson score (continuous), respectively to identify miRNAs associated with time to first recurrence. miRNAs were removed from further analysis if a significant p-value (<0.05) was not obtained in any of the three analyses which resulted in 88 miRNAs that were statistically associated with time to first recurrence after multivariate analysis (Table 2). Patients were classified into two groups using unbiased hierarchical cluster analysis for those selected 88 miRNAs (FIG. 3A). For FIGS. 3A-3B, cluster analysis was performed using the statistically significant 88 miRNAs predictive of first biochemical recurrence using Cox regression multivariable analysis (D'Amico score, Stephensen score (categorical), and Stephensen score (continuous). FIG. 3A demonstrates how this signature appears to differentiate between patients with early recurrence (<36 months) versus those with late recurrence (>36 months). FIG. 3B shows Kaplan-Meier plots that were generated using the two cluster groups. Cluster 1, the left cluster, is the early recurrence group. Cluster 2, the right cluster, is the late recurrence group. The Kaplan-Meier method showed that the probabilities in the time to first biochemical recurrence were significantly different between the two groups of patients with distinguished miRNA signatures (log-rank, p=0.005).

TABLE 8 miRNAs that predict time to first biochemical recurrence post-radical prostatectomy (RP) via multivariate Cox regression analysis

| miR_ID | Hazard Ratio (High vs Low) | p-value | 95% CI |
|---|---|---|---|
| hsa-miR-107 | 9.61 | <.0001 | (3.47, 26.58) |
| hsa-miR-1915-3p | 8.0464 | 0.0002 | (2.65, 24.44) |
| hsa-miR-106b-5p | 5.5337 | 0.0008 | (2.03, 15.09) |
| hsa-miR-421 | 4.9287 | <.0001 | (2.28, 10.67) |
| hsa-let-7f-5p | 4.6887 | 0.0005 | (1.98, 11.12) |
| hsa-miR-18b-5p | 4.6492 | 0.001 | (1.87, 11.58) |
| hsa-miR-106a-5p?miR-17-5p | 4.565 | 0.0023 | (1.72, 12.12) |
| hsa-miR-15a-5p | 4.4285 | 0.0016 | (1.76, 11.13) |
| hsa-miR-191-5p | 4.1342 | 0.003 | (1.62, 10.54) |
| hsa-miR-1279 | 4.077 | 0.0015 | (1.71, 9.73) |
| hsa-miR-29c-3p | 3.8189 | 0.0014 | (1.68, 8.68) |
| hsa-miR-4454 | 3.8179 | 0.0037 | (1.55, 9.42) |
| hsa-miR-93-5p | 3.7934 | 0.0023 | (1.61, 8.93) |
| hsa-miR-376a-3p | 3.7741 | 0.0013 | (1.68, 8.47) |
| hsa-miR-423-5p | 3.7727 | 0.0014 | (1.67, 8.54) |
| hsa-miR-149-5p | 3.5734 | 0.0008 | (1.7, 7.52) |
| hsa-miR-20a-5p?miR-20b-5p | 3.4053 | 0.0074 | (1.39, 8.35) |
| hsa-miR-221-3p | 3.3326 | 0.0025 | (1.53, 7.27) |
| hsa-miR-141-3p | 3.1033 | 0.0113 | (1.29, 7.45) |
| hsa-miR-19b-3p | 3.077 | 0.0201 | (1.19, 7.94) |
| hsa-miR-877-5p | 3.0044 | 0.0149 | (1.24, 7.28) |
| hsa-miR-497-5p | 3.0009 | 0.0052 | (1.39, 6.49) |
| hsa-miR-148a-3p | 2.9478 | 0.0075 | (1.33, 6.51) |
| hsa-miR-27b-3p | 2.9186 | 0.007 | (1.34, 6.35) |
| hsa-miR-30c-5p | 2.916 | 0.0034 | (1.42, 5.97) |
| hsa-miR-28-5p | 2.9121 | 0.0025 | (1.46, 5.82) |
| hsa-let-7e-5p | 2.8575 | 0.0042 | (1.39, 5.86) |
| hsa-miR-376c | 2.8526 | 0.0051 | (1.37, 5.94) |
| hsa-miR-324-5p | 2.8459 | 0.0064 | (1.34, 6.04) |
| hsa-miR-98 | 2.8348 | 0.0031 | (1.42, 5.66) |
| hsa-miR-548aa | 2.8047 | 0.0133 | (1.24, 6.34) |
| hsa-miR-30d-5p | 2.7969 | 0.0085 | (1.3, 6.01) |
| hsa-miR-92a-3p | 2.7473 | 0.016 | (1.21, 6.25) |
| hsa-miR-549 | 2.7108 | 0.0164 | (1.2, 6.12) |
| hsa-let-7g-5p | 2.7026 | 0.0053 | (1.34, 5.44) |
| hsa-miR-570-3p | 2.6726 | 0.0123 | (1.24, 5.77) |
| hsa-miR-365a-3p | 2.5484 | 0.0241 | (1.13, 5.75) |
| hsa-miR-146b-5p | 2.5192 | 0.0225 | (1.14, 5.57) |
| hsa-miR-23b-3p | 2.4507 | 0.0129 | (1.21, 4.97) |
| hsa-miR-194-5p | 2.4328 | 0.0246 | (1.12, 5.28) |
| hsa-let-7a-5p | 2.4173 | 0.0116 | (1.22, 4.8) |
| hsa-miR-483-3p | 2.4078 | 0.0429 | (1.03, 5.64) |
| hsa-miR-130a-3p | 2.3785 | 0.0139 | (1.19, 4.74) |
| hsa-miR-193a-5p | 2.3649 | 0.0259 | (1.11, 5.04) |
| hsa-miR-3196 | 2.3296 | 0.0196 | (1.15, 4.74) |
| hsa-miR-195-5p | 2.3243 | 0.0153 | (1.18, 4.6) |
| hsa-miR-548v | 2.3194 | 0.0484 | (1.01, 5.35) |
| hsa-miR-1260b | 2.2893 | 0.0388 | (1.04, 5.02) |
| hsa-miR-374b-5p | 2.2845 | 0.0228 | (1.12, 4.65) |
| hsa-miR-24-3p | 2.2661 | 0.0204 | (1.14, 4.52) |
| hsa-miR-1290 | 2.2529 | 0.032 | (1.07, 4.73) |
| hsa-miR-199a-3p?miR-199b- | 2.2506 | 0.0237 | (1.11, 4.54) |
| hsa-miR-135a-5p | 2.2052 | 0.0232 | (1.11, 4.36) |
| hsa-let-7d-5p | 2.121 | 0.0379 | (1.04, 4.31) |
| hsa-miR-3136-5p | 0.4684 | 0.0344 | (0.23, 0.95) |
| hsa-miR-891b | 0.4554 | 0.0418 | (0.21, 0.97) |
| hsa-miR-762 | 0.4527 | 0.0277 | (0.22, 0.92) |
| hsa-miR-1276 | 0.4493 | 0.0347 | (0.21, 0.94) |
| hsa-miR-1288 | 0.4302 | 0.015 | (0.22, 0.85) |
| hsa-miR-1205 | 0.4298 | 0.0173 | (0.21, 0.86) |
| hsa-miR-3180 | 0.4203 | 0.0266 | (0.2, 0.9) |
| hsa-miR-613 | 0.4178 | 0.0252 | (0.19, 0.9) |
| hsa-miR-1257 | 0.4124 | 0.0323 | (0.18, 0.93) |
| hsa-miR-1323 | 0.4113 | 0.0329 | (0.18, 0.93) |
| hsa-miR-548l | 0.408 | 0.0206 | (0.19, 0.87) |
| hsa-miR-922 | 0.4068 | 0.0257 | (0.18, 0.9) |
| hsa-miR-508-5p | 0.3865 | 0.0117 | (0.18, 0.81) |
| hsa-miR-516a-3p | 0.3848 | 0.0219 | (0.17, 0.87) |
| hsa-miR-34c-3p | 0.3818 | 0.0076 | (0.19, 0.77) |
| hsa-miR-3934 | 0.3657 | 0.0095 | (0.17, 0.78) |
| hsa-miR-548t-5p | 0.3582 | 0.0067 | (0.17, 0.75) |
| hsa-miR-196a-5p | 0.3462 | 0.0051 | (0.16, 0.73) |
| hsa-miR-890 | 0.3455 | 0.0123 | (0.15, 0.79) |
| hsa-miR-137 | 0.3454 | 0.0039 | (0.17, 0.71) |
| hsa-miR-486-3p | 0.3411 | 0.0075 | (0.16, 0.75) |
| hsa-miR-511 | 0.3411 | 0.0168 | (0.14, 0.82) |
| hsa-miR-885-5p | 0.3404 | 0.0034 | (0.17, 0.7) |
| hsa-miR-495 | 0.3343 | 0.0028 | (0.16, 0.69) |
| hsa-miR-638 | 0.3327 | 0.0029 | (0.16, 0.69) |
| hsa-miR-766-3p | 0.3316 | 0.0029 | (0.16, 0.69) |
| hsa-miR-320a | 0.3305 | 0.0085 | (0.14, 0.75) |
| hsa-miR-1200 | 0.3237 | 0.0039 | (0.15, 0.7) |
| hsa-miR-566 | 0.3135 | 0.0084 | (0.13, 0.74) |
| hsa-miR-450b-5p | 0.3114 | 0.0064 | (0.13, 0.72) |
| hsa-miR-4508 | 0.3077 | 0.0024 | (0.14, 0.66) |
| hsa-miR-548ak | 0.2636 | 0.0011 | (0.12, 0.59) |
| hsa-miR-1908 | 0.2623 | 0.0027 | (0.11, 0.63) |
| hsa-miR-409-3p | 0.2597 | 0.0017 | (0.11, 0.6) |
| hsa-miR-1286 | 0.2488 | 0.0016 | (0.1, 0.59) |
| hsa-miR-450b-3p | 0.2468 | 0.0027 | (0.1, 0.61) |
| hsa-miR-654-5p | 0.2446 | 0.0003 | (0.11, 0.53) |
| hsa-miR-576-3p | 0.209 | 0.0004 | (0.09, 0.5) |
| hsa-miR-216a | 0.1914 | 0.0001 | (0.08, 0.45) |
| hsa-miR-568 | 0.18 | 0.0007 | (0.07, 0.49) |
| hsa-miR-302a-3p | 0.1646 | 0.0002 | (0.06, 0.42) |
| hsa-miR-572 | 0.1507 | <.0001 | (0.06, 0.35) |
| hsa-miR-1180 | 0.1279 | 0.0002 | (0.04, 0.38) | miRNAs Predictive of PSA Recurrence Post-Salvage RT: Univariate Analysis.

miRNAs that could predict biochemical recurrence after salvage RT treatment are of utmost interest. At this time, no studies have examined miRNAs associated with clinical outcomes following post-RP salvage radiation. The recurrence after salvage radiation treatment (also referred to as the $2^{nd}$ recurrence) was defined as a rise in PSA to ≥0.2 ng/mL at least twice consecutively following the nadir (Cookson et al., Journal of Urology, 2007). In the patient cohort, 19/43 patients experienced biochemical recurrence after salvage radiotherapy Table 5. Further, using tumor miRNA expression only, 4 miRNAs were identified that were significantly expressed 1.5-fold or greater in patients who experienced a second recurrence when compared with those who did not (p-value<0.05) (Table 9). In the univariate log-rank analysis, 24 miRNAs were identified, which could predict those who recurred a second time after salvage RT from those who did not recur (p-value<0.05) (Table 10).

TABLE 9 miRNAs that predict biochemical recurrence post-salvage radiation therapy (RT) via ANOVA

| miR_ID | Ratio (Recurrence:Non-recurrence) | p-value | Mean (Non-recurrence) | Mean (Recurrence) |
|---|---|---|---|---|
| hsa-miR-4443 | 0.63 | 0.008 | 213.5 | 133.89 |
| hsa-miR-626 | 0.65 | 0.002 | 38.89 | 25.45 |
| hsa-miR-1202 | 0.67 | <.0001 | 33.95 | 22.64 |
| hsa-miR-10b-5p | 1.61 | 0.009 | 47.5 | 76.6 |

TABLE 10 miRNAs that predict biochemical recurrence post-salvage
radiation therapy (RT) via log-rank analysis

| miR_ID | p-value (log-rank) |
| --- | --- |
| hsa-miR-628-3p | 0.0028 |
| hsa-miR-924 | 0.0039 |
| hsa-miR-626 | 0.0056 |
| hsa-miR-1202 | 0.0096 |
| hsa-miR-563 | 0.0234 |
| hsa-miR-598 | 0.0249 |
| hsa-miR-30d-5p | 0.0293 |
| hsa-miR-491-5p | 0.0298 |
| hsa-miR-4516 | 0.0326 |
| hsa-miR-601 | 0.0327 |
| hsa-miR-508-3p | 0.0356 |
| hsa-miR-576-5p | 0.0358 |
| hsa-miR-320e | 0.0394 |
| hsa-miR-134 | 0.0401 |
| hsa-miR-548an | 0.043 |
| hsa-miR-1303 | 0.0443 |
| hsa-miR-551a | 0.0449 |
| hsa-miR-761 | 0.0464 |
| hsa-miR-1244 | 0.0469 |
| hsa-miR-96-5p | 0.0471 |
| hsa-miR-658 | 0.0476 |
| hsa-miR-1193 | 0.0481 |
| hsa-miR-597 | 0.0482 |
| hsa-miR-1913 | 0.0483 | miRNAs Predictive of PSA Recurrence Post-Salvage RT: Multivariate Analysis. Similarly, in order to determine if miRNAs can independently predict biochemical recurrence post-salvage RT, multivariate Cox regression analyses were performed using the 24 miRNAs that were significantly associated (p-value<0.05) with recurrence post-salvage RT by univariate log-rank analysis (Table 10). Due to the small sample size and number of events, only two covariates were examined in the multivariate analysis. The multivariate analysis was performed using lymph node status and Gleason score (these factors were chosen as having the lowest p-values upon univariate analysis as shown in (Table 11), leading to identification of 9 miRNAs that predict biochemical recurrence post-salvage RT (Table 3).

TABLE 11

Univariate analysis for molecular and clinical variables

|  | Time to Failure Post-RP p-value | Failure Post-Salvage RT p-value |
| --- | --- | --- |
| 88 miRNA cluster | 0.005 | n/a |
| Predictive Salvage RT Model | n/a | <0.001 |
| Gleason Score | 0.36 | 0.02 |
| Lymph Node Involvement | 0.11 | 0.001 |
| Positive Resection Status | 0.99 | 0.13 |
| Pathologic Tumor Stage | 0.1 | 0.38 |
| PSA | 0.63 (pre-op) | 0.29 (pre-RT) |
| D'Amico | 0.01 | 0.88 |
| Stephenson (post-RP) | 0.002 | 0.04 |

Predictive Effect of miR-601+miR-4516 & Development of a miRNA-Based Predictive Salvage RT Model.

Figure 4:
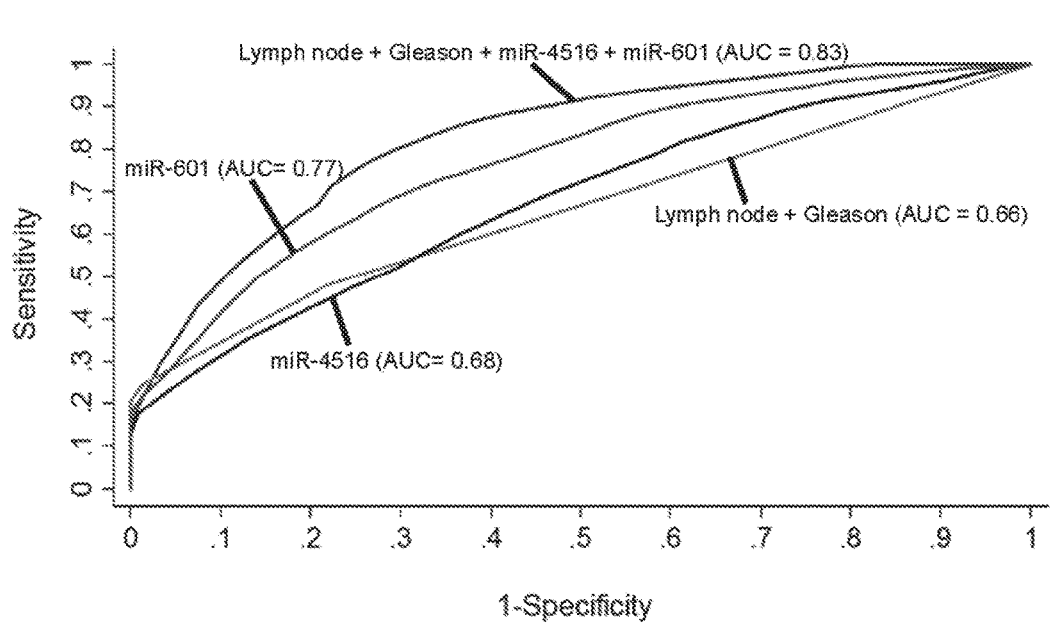
FIG. 4 shows an area under the receiver operating characteristic curve (AUC) of a miRNA-based predictive salvage RT model.

Lymph node status, Gleason score and the 9 miRNAs were used as covariates in a COX regression model and stepwise model selection strategy was used to capture miRNAs which could be good candidates in predicting the biochemical recurrence post-salvage RT. The two miRNAs, miR-601 and miR-4516 alone and together with Gleason score and lymph node status were selected by the model. FIG. 4 shows an area under the receiver operating characteristic curve (AUC) of a miRNA-based predictive salvage RT model. The curve was generated using the nearest neighbor estimation method (Heagerty et al. *Biometrics*, 2000). Specifically, AUC curves were generated using a stepwise Cox regression model to determine a signature predictive of biochemical recurrence post-salvage radiation therapy. An AUC for lymph node and Gleason score was found to be 0.66, the addition of miR-601 and miR-4516 increased the AUC to 0.83 (FIG. 4). Interestingly, each miRNA alone (miR-601 AUC=0.77 and miR-4516 AUC=0.68) or together (miR-601+miR-4516 AUC=0.76) (FIG. 4) had a better predictive capability than the combination of positive lymph nodes together with Gleason score (FIG. 4).

Figure 5:
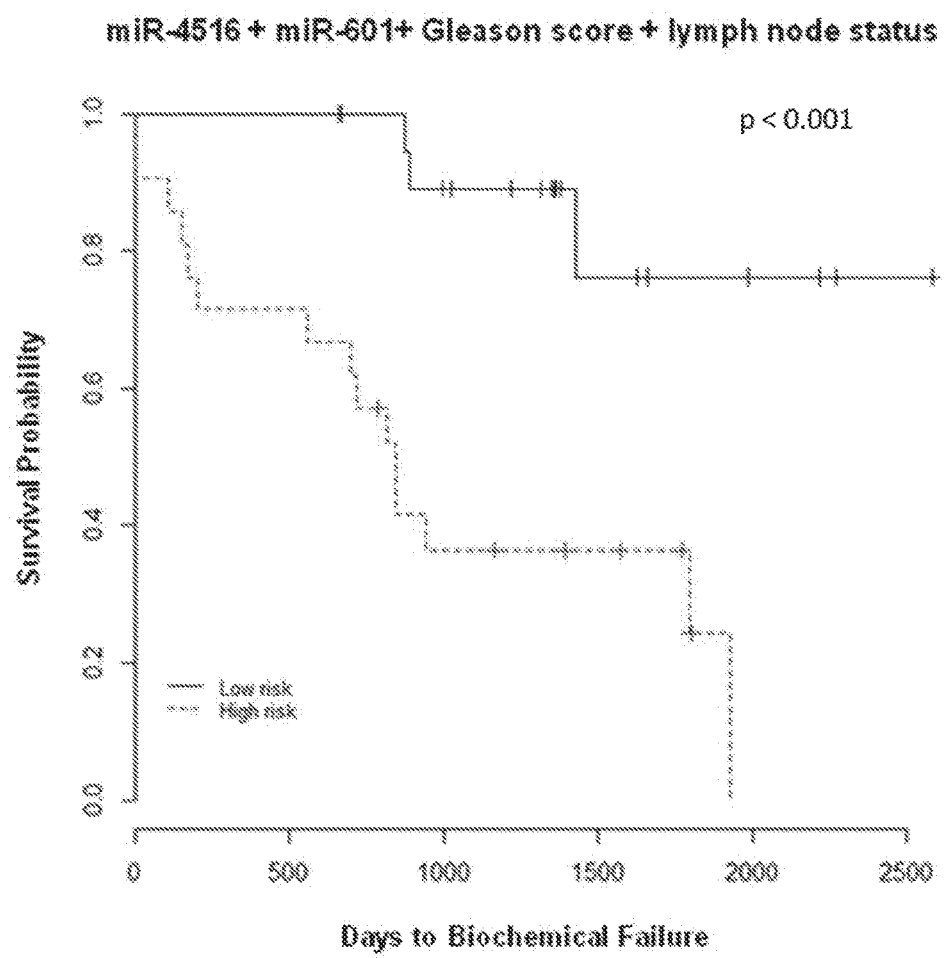
FIG. 5 shows a Kaplan-Meier plot for distinguishing early versus late recurrence after salvage radiation therapy.

FIG. 5 is a Kaplan-Meier plot that shows estimates of miRNA-based predictive salvage RT model. The plot was generated using the miR-4516+miR-601+Gleason score+lymph node status model for biochemical recurrence post salvage radiation therapy. Using the median risk score generated by this model (miR-4516, miR-601, Gleason score, and lymph node status), patients were classified as high or low risk groups. The probabilities in recurrence post-salvage RT of the two groups were found to be significantly different (log-rank, p<0.01).

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

What is claimed is:

1. A method for treating a subject based on a high biochemical recurrence risk score following post-prostatectomy salvage radiation therapy, comprising
    a) determining a miRNA expression profile from a sample from the subject of at least 1 miRNA selected from the group consisting of hsa-miR-628-3p, hsa-miR-1193, hsa-miR-601, hsa-miR-4516, hsa-miR-320e, hsa-miR-508-3p, hsa-miR-598, hsa-miR-626, hsa-miR-563; and
    b) calculating a-miRNA-based recurrence risk score from the miRNA expression profile; wherein a high recurrence risk score when compared to Gleason score and lymph node status alone, wherein a high recurrence risk score is based on a regression value of about 0.5 or greater, is an indication of biochemical recurrence within 1 to 5 years; and
    c) treating the subject with a high recurrence risk score with adjuvant therapy, radiation therapy, palliative care, or a combination thereof.

2. The method of claim 1, wherein the at least 1 miRNA comprises miR-4516, miR-601, or a combination thereof.

3. The method of claim 1, wherein the adjuvant therapy comprises chemotherapy, hormone therapy, biologic therapy, radiation therapy, or a combination thereof.

4. The method of claim 1, wherein the salvage radiation therapy comprises external beam radiation therapy or internal radiation therapy.

5. The method of claim 1, wherein the sample is a tumor or a bodily fluid.

6. The method of claim 1, further comprising grading a tumor according to a Gleason score, and using the Gleason score as a covariate in calculating the recurrence risk score.

7. The method of claim 1, further comprising determining one or more properties of a tumor including the subject's age, PSA levels, lymph node classification (pN), pathologic tumor classification (pT), resection status, D'Amico classification, and/or Stephenson nomograms and using the one or more properties as covariates in calculating the recurrence risk score.

* * * * *

UNITED STATES PATENT AND TRADEMARK OFFICE
CERTIFICATE OF CORRECTION

PATENT NO.         : 10,480,033 B2
APPLICATION NO.    : 15/543721
DATED              : November 19, 2019
INVENTOR(S)        : Arnab Chakravarti et al.

It is certified that error appears in the above-identified patent and that said Letters Patent is hereby corrected as shown below:

In the Specification

Column 1, Lines 18-21 replace the Government Support Clause with:
--This invention was made with government support under grant number CA188500 awarded by the National Institutes of Health. The government has certain rights in the invention.--

Signed and Sealed this
Sixth Day of October, 2020

Andrei Iancu
*Director of the United States Patent and Trademark Office*